United States Patent
Mody et al.

(10) Patent No.: US 7,226,446 B1
(45) Date of Patent: Jun. 5, 2007

(54) SURGICAL MICROWAVE ABLATION ASSEMBLY

(76) Inventors: Dinesh Mody, 5631 Highcrest Ct., Pleasanton, CA (US) 94588; Dany Berube, 39224 Guardino Dr., #101, Fremont, CA (US) 94538; Patrick Morin, 39224 Guardino Dr., #101, Fremont, CA (US) 94538; Sing-Fatt Chin, 40340 Strawflower Way, Fremont, CA (US) 94538

( * ) Notice: Subject to any disclaimer, the term of this patent is extended or adjusted under 35 U.S.C. 154(b) by 327 days.

(21) Appl. No.: 09/660,466

(22) Filed: Sep. 12, 2000

Related U.S. Application Data

(63) Continuation-in-part of application No. 09/305,143, filed on May 4, 1999, now Pat. No. 6,325,796.

(51) Int. Cl.
*A61B 18/18* (2006.01)

(52) U.S. Cl. .......................... 606/33; 606/41

(58) Field of Classification Search ............ 607/100–2, 607/154, 156, 96; 606/31–34, 41, 46
See application file for complete search history.

(56) References Cited

U.S. PATENT DOCUMENTS

| | | |
|---|---|---|
| 1,586,645 A | 6/1926 | Bierman |
| 3,598,108 A | 8/1971 | Jamshidi et al. |
| 3,827,436 A | 8/1974 | Stumpf et al. |
| 3,831,607 A | 8/1974 | Lindemann |
| 3,886,944 A | 6/1975 | Jamshidi |
| 3,976,082 A | 8/1976 | Schmitt |
| 4,011,872 A | 3/1977 | Komiya |
| 4,033,357 A | 7/1977 | Helland et al. |
| 4,045,056 A | 8/1977 | Kandakov et al. |
| 4,073,287 A | 2/1978 | Bradley et al. |
| 4,204,549 A | 5/1980 | Paglione |
| 4,244,371 A | 1/1981 | Farin |
| 4,268,937 A | 5/1981 | Grimshaw |
| 4,312,364 A | 1/1982 | Convert et al. ............. 128/804 |

(Continued)

FOREIGN PATENT DOCUMENTS

EP 0139607 A1 5/1985

(Continued)

OTHER PUBLICATIONS

Sato et al, "Two long-term survivors after microwave coagulation therapy for hepatocellular carcinoma: A case report," Hepatogastroenterology, Jul. 1996; 43(10):1035-1039 (Abstract).
Sato et al, "Microwave coagulation therapy for hepatocellular carcinoma," Gastroenterology, May 1996: 110(5):1507-1514 (Abstract).
Murakami et al., "Treatment of hepatocellular carcinoma: Value of percutaneous microwave coagulation," AJR Am J Roentgenol, May 1995: 164(5):1159-1164 (Abstract).
Labonté et al., "Monopole antennas for microwave catheter ablation," IEEE Transactions On Microwave Theory and Techniques, vol. 44, No. 10, 1832-1840 (1996).

(Continued)

*Primary Examiner*—Roy D. Gibson
*Assistant Examiner*—Aaron Roane
(74) *Attorney, Agent, or Firm*—Law Offices of Alan W. Cannon

(57) ABSTRACT

An ablation assembly capable of ablating tissues inside the cavity of an organ is disclosed. The ablation assembly generally includes an ablative energy source and an ablative energy delivery device coupled to the ablative energy source. The ablative energy delivery device is configured for delivering ablative energy sufficiently strong to cause tissue ablation. The ablative energy delivery device generally includes a penetration end adapted to penetrate through a wall of an organ and an angular component that is used to position the device inside the organ after the device has penetrated through the wall of the organ.

28 Claims, 24 Drawing Sheets

U.S. PATENT DOCUMENTS

| | | | |
|---|---|---|---|
| 4,416,276 A | 11/1983 | Newton et al. | |
| 4,445,892 A | 5/1984 | Hussein et al. | |
| 4,448,198 A | 5/1984 | Turner | 128/422 |
| 4,462,412 A | 7/1984 | Turner | |
| 4,465,079 A | 8/1984 | Dickhudt | |
| 4,476,872 A | 10/1984 | Perlin | |
| 4,494,539 A | 1/1985 | Zenitani et al. | 128/303.1 |
| 4,522,212 A | 6/1985 | Gelinas et al. | |
| 4,564,200 A | 1/1986 | Loring et al. | |
| 4,565,200 A | 1/1986 | Cosman | |
| 4,573,473 A | 3/1986 | Hess | |
| 4,583,556 A | 4/1986 | Hines et al. | |
| 4,601,296 A | 7/1986 | Yerushalmi | |
| 4,611,604 A | 9/1986 | Botvidsson et al. | |
| 4,640,983 A | 2/1987 | Comte | |
| 4,641,646 A | 2/1987 | Schultz et al. | |
| 4,641,649 A | 2/1987 | Walinsky et al. | |
| 4,643,186 A | 2/1987 | Rosen et al. | |
| 4,655,219 A | 4/1987 | Petruzzi | |
| 4,657,015 A | 4/1987 | Irnich | |
| 4,660,571 A | 4/1987 | Hess et al. | |
| 4,681,122 A | 7/1987 | Winters et al. | |
| 4,685,459 A | 8/1987 | Koch et al. | |
| 4,699,147 A | 10/1987 | Chilson et al. | |
| 4,700,716 A | 10/1987 | Kasevich et al. | |
| 4,763,668 A | 8/1988 | Macek et al. | |
| 4,785,815 A | 11/1988 | Cohen | |
| 4,800,899 A | 1/1989 | Elliott | 128/804 |
| 4,823,812 A | 4/1989 | Eshel et al. | |
| 4,825,880 A | 5/1989 | Stauffer et al. | |
| 4,832,048 A | 5/1989 | Cohen | |
| 4,841,988 A | 6/1989 | Fetter et al. | |
| 4,841,990 A | 6/1989 | Kikuchi et al. | |
| 4,881,543 A | 11/1989 | Trembly et al. | |
| 4,891,483 A | 1/1990 | Kikuchi et al. | |
| 4,920,978 A | 5/1990 | Colvin | |
| 4,924,863 A | 5/1990 | Sterzer | |
| 4,924,864 A | 5/1990 | Danzig | |
| 4,932,420 A | 6/1990 | Goldstein | |
| 4,938,217 A | 7/1990 | Lele | |
| 4,945,912 A | 8/1990 | Langberg | |
| 4,960,134 A | 10/1990 | Webster, Jr. | |
| 4,966,597 A | 10/1990 | Cosman | |
| 4,976,711 A | 12/1990 | Parins et al. | |
| 5,007,437 A | 4/1991 | Sterzer | |
| RE33,590 E | 5/1991 | Dory | |
| 5,019,076 A | 5/1991 | Yamanashi et al. | |
| 5,044,375 A | 9/1991 | Bach, Jr. et al. | |
| 5,057,106 A | 10/1991 | Kasevich et al. | |
| 5,078,713 A | 1/1992 | Varney | |
| 5,080,101 A | 1/1992 | Dory | |
| 5,080,102 A | 1/1992 | Dory | |
| 5,085,659 A | 2/1992 | Rydell | |
| 5,097,845 A | 3/1992 | Fetter et al. | |
| 5,100,388 A | 3/1992 | Behl et al. | |
| 5,104,393 A | 4/1992 | Isner et al. | |
| 5,108,390 A | 4/1992 | Potocky et al. | |
| 5,111,822 A | 5/1992 | Dory | |
| 5,114,403 A | 5/1992 | Clarke et al. | |
| 5,129,396 A | 7/1992 | Rosen et al. | |
| 5,139,496 A | 8/1992 | Hed | |
| 5,147,355 A | 9/1992 | Friedman et al. | |
| 5,147,357 A | 9/1992 | Rose et al. | |
| 5,150,717 A | 9/1992 | Rosen et al. | |
| 5,156,151 A | 10/1992 | Imran | |
| 5,158,092 A | 10/1992 | Glace | |
| 5,171,255 A | 12/1992 | Rydell | |
| 5,172,699 A | 12/1992 | Svenson et al. | |
| 5,188,122 A | 2/1993 | Phipps et al. | |
| 5,190,054 A | 3/1993 | Fetter et al. | |
| 5,192,278 A | 3/1993 | Hayes et al. | |
| 5,207,672 A | 5/1993 | Roth et al. | |
| 5,207,674 A | 5/1993 | Hamilton | |
| 5,222,501 A | 6/1993 | Ideker et al. | |
| 5,230,334 A | 7/1993 | Klopotek | |
| 5,230,349 A | 7/1993 | Langberg | |
| 5,242,441 A | 9/1993 | Avitall | |
| 5,246,438 A | 9/1993 | Langberg | |
| 5,248,312 A | 9/1993 | Langberg | |
| 5,263,493 A | 11/1993 | Avitall | |
| 5,281,213 A | 1/1994 | Milder et al. | |
| 5,281,215 A | 1/1994 | Milder | |
| 5,281,217 A | 1/1994 | Edwards et al. | |
| 5,293,869 A | 3/1994 | Edwards et al. | |
| 5,295,484 A | 3/1994 | Marcus et al. | |
| 5,295,955 A | 3/1994 | Rosen et al. | |
| 5,300,068 A | 4/1994 | Rosar et al. | |
| 5,300,099 A | 4/1994 | Rudie | |
| 5,301,687 A | 4/1994 | Wong et al. | |
| 5,304,207 A | 4/1994 | Stromer | |
| 5,313,943 A | 5/1994 | Houser et al. | |
| 5,314,466 A | 5/1994 | Stern et al. | |
| 5,318,525 A | 6/1994 | West et al. | |
| 5,323,781 A | 6/1994 | Ideker et al. | |
| 5,327,889 A | 7/1994 | Imran | |
| 5,334,168 A | 8/1994 | Hemmer | |
| 5,341,807 A | 8/1994 | Nardella | |
| 5,344,431 A | 9/1994 | Merritt et al. | |
| 5,344,441 A | 9/1994 | Gronauer | |
| 5,348,554 A | 9/1994 | Imran et al. | |
| 5,358,515 A | 10/1994 | Hürter et al. | |
| 5,364,336 A | 11/1994 | Carr | |
| 5,364,351 A | 11/1994 | Heinzelman et al. | |
| 5,364,352 A | 11/1994 | Cimino et al. | |
| 5,364,392 A | 11/1994 | Warner et al. | |
| 5,366,490 A | 11/1994 | Edwards et al. | |
| 5,368,592 A | 11/1994 | Stern et al. | |
| 5,369,251 A | 11/1994 | King et al. | |
| 5,370,644 A | 12/1994 | Langberg | |
| 5,370,675 A | 12/1994 | Edwards et al. | |
| 5,370,677 A | 12/1994 | Rudie et al. | |
| 5,370,678 A | 12/1994 | Edwards et al. | |
| 5,374,287 A | 12/1994 | Rubin | |
| 5,376,094 A | 12/1994 | Kline | |
| 5,383,876 A | 1/1995 | Nardella | |
| 5,383,922 A | 1/1995 | Zipes et al. | |
| 5,391,147 A | 2/1995 | Imran et al. | |
| 5,397,304 A | 3/1995 | Truckai | |
| 5,398,683 A | 3/1995 | Edwards et al. | |
| 5,402,772 A | 4/1995 | Moll et al. | |
| 5,403,312 A | 4/1995 | Yates et al. | |
| 5,405,346 A | 4/1995 | Grundy et al. | |
| 5,405,375 A | 4/1995 | Ayers et al. | |
| 5,405,376 A | 4/1995 | Mulier et al. | |
| 5,415,656 A | 5/1995 | Tihon et al. | |
| 5,417,208 A | 5/1995 | Winkler | |
| 5,423,807 A | 6/1995 | Milder | |
| 5,431,649 A | 7/1995 | Mulier et al. | |
| 5,437,665 A | 8/1995 | Munro | |
| 5,439,006 A | 8/1995 | Brennen et al. | |
| 5,443,489 A | 8/1995 | Ben-Haim | |
| 5,445,193 A | 8/1995 | Koeninger et al. | |
| 5,450,846 A | 9/1995 | Goldreyer | |
| 5,452,733 A | 9/1995 | Sterman et al. | |
| 5,454,370 A | 10/1995 | Avitall | |
| 5,454,733 A | 10/1995 | Watanabe et al. | |
| 5,454,807 A | 10/1995 | Lennox et al. | |
| 5,462,544 A | 10/1995 | Saksena et al. | |
| 5,462,545 A | 10/1995 | Wang et al. | |
| 5,464,404 A | 11/1995 | Abela et al. | |
| 5,470,308 A | 11/1995 | Edwards et al. | |
| 5,482,037 A | 1/1996 | Borghi | |
| 5,484,433 A | 1/1996 | Taylor et al. | |
| 5,487,757 A | 1/1996 | Truckai et al. | |

| Patent No. | Date | Inventor |
|---|---|---|
| 5,492,126 A | 2/1996 | Hennige et al. |
| 5,494,039 A | 2/1996 | Onik et al. |
| 5,496,271 A | 3/1996 | Burton et al. |
| 5,496,312 A | 3/1996 | Klicek |
| 5,500,012 A | 3/1996 | Brucker et al. |
| 5,507,743 A | 4/1996 | Edwards et al. .............. 606/41 |
| 5,514,131 A | 5/1996 | Edwards et al. |
| 5,520,188 A | 5/1996 | Hennige et al. |
| 5,529,820 A | 6/1996 | Nomi et al. |
| 5,531,677 A * | 7/1996 | Lundquist et al. ............ 604/22 |
| 5,536,247 A | 7/1996 | Thornton |
| 5,540,681 A | 7/1996 | Strul et al. |
| 5,540,684 A | 7/1996 | Hassler, Jr. |
| 5,545,193 A | 8/1996 | Fleischman et al. |
| 5,545,200 A | 8/1996 | West et al. |
| 5,549,638 A | 8/1996 | Burdette |
| 5,549,644 A | 8/1996 | Lundquist et al. |
| 5,549,661 A | 8/1996 | Kordis et al. |
| 5,569,242 A | 10/1996 | Lax et al. |
| 5,571,088 A | 11/1996 | Lennox et al. |
| 5,571,215 A | 11/1996 | Sterman et al. |
| 5,575,766 A | 11/1996 | Swartz et al. |
| 5,575,810 A | 11/1996 | Swanson et al. |
| 5,578,030 A | 11/1996 | Levin |
| 5,578,067 A | 11/1996 | Ekwall et al. |
| 5,581,905 A | 12/1996 | Huelsman et al. |
| 5,584,830 A | 12/1996 | Ladd et al. |
| 5,590,657 A | 1/1997 | Cain et al. |
| 5,593,404 A | 1/1997 | Costello et al. |
| 5,593,405 A | 1/1997 | Osypka |
| 5,599,295 A | 2/1997 | Rosen et al. |
| 5,599,346 A | 2/1997 | Baker et al. |
| 5,603,697 A | 2/1997 | Grundy et al. |
| 5,606,974 A | 3/1997 | Castellano et al. |
| 5,607,389 A | 3/1997 | Edwards et al. |
| 5,628,771 A | 5/1997 | Mizukawa et al. |
| 5,630,837 A | 5/1997 | Crowley |
| 5,640,955 A | 6/1997 | Ockuly et al. |
| 5,643,255 A | 7/1997 | Organ |
| 5,658,280 A | 8/1997 | Issa |
| 5,672,172 A | 9/1997 | Zupkas |
| 5,672,174 A | 9/1997 | Gough et al. |
| 5,673,694 A | 10/1997 | Rivers |
| 5,673,695 A | 10/1997 | McGee et al. |
| 5,676,692 A | 10/1997 | Sanghvi et al. |
| 5,676,693 A | 10/1997 | LaFontaine |
| 5,681,308 A | 10/1997 | Edwards et al. |
| 5,683,382 A | 11/1997 | Lenihan et al. |
| 5,683,384 A | 11/1997 | Gough et al. |
| 5,687,723 A | 11/1997 | Avitall |
| 5,688,267 A | 11/1997 | Panescu et al. |
| 5,693,078 A | 12/1997 | Desai et al. |
| 5,693,082 A | 12/1997 | Warner et al. |
| 5,694,701 A | 12/1997 | Huelsman et al. |
| 5,697,928 A | 12/1997 | Walcott et al. |
| 5,707,369 A | 1/1998 | Vaitekunas et al. |
| 5,718,226 A | 2/1998 | Riza |
| 5,718,241 A | 2/1998 | Ben-Haim et al. |
| 5,720,718 A | 2/1998 | Rosen et al. |
| 5,720,775 A | 2/1998 | Larnard |
| 5,725,523 A | 3/1998 | Mueller |
| 5,730,127 A | 3/1998 | Avitall |
| 5,733,280 A | 3/1998 | Avitall |
| 5,733,281 A | 3/1998 | Nardella |
| 5,735,280 A | 4/1998 | Sherman et al. |
| 5,737,384 A | 4/1998 | Fenn ........................... 378/65 |
| 5,738,096 A | 4/1998 | Ben-Haim |
| 5,741,225 A | 4/1998 | Lax et al. .................... 604/22 |
| 5,741,249 A | 4/1998 | Moss et al. |
| 5,743,239 A | 4/1998 | Iwase |
| 5,755,760 A | 5/1998 | Maguire et al. |
| 5,762,066 A | 6/1998 | Law et al. |
| 5,762,626 A | 6/1998 | Lundquist et al. |
| 5,769,790 A | 6/1998 | Watkins et al. |
| 5,769,846 A | 6/1998 | Edwards et al. |
| 5,782,747 A | 7/1998 | Zimmon |
| 5,782,828 A | 7/1998 | Chen et al. |
| 5,785,706 A | 7/1998 | Bednarek |
| 5,785,707 A | 7/1998 | Boyd et al. |
| 5,788,692 A | 8/1998 | Campbell et al. |
| 5,797,905 A | 8/1998 | Fleischman et al. |
| 5,797,960 A | 8/1998 | Stevens et al. |
| 5,800,378 A | 9/1998 | Edwards et al. |
| 5,800,379 A | 9/1998 | Edwards |
| 5,800,413 A | 9/1998 | Swartz et al. |
| 5,800,428 A | 9/1998 | Nelson et al. |
| 5,800,482 A | 9/1998 | Pomeranz et al. |
| 5,800,494 A | 9/1998 | Campbell et al. |
| 5,807,309 A | 9/1998 | Lundquist et al. |
| 5,807,395 A | 9/1998 | Mulier et al. |
| 5,810,803 A | 9/1998 | Moss et al. |
| 5,814,028 A | 9/1998 | Swartz et al. |
| 5,823,197 A | 10/1998 | Edwards |
| 5,823,955 A | 10/1998 | Kuck et al. |
| 5,823,956 A | 10/1998 | Roth et al. |
| 5,823,962 A | 10/1998 | Schaetzle et al. |
| 5,826,576 A | 10/1998 | West |
| 5,827,216 A | 10/1998 | Igo et al. |
| 5,829,447 A | 11/1998 | Stevens et al. |
| 5,836,947 A | 11/1998 | Fleischman et al. |
| 5,836,990 A | 11/1998 | Li |
| 5,840,027 A | 11/1998 | Swartz et al. |
| 5,840,030 A | 11/1998 | Ferek-Petric et al. |
| 5,842,037 A | 11/1998 | Haartsen |
| 5,843,026 A | 12/1998 | Edwards et al. |
| 5,843,075 A | 12/1998 | Taylor |
| 5,843,171 A | 12/1998 | Campbell et al. |
| 5,846,238 A | 12/1998 | Jackson et al. |
| 5,852,860 A | 12/1998 | Lorraine et al. |
| 5,853,366 A | 12/1998 | Dowlatshahi |
| 5,853,368 A | 12/1998 | Solomon et al. |
| 5,855,614 A | 1/1999 | Stevens et al. |
| 5,860,920 A | 1/1999 | McGee et al. |
| 5,861,002 A | 1/1999 | Desai |
| 5,861,021 A | 1/1999 | Thome et al. |
| 5,863,290 A * | 1/1999 | Gough et al. ................. 606/41 |
| 5,868,737 A | 2/1999 | Taylor et al. |
| 5,871,481 A | 2/1999 | Kannenberg et al. |
| 5,871,525 A | 2/1999 | Edwards et al. |
| 5,873,828 A | 2/1999 | Fujio et al. |
| 5,873,896 A | 2/1999 | Ideker |
| 5,882,302 A | 3/1999 | Driscoll, Jr. et al. |
| 5,885,278 A | 3/1999 | Fleischman |
| 5,895,355 A | 4/1999 | Schaer |
| 5,897,553 A | 4/1999 | Mulier et al. |
| 5,897,554 A | 4/1999 | Chia et al. |
| 5,899,899 A | 5/1999 | Arless et al. |
| 5,904,709 A | 5/1999 | Arndt et al. |
| 5,906,580 A | 5/1999 | Kline-Schoder et al. |
| 5,910,129 A | 6/1999 | Koblish et al. |
| 5,916,213 A | 6/1999 | Haissaguerre et al. |
| 5,919,188 A | 7/1999 | Shearon et al. |
| 5,921,924 A | 7/1999 | Avitall |
| 5,924,424 A | 7/1999 | Stevens et al. |
| 5,931,810 A | 8/1999 | Grabek |
| 5,938,600 A | 8/1999 | Van Vaals et al. |
| 5,938,612 A | 8/1999 | Kline-Schoder et al. |
| 5,938,692 A | 8/1999 | Rudie |
| 5,954,662 A | 9/1999 | Swanson et al. |
| 5,954,665 A | 9/1999 | Ben-Haim |
| 5,957,842 A | 9/1999 | Littmann et al. |
| 5,957,969 A | 9/1999 | Warner et al. |
| 5,964,727 A | 10/1999 | Edwards et al. |
| 5,964,732 A | 10/1999 | Willard |
| 5,964,756 A | 10/1999 | McGaffigan et al. |
| 5,971,983 A | 10/1999 | Lesh |

| Patent | Date | Inventor |
|---|---|---|
| 5,978,714 A | 11/1999 | Zadini et al. |
| 5,980,697 A | 11/1999 | Kolb et al. |
| 5,993,389 A | 11/1999 | Driscoll, Jr. et al. |
| 5,993,445 A | 11/1999 | Issa |
| 5,993,447 A | 11/1999 | Blewett et al. |
| 5,995,875 A | 11/1999 | Blewett et al. |
| 6,002,955 A | 12/1999 | Willems et al. |
| 6,004,269 A | 12/1999 | Crowley et al. |
| 6,007,499 A | 12/1999 | Martin et al. |
| 6,010,516 A | 1/2000 | Hulka |
| 6,012,457 A | 1/2000 | Lesh |
| 6,016,811 A | 1/2000 | Knopp et al. |
| 6,016,848 A | 1/2000 | Egres, Jr. |
| 6,024,740 A | 2/2000 | Lesh et al. |
| 6,027,497 A | 2/2000 | Daniel et al. |
| 6,027,501 A | 2/2000 | Goble et al. |
| 6,030,382 A | 2/2000 | Fleischman et al. |
| 6,032,077 A | 2/2000 | Pomeranz |
| 6,056,735 A | 5/2000 | Okada et al. |
| 6,059,778 A | 5/2000 | Sherman |
| 6,063,077 A | 5/2000 | Schaer |
| 6,063,081 A | 5/2000 | Mulier et al. |
| 6,064,902 A | 5/2000 | Haissaguerre et al. |
| 6,066,094 A | 5/2000 | Ben-Haim |
| 6,068,628 A | 5/2000 | Fanton et al. |
| 6,068,629 A | 5/2000 | Haissaguerre et al. |
| 6,071,274 A | 6/2000 | Thompson et al. |
| 6,071,281 A | 6/2000 | Burnside et al. |
| 6,076,012 A | 6/2000 | Swanson et al. |
| 6,083,159 A | 7/2000 | Driscoll, Jr. et al. |
| 6,086,583 A | 7/2000 | Ouchi |
| 6,090,105 A * | 7/2000 | Zepeda et al. ........... 606/41 |
| 6,097,985 A | 8/2000 | Kasevich et al. |
| 6,102,886 A | 8/2000 | Lundquist et al. ........... 604/22 |
| 6,106,517 A | 8/2000 | Zupkas |
| 6,106,521 A | 8/2000 | Blewett et al. |
| 6,106,522 A | 8/2000 | Fleischman et al. |
| 6,106,524 A | 8/2000 | Eggers et al. |
| 6,117,101 A | 9/2000 | Diederich et al. |
| 6,119,041 A | 9/2000 | Pomeranz et al. |
| 6,126,682 A * | 10/2000 | Sharkey et al. ........... 607/96 |
| 6,135,971 A | 10/2000 | Hutchinson et al. |
| 6,142,994 A | 11/2000 | Swanson et al. |
| 6,146,378 A | 11/2000 | Mukus et al. |
| 6,146,379 A | 11/2000 | Fleischman et al. |
| 6,152,920 A | 11/2000 | Thompson et al. |
| 6,161,543 A | 12/2000 | Cox et al. |
| 6,162,216 A * | 12/2000 | Guziak et al. ........... 606/34 |
| 6,164,283 A | 12/2000 | Lesh |
| 6,165,174 A | 12/2000 | Jacobs et al. |
| 6,171,303 B1 | 1/2001 | Ben-Haim et al. |
| 6,174,309 B1 | 1/2001 | Wrublewski et al. |
| 6,178,354 B1 | 1/2001 | Gibson |
| 6,182,664 B1 | 2/2001 | Cosgrove |
| 6,190,382 B1 | 2/2001 | Ormsby et al. |
| 6,200,315 B1 | 3/2001 | Gaiser et al. |
| 6,206,831 B1 | 3/2001 | Suorsa et al. |
| 6,210,356 B1 | 4/2001 | Anderson et al. |
| 6,216,027 B1 | 4/2001 | Willis et al. |
| 6,217,530 B1 | 4/2001 | Martin et al. |
| 6,217,573 B1 | 4/2001 | Webster |
| 6,224,587 B1 | 5/2001 | Gibson |
| 6,231,518 B1 | 5/2001 | Grabek et al. |
| 6,233,490 B1 | 5/2001 | Kasevich |
| 6,235,025 B1 | 5/2001 | Swartz et al. |
| 6,235,796 B1 | 5/2001 | Niazi |
| 6,237,605 B1 | 5/2001 | Vaska et al. |
| 6,241,722 B1 | 6/2001 | Dobak et al. |
| 6,241,728 B1 | 6/2001 | Gaiser et al. |
| 6,241,754 B1 | 6/2001 | Swanson et al. |
| 6,245,062 B1 | 6/2001 | Berube et al. |
| 6,251,128 B1 | 6/2001 | Knopp et al. |
| 6,273,887 B1 | 8/2001 | Yamauchi et al. |
| 6,277,113 B1 | 8/2001 | Berube |
| 6,283,955 B1 | 9/2001 | Pacala et al. |
| 6,287,302 B1 | 9/2001 | Berube |
| 6,289,249 B1 | 9/2001 | Arndt et al. |
| 6,290,699 B1 | 9/2001 | Hall et al. |
| 6,302,880 B1 | 10/2001 | Schaer |
| 6,306,124 B1 | 10/2001 | Jones et al. |
| 6,306,132 B1 | 10/2001 | Moorman et al. |
| 6,309,388 B1 | 10/2001 | Fowler |
| 6,311,692 B1 | 11/2001 | Vaska et al. |
| 6,312,425 B1 | 11/2001 | Simpson et al. |
| 6,312,427 B1 | 11/2001 | Berube et al. |
| 6,314,962 B1 | 11/2001 | Vaska et al. |
| 6,314,963 B1 | 11/2001 | Vaska et al. |
| 6,315,741 B1 | 11/2001 | Martin et al. |
| 6,322,558 B1 | 11/2001 | Taylor et al. |
| 6,325,796 B1 * | 12/2001 | Berube et al. ........... 606/33 |
| 6,325,797 B1 | 12/2001 | Stewart et al. |
| 6,332,881 B1 | 12/2001 | Carner et al. |
| 6,346,104 B2 | 2/2002 | Daly et al. |
| 6,355,033 B1 * | 3/2002 | Moorman et al. ........... 606/33 |
| 6,356,790 B1 | 3/2002 | Maguire et al. |
| 6,358,248 B1 | 3/2002 | Mulier et al. |
| 6,361,531 B1 | 3/2002 | Hissong |
| 6,364,876 B1 | 4/2002 | Erb et al. |
| 6,379,348 B1 | 4/2002 | Onik |
| 6,383,182 B1 | 5/2002 | Berube et al. |
| 6,402,556 B1 | 6/2002 | Lang et al. |
| 6,413,254 B1 | 7/2002 | Hissong et al. |
| 6,423,057 B1 | 7/2002 | He et al. |
| 6,423,059 B1 | 7/2002 | Hanson et al. |
| 6,428,538 B1 | 8/2002 | Blewett et al. |
| 6,430,426 B2 | 8/2002 | Avitall |
| 6,432,067 B1 | 8/2002 | Martin et al. |
| 6,432,069 B1 | 8/2002 | Godo et al. |
| 6,433,464 B2 | 8/2002 | Jones |
| 6,454,758 B1 | 9/2002 | Thompson et al. |
| 6,461,314 B1 | 10/2002 | Pant et al. |
| 6,464,700 B1 | 10/2002 | Koblish et al. |
| 6,467,138 B1 | 10/2002 | Aimé |
| 6,471,696 B1 | 10/2002 | Berube et al. |
| 6,471,697 B1 | 10/2002 | Lesh |
| 6,474,340 B1 | 11/2002 | Vaska et al. |
| 6,484,727 B1 | 11/2002 | Vaska et al. |
| 6,488,639 B1 | 12/2002 | Ribault et al. |
| 6,488,679 B1 | 12/2002 | Swanson et al. |
| 6,488,680 B1 | 12/2002 | Francischelli et al. |
| 6,490,474 B1 | 12/2002 | Willis et al. |
| 6,500,133 B2 | 12/2002 | Martin et al. |
| 6,502,575 B1 | 1/2003 | Jacobs et al. |
| 6,508,774 B1 | 1/2003 | Acker et al. |
| 6,511,478 B1 | 1/2003 | Burnside et al. |
| 6,514,246 B1 | 2/2003 | Swanson et al. |
| 6,514,249 B1 | 2/2003 | Maguire et al. |
| 6,517,536 B2 | 2/2003 | Hooven et al. |
| 6,526,320 B2 | 2/2003 | Mitchell |
| 6,527,767 B2 | 3/2003 | Wang et al. |
| 6,527,768 B2 | 3/2003 | Berube |
| 6,529,756 B1 | 3/2003 | Phan et al. |
| 6,533,780 B1 * | 3/2003 | Laird et al. ........... 606/41 |
| 6,542,781 B1 | 4/2003 | Koblish et al. |
| 6,546,935 B2 | 4/2003 | Hooven |
| 6,576,875 B1 | 6/2003 | Kleffner et al. |
| 6,584,360 B2 | 6/2003 | Francischelli et al. |
| 6,586,040 B1 | 7/2003 | Von Falkenhausen |
| 6,610,055 B1 | 8/2003 | Swanson et al. |
| 6,645,200 B1 | 11/2003 | Koblish et al. |
| 6,645,202 B1 | 11/2003 | Pless et al. |
| 6,652,513 B2 | 11/2003 | Panescu et al. |
| 6,663,622 B1 | 12/2003 | Foley et al. |
| 6,673,068 B1 | 1/2004 | Berube |
| 6,689,062 B1 | 2/2004 | Mesallum |
| 6,689,128 B2 | 2/2004 | Sliwa, Jr. et al. |

| | | |
|---|---|---|
| 6,692,491 B1 | 2/2004 | Phan |
| 6,701,931 B2 | 3/2004 | Sliwa, Jr. et al. |
| 6,706,038 B2 | 3/2004 | Francischelli et al. |
| 6,719,755 B2 | 4/2004 | Sliwa, Jr. et al. |
| 6,802,840 B2 | 10/2004 | Fatt et al. |
| 6,805,709 B1 | 10/2004 | Schaldach et al. |
| 6,808,484 B1 | 10/2004 | Peters et al. |
| 6,808,529 B2 | 10/2004 | Fulkerson |
| 6,808,536 B2 | 10/2004 | Wright et al. |
| 2001/0031961 A1 | 10/2001 | Hooven |
| 2002/0017306 A1 | 2/2002 | Cox et al. |
| 2002/0032440 A1 | 3/2002 | Hooven et al. |
| 2002/0042610 A1 | 4/2002 | Sliwa, Jr. et al. |
| 2002/0042611 A1 | 4/2002 | Sliwa et al. |
| 2002/0045895 A1 | 4/2002 | Sliwa, Jr. et al. |
| 2002/0087151 A1 | 7/2002 | Mody et al. |
| 2002/0087157 A1 | 7/2002 | Sliwa, Jr. et al. |
| 2002/0091382 A1 | 7/2002 | Hooven |
| 2002/0091383 A1 | 7/2002 | Hooven |
| 2002/0091384 A1 | 7/2002 | Hooven et al. |
| 2002/0095145 A1 | 7/2002 | Holzapfel et al. |
| 2002/0103484 A1 | 8/2002 | Hooven |
| 2002/0107513 A1 | 8/2002 | Hooven |
| 2002/0107514 A1 | 8/2002 | Hooven |
| 2002/0111613 A1 | 8/2002 | Berube |
| 2002/0115993 A1 | 8/2002 | Hooven |
| 2002/0120263 A1 | 8/2002 | Brown et al. |
| 2002/0120267 A1 | 8/2002 | Phan |
| 2002/0120316 A1 | 8/2002 | Hooven et al. |
| 2002/0128639 A1 | 9/2002 | Pless et al. |
| 2002/0128642 A1 | 9/2002 | Berube et al. |
| 2002/0173784 A1 | 11/2002 | Sliwa, Jr. et al. |
| 2002/0193783 A1 | 12/2002 | Gauthier et al. |
| 2002/0193786 A1 | 12/2002 | Berube et al. |
| 2003/0024537 A1 | 2/2003 | Cox et al. |
| 2003/0028187 A1 | 2/2003 | Vaska et al. |
| 2003/0029462 A1 | 2/2003 | Cox et al. |
| 2003/0032952 A1 | 2/2003 | Hooven |
| 2003/0050630 A1 | 3/2003 | Mody et al. |
| 2003/0050631 A1 | 3/2003 | Mody et al. |
| 2003/0065327 A1 | 4/2003 | Wellman et al. |
| 2003/0069572 A1 | 4/2003 | Wellman et al. |
| 2003/0069574 A1 | 4/2003 | Sliwa, Jr. et al. |
| 2003/0069575 A1 | 4/2003 | Fatt et al. |
| 2003/0069577 A1 | 4/2003 | Vaska et al. |
| 2003/0073988 A1 | 4/2003 | Berube et al. |
| 2003/0073992 A1 | 4/2003 | Sliwa, Jr. et al. |
| 2003/0078571 A1 | 4/2003 | Sliwa, Jr. et al. |
| 2003/0079753 A1 | 5/2003 | Vaska et al. |
| 2003/0083654 A1 | 5/2003 | Fatt et al. |
| 2003/0093068 A1 | 5/2003 | Hooven |
| 2003/0097126 A1 | 5/2003 | Woloszko et al. |
| 2003/0109868 A1 | 6/2003 | Fatt et al. |
| 2003/0125666 A1 | 7/2003 | Kasahara et al. |
| 2003/0125725 A1 | 7/2003 | Woodard et al. |
| 2003/0125729 A1 | 7/2003 | Hooven et al. |
| 2003/0136951 A1 | 7/2003 | Hung |
| 2003/0158547 A1 | 8/2003 | Phan |
| 2003/0158548 A1 | 8/2003 | Phan et al. |
| 2003/0163128 A1 | 8/2003 | Patil et al. |
| 2003/0171745 A1 | 9/2003 | Francischelli et al. |
| 2003/0176764 A1 | 9/2003 | Fiegel et al. |
| 2003/0181907 A1 | 9/2003 | Lindsay |
| 2004/0002045 A1 | 1/2004 | Wellman et al. |
| 2004/0044340 A1 | 3/2004 | Francischelli et al. |
| 2004/0049179 A1 | 3/2004 | Francischelli et al. |
| 2004/0049208 A1 | 3/2004 | Hill et al. |
| 2004/0068274 A1 | 4/2004 | Hooven |
| 2004/0092990 A1 | 5/2004 | Opie et al. |
| 2004/0106918 A1 | 6/2004 | Cox et al. |

FOREIGN PATENT DOCUMENTS

| | | |
|---|---|---|
| EP | 0358 336 A1 | 3/1990 |
| EP | 0628322 A2 | 12/1994 |
| EP | 0655 225 B1 | 3/2000 |
| EP | 0738501 B1 | 5/2000 |
| EP | 1005838 A1 | 6/2000 |
| EP | 1042990 A1 | 10/2000 |
| EP | 1118310 A1 | 7/2001 |
| EP | 0839547 B1 | 9/2003 |
| WO | WO93/08757 | 5/1993 |
| WO | WO93/15664 | 8/1993 |
| WO | WO 93/20768 | 10/1993 |
| WO | WO93/20893 | 10/1993 |
| WO | WO 93/24065 | 12/1993 |
| WO | WO94/02204 | 2/1994 |
| WO | WO 95/05212 | 2/1995 |
| WO | WO 95/18575 | 7/1995 |
| WO | WO 96/26675 | 9/1996 |
| WO | WO 96/35469 A1 | 11/1996 |
| WO | WO 97/44092 A | 11/1997 |
| WO | WO98/06341 | 2/1998 |
| WO | 98/17185 | 4/1998 |
| WO | 98/17187 | 4/1998 |
| WO | 98/44857 | 10/1998 |
| WO | 99/08613 | 2/1999 |
| WO | WO 99/04696 | 2/1999 |
| WO | 99/34860 | 7/1999 |
| WO | WO 99/59486 | 11/1999 |
| WO | WO 00/16850 | 3/2000 |
| WO | WO00/24463 | 5/2000 |
| WO | WO00/56239 | 9/2000 |
| WO | WO02/38052 A2 | 5/2002 |

OTHER PUBLICATIONS

"Biopsy Needles Liver, Kidney and Soft Tissue Biopsy Menghini Technique Aspirating Needle Set", Popper & Sons, Inc., Biomedical Instrument Division.

Andriole et al., "Biopsy Needle Characteristics Assessed in the Laboratory," Radiology, vol. 148, No. 3, Sep. 1983, pp. 659-662.

Arendt-Nielsen et al., "Selectivity of Spatial Filters for Surface EMG Detection from the Tibialis Anterior Muscle," [online], © 2000 [retrieved Nov. 23, 2003], 2 pages, Retrieved from the Internet: <URL:http://www.lisin.polito.it/english/annual_reports/ar2002_uk/19uk.htm.

Cheng, "Field and Wave Electromagnetics," 1989, Addison Wesley Publishing Co., Inc., pp. 485-509.

Cox, "The Surgical Treatment of Atrial Fibrillation IV Surgical Technique," J. Thorac Cardiovasc. Surg. 101, 1991, pp. 584-592.

Durney et al., "Antennas for Medical Applications" Chapter 24, pp. 24-2, 24-27, 24-28, 24-29 and 24-58.

Gottlieb et al., "Interstitial Microwave Hyperthermia Applicators Having Submillimetre Diameters," Int. J. Hyperthermia, vol. 6, No. 3, 1990, pp. 707-714.

Haines et al., "Tissue Heating During Radiofrequency Catheter Ablation: A Thermodynamic Model and Observation in Isolated Perfused and Superfused Canine Right Ventricular Free Wall," Pacint Clin Electrophysol, Jun. 1989, 12(6), pp. 962-976.

Liem et al., "Microwave Linear Ablation of the Isthmus Between the Inferior Vena Cava and Tricuspid Annulus," Pace, vol. 21, Nov. 1998, pp. 2079-2086.

Matsukawa et al., "Percutaneous Microwave Coagulation Therapy In Liver Tumors: A 3-Year Experience," Acta Radiologica, vol. 38, 1997, pp. 410-415.

Seki et al., "Ultrasonically Guided Percutaneous Microwave Coagulation Therapy for Small Hepatocellular Carcinoma," Cancer, vol. 74, No. 3, Aug. 1, 1994, pp. 817-825.

European Search Report from Corresponding EP Application 01307788.8, mailed Nov. 28, 2003.

* cited by examiner

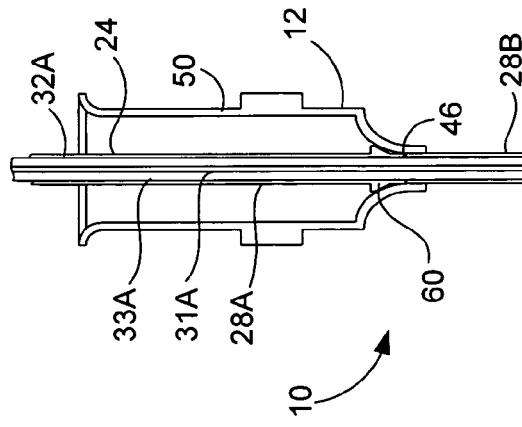
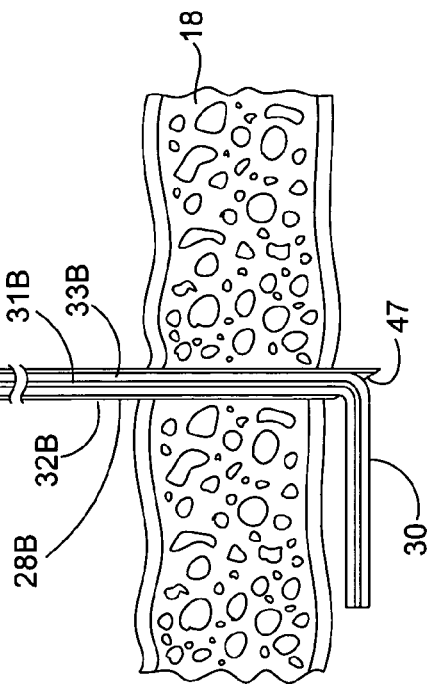
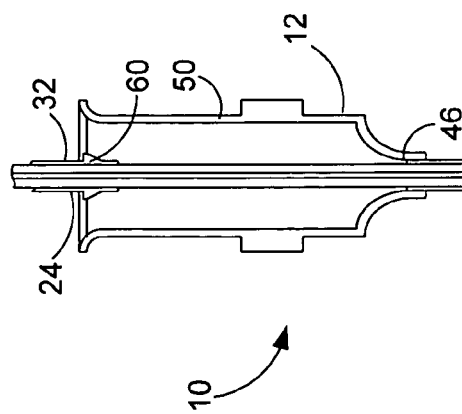
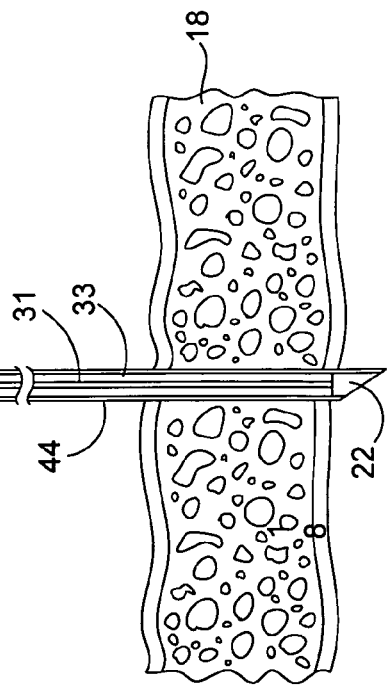
FIG. 12A
FIG. 12B

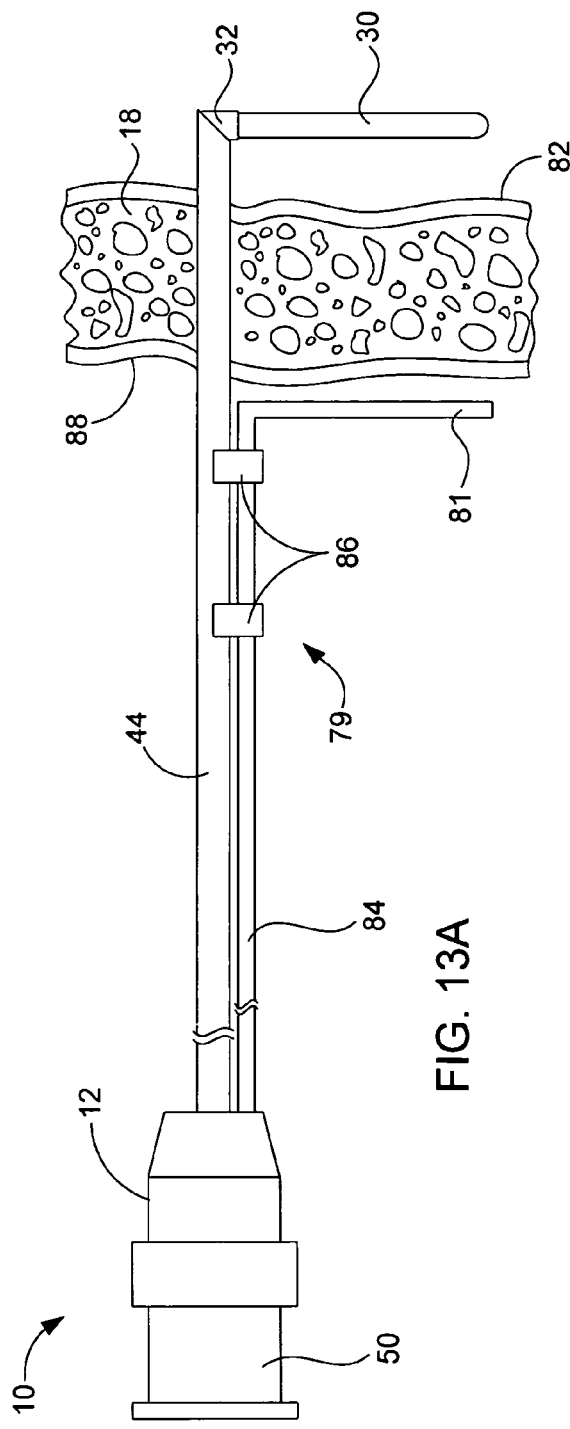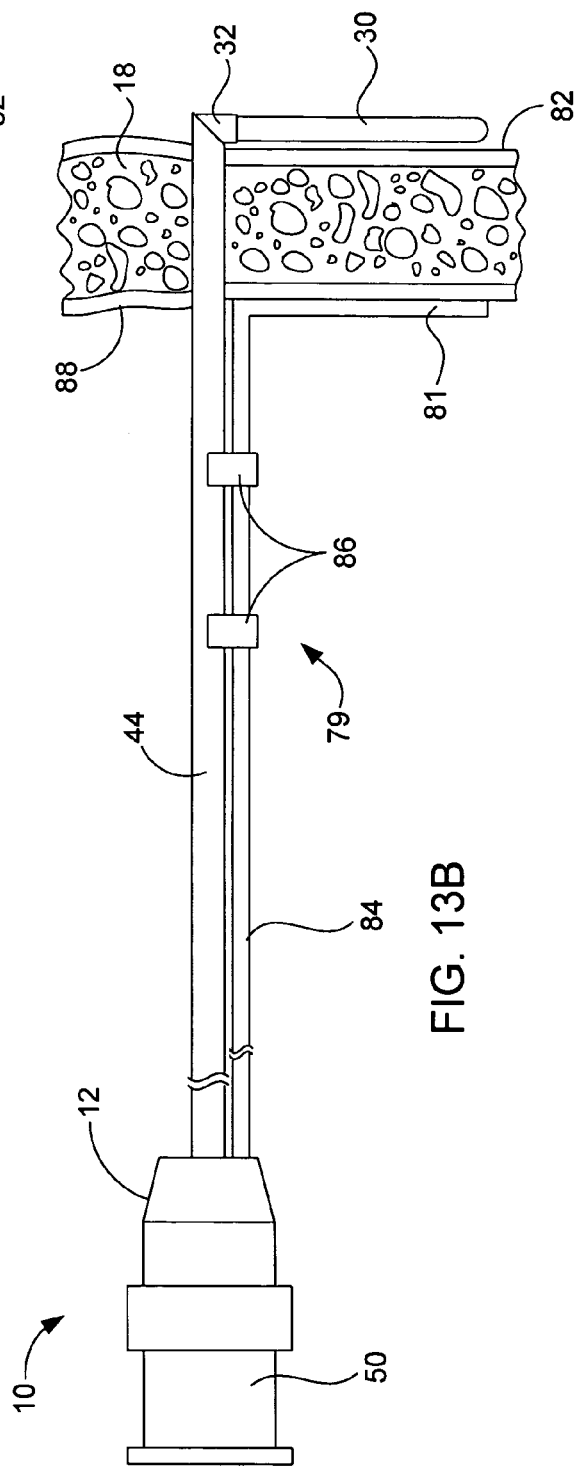

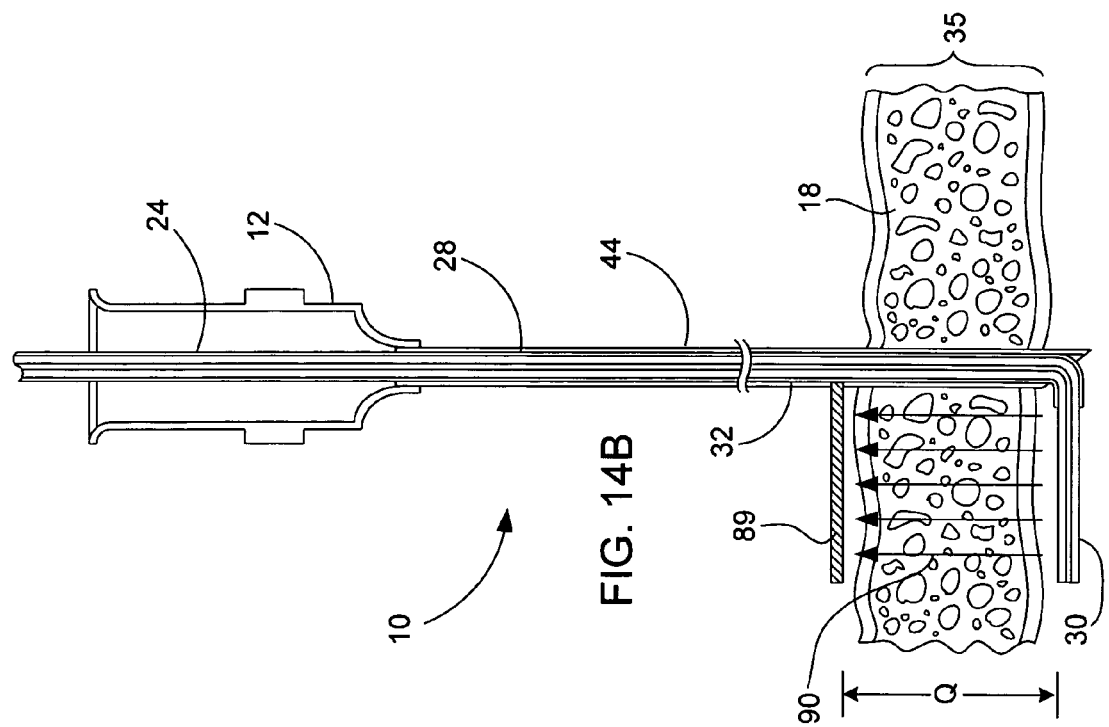
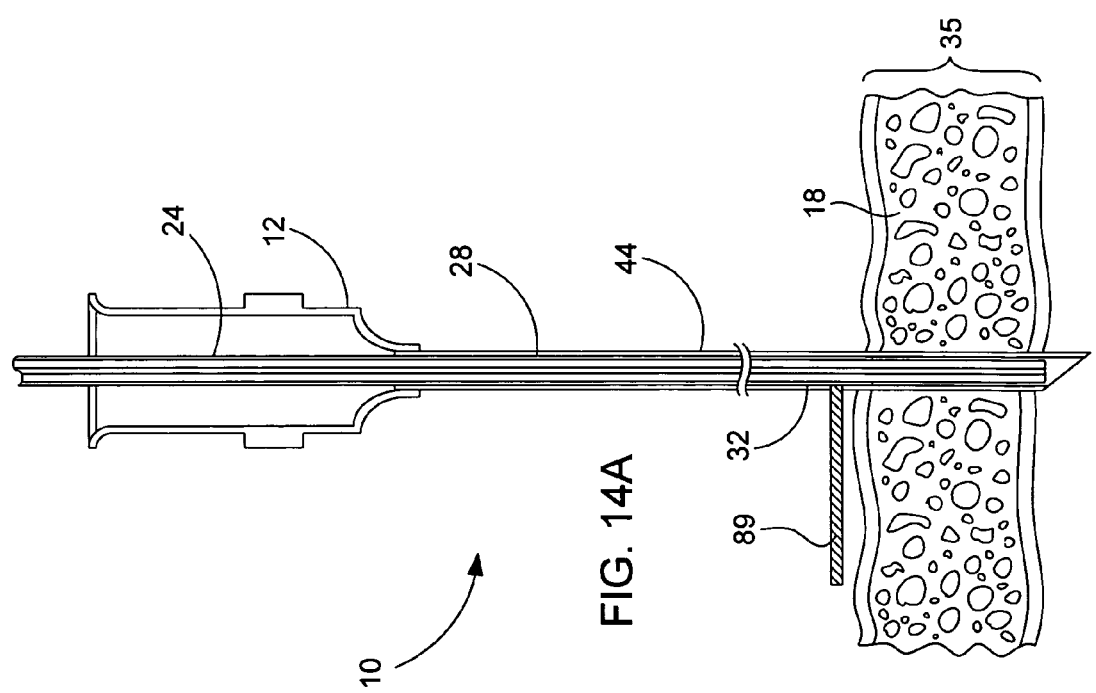

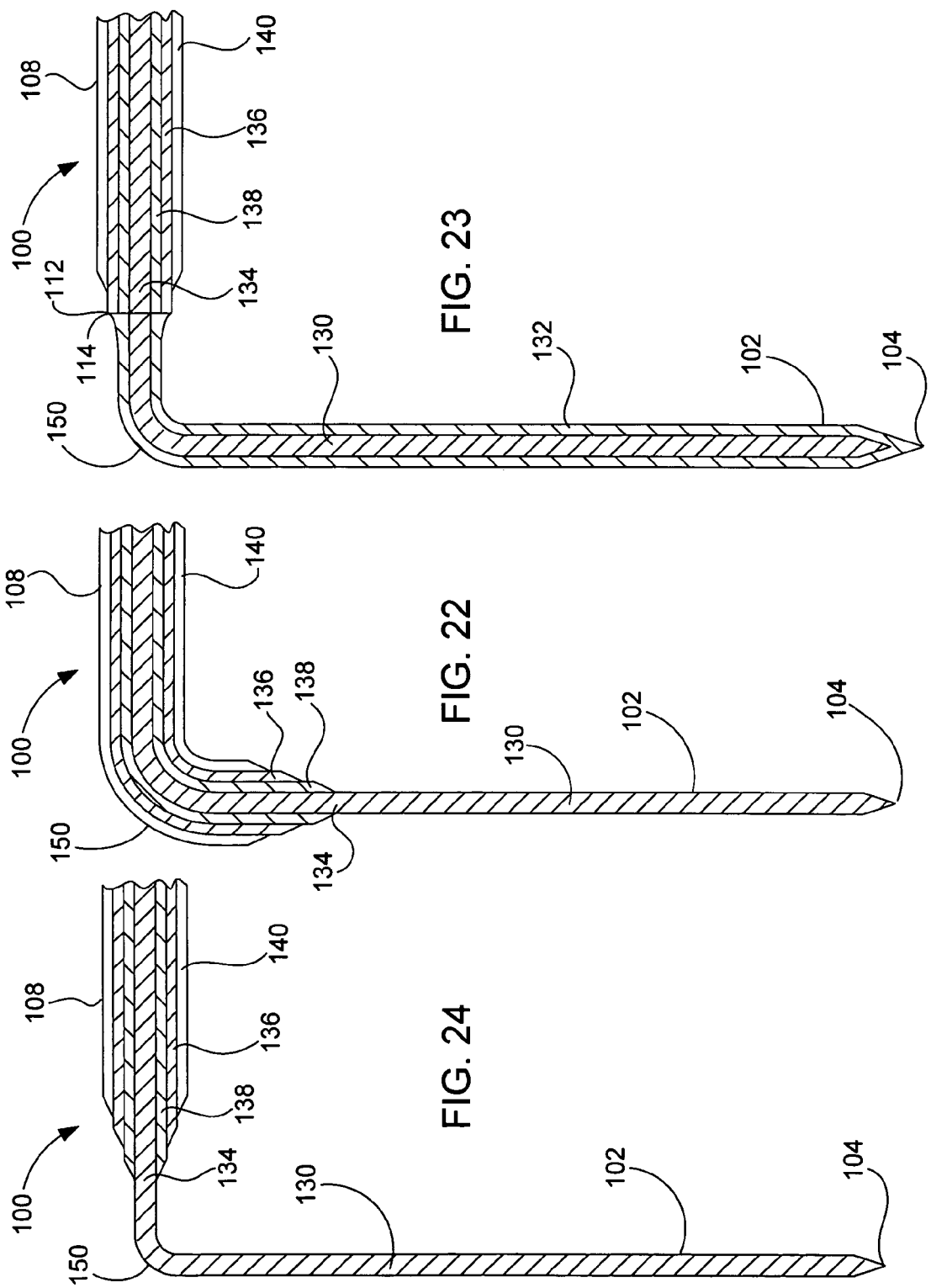

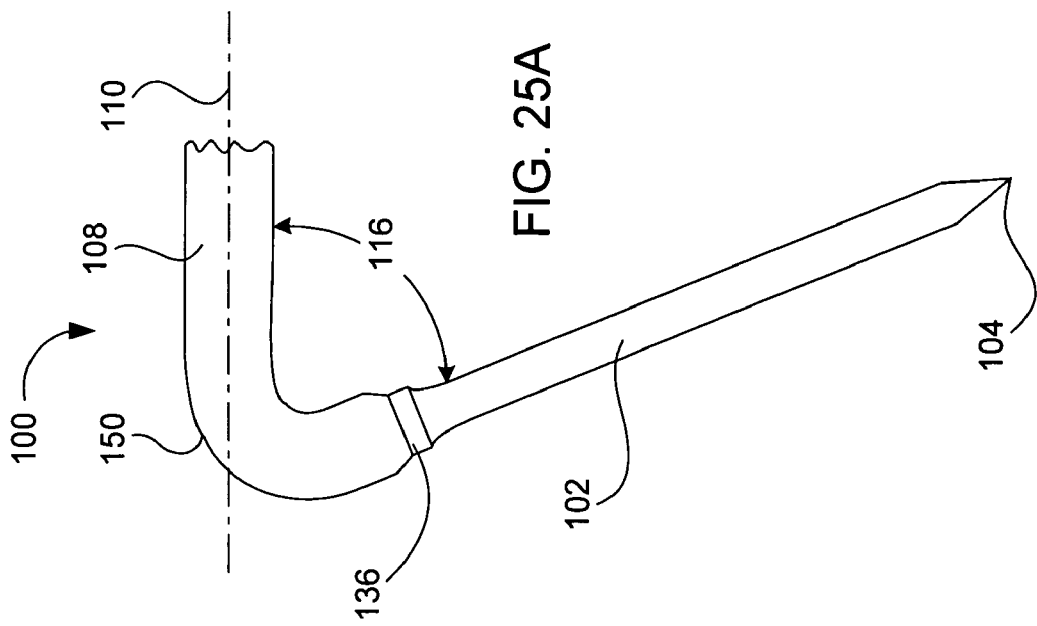
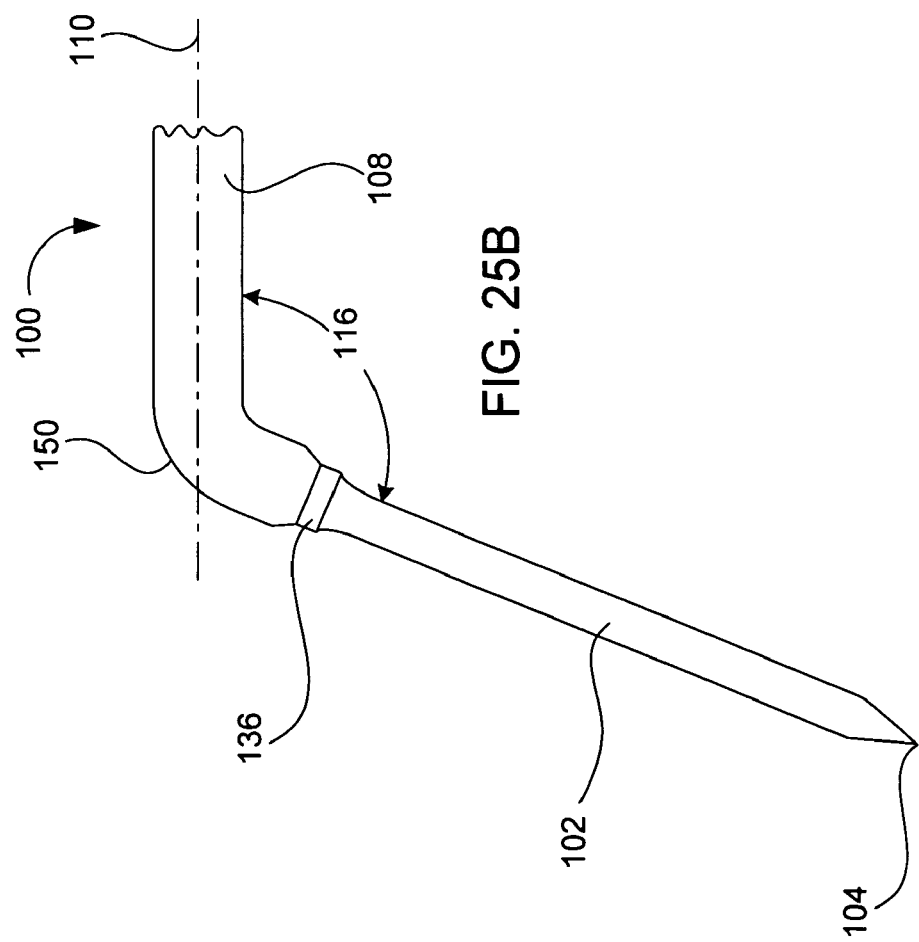

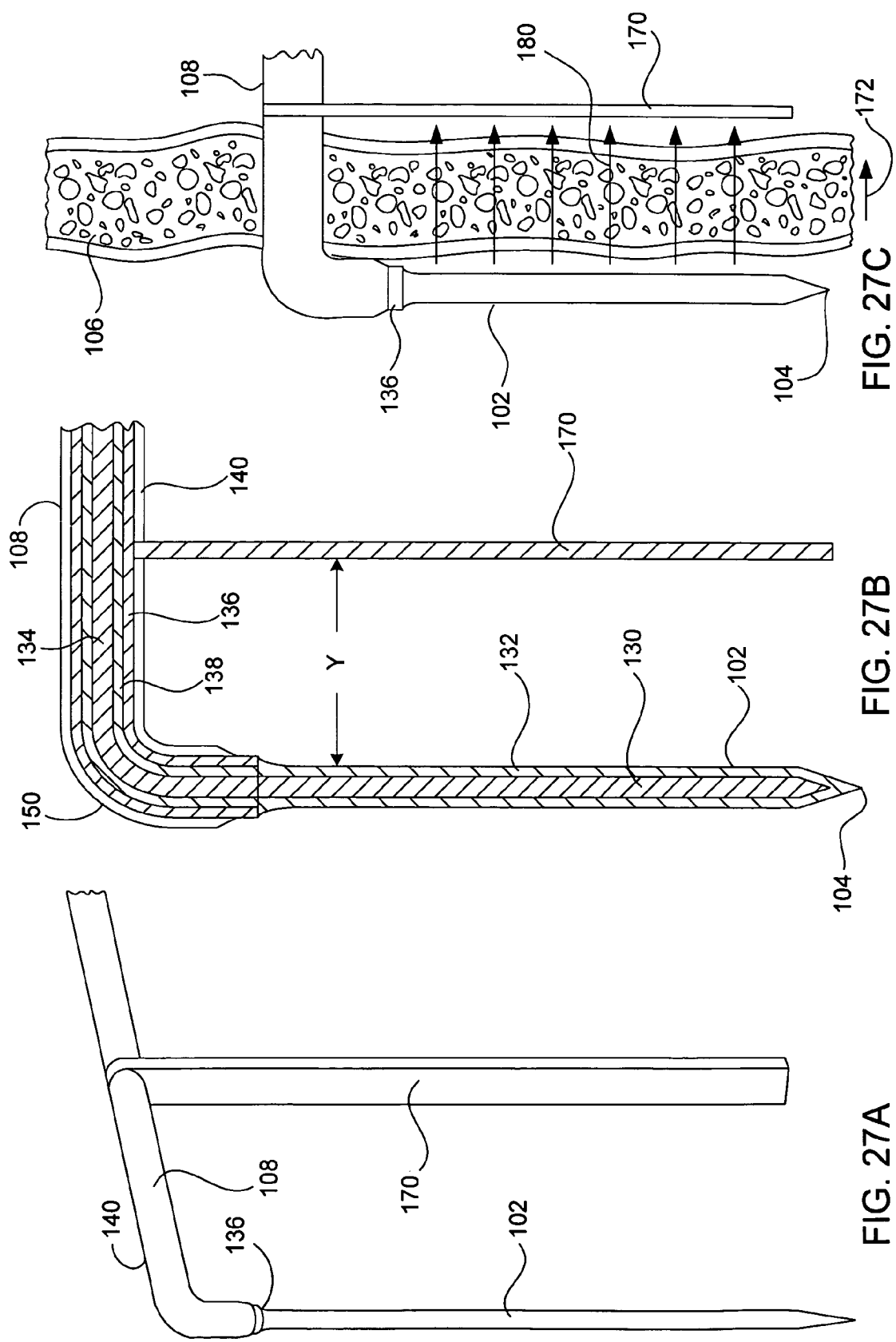

SURGICAL MICROWAVE ABLATION ASSEMBLY

CROSS REFERENCE TO RELATED APPLICATION

This application is a continuation-in-part of U.S. patent application Ser. No. 09/305,143, filed on May 4, 1999, now U.S. Pat. No. 6,325,796, which is herein incorporated by reference.

BACKGROUND OF THE INVENTION

The present invention relates to apparatus and methods for ablating biological tissues. More particularly, the present invention relates to improved ablation devices that are capable of penetrating through bodily organs.

Since their introduction at the end of the 80's, medical ablation devices have become a standard tool for surgeons and electrophysiologists. For example, ablation devices utilizing DC shock, radio frequency (RF) current, ultrasound, microwave, direct heat, cryothermy or lasers have been introduced and employed to various degrees to ablate biological tissues. In some ablation procedures, however, the ablation of the targeted tissues may be difficult because of their location or the presence of physiological obstacle. For example, in some coronary applications where the ablation lines are done epicardially, the epicardium may be covered by layers of fat that can prohibit the lesion formation in the myocardial tissue.

Catheter devices are commonly used to perform the ablation procedure. They are generally inserted into a major vein or artery or through a bodily cavity such as the mouth, urethra, or rectum. These catheters are then guided to a targeted location in the body (e.g., organ) by manipulating the catheter from the insertion point or the natural body's orifice. By way of example, in coronary applications, a catheter is typically inserted tranvenously in the femoral vein and guided to a cardiac chamber to ablate myocardial tissues. Although catheters work well for a number of applications, in many applications it would be desirable to provide an ablation assembly that can be used to position an ablation device during a surgical procedure.

SUMMARY OF THE INVENTION

To achieve the foregoing and other objects of the invention, methods and devices pertaining to the ablation of tissues inside the cavity of an organ are disclosed. In general, the invention pertains to an ablation assembly, and more particularly to a surgical device, which includes an ablative energy source and an ablative energy delivery device coupled to the ablative energy source. The ablative energy delivery device is configured for delivering ablative energy sufficiently strong to cause tissue ablation. In most embodiments, the ablative energy is formed from electromagnetic energy in the microwave frequency range.

The invention relates, in one embodiment, to an ablation assembly that includes an ablation tool, which has a distal portion configured for delivering ablative energy sufficiently strong to cause tissue ablation, and a probe, which has a needle shaft with a lumen extending therethrough. The needle shaft also has a proximal access end and a distal penetration end that is adapted to penetrate through a wall of an organ to an organ cavity. The lumen is arranged for slidably carrying the ablation tool from an un-deployed position, which places the distal portion of the ablation tool inside the lumen of the needle shaft, to a deployed position, which places the distal portion of the ablation tool past the distal penetration end of the needle shaft.

In some embodiments, the distal portion of the ablation tool is arranged to lie at an angle relative to a longitudinal axis of the probe when the distal portion of the ablation tool is deployed past the distal penetration end of the needle shaft. By way of example, an angle of between about 45 to about 135 degrees may be used. In related embodiments, the ablation assembly includes an angular component for directing the distal portion of the ablation tool to a predetermined angular position. By way of example, a steering arrangement, a biasing arrangement or a curved probe arrangement may be used.

The invention relates, in another embodiment, to an ablation assembly that includes a probe, an antenna and a transmission line. The probe is adapted to be inserted into a body cavity and to penetrate an organ within the body cavity. The probe also has a longitudinal axis. The antenna is carried by the probe for insertion into a cavity within the organ, and the transmission line is carried by the probe for delivering electromagnetic energy to the antenna. Furthermore, the antenna and transmission line are arranged such that when the antenna is deployed into the organ cavity, the antenna lies at an angle relative to the longitudinal axis of the probe. In some embodiments, when the antenna is deployed into the organ cavity, the antenna lies proximate and substantially parallel to the inner wall of the organ.

The invention relates, in another embodiment, to a microwave ablation assembly that includes an elongated probe, a transmission line and antenna device. The probe has a penetration end adapted to penetrate into an organ and an opposite access end. The probe also has a longitudinal axis and defines an insert passage extending therethrough from the access end to the penetration end thereof. The transmission line is arranged for delivering microwave energy, and has a proximal end coupled to a microwave energy source. The antenna device is distally coupled to the transmission line, and is arranged for radiating a microwave field sufficiently strong to cause tissue ablation. The antenna device further includes an antenna and a dielectric material medium disposed around the antenna. Furthermore, the antenna device and at least a portion of the transmission line are each dimensioned for sliding receipt through the insert passage of the elongated probe, while the elongated probe is positioned in the organ, to a position advancing the antenna device past the penetration end of the probe and at an angle relative to the longitudinal axis of the probe.

In some embodiments, the transmission line is a coaxial cable that includes an inner conductor, an outer conductor, and a dielectric medium disposed between the inner and outer conductors. In a related embodiment, a distal portion of the outer conductor is arranged to be exposed inside the cavity of the organ. In another related embodiment, the ablation assembly further includes a ground plane configured for coupling electromagnetic energy between the antenna and the ground plane. The ground plane is generally coupled to the outer conductor of the transmission line and is positioned on the transmission line such that when the antenna is advanced into the organ cavity proximate the inner wall of the organ, the ground plane is disposed outside the organ cavity proximate the outer wall of the organ.

The invention relates, in another embodiment, to a method for ablating an inner wall of an organ. The method includes providing a surgical device that includes a probe and an ablation tool. The probe is adapted to be inserted into a body cavity and to penetrate an organ within the body cavity. The probe also has a longitudinal axis. The ablation tool, which has a distal portion for delivering ablative energy, is carried by the probe for insertion into a cavity within the organ. The method further includes introducing the surgical device into a body cavity. The method additionally includes penetrating a wall of the organ with the probe. The method also includes advancing the probe through the wall of the organ and into an interior chamber thereof. The method further includes deploying the distal portion of the ablation tool inside the interior chamber of the organ at an angle relative to the longitudinal axis of the probe, wherein the distal antenna is positioned proximate an inner wall of the organ. Moreover, the method includes delivering ablative energy that is sufficiently strong to cause tissue ablation.

In most embodiments, the organ, which is being ablated, is the heart. As such, the ablation assembly may be used to create lesions along the inner wall of the heart. By way of example, these lesions may be used treat atrial fibrillation, typical atrial flutter or atypical atrial flutter.

The invention relates, in another embodiment, to an ablation assembly that includes a needle antenna and a transmission line. Both the needle antenna and the transmission line are adapted to be inserted into a body cavity. The transmission line is arranged for delivering electromagnetic energy to the needle antenna, and includes a longitudinal axis. The needle antenna is arranged for transmitting electromagnetic energy that is sufficiently strong to cause tissue ablation. The needle antenna is also includes a penetration end adapted to penetrate an organ within the body cavity such that the needle antenna can be advanced through a wall of the organ into a cavity within the organ. Furthermore, at least one of the needle antenna or the transmission line is bent at an angle relative to the longitudinal axis of the transmission line so that the needle antenna can be positioned proximate an inner wall of the organ.

The invention relates, in another embodiment, to a method for ablating an inner wall of an organ. The method includes providing a surgical device that has a needle antenna distally coupled to a transmission line. The transmission line has a longitudinal axis, and the needle antenna has a distal penetration end that is adapted to penetrate through a wall of an organ. The needle antenna is also adapted for delivering electromagnetic energy. Furthermore, at least one of the needle antenna or the transmission line is bent at an angle relative to the longitudinal axis of the transmission line. The method further includes introducing the surgical device into a body cavity. The method additionally includes penetrating a wall of the organ with the distal penetration end of the needle antenna. The method also includes advancing the needle antenna through the wall of the organ and into an interior chamber thereof. The method further includes positioning the needle antenna inside the interior chamber of the organ such that the needle antenna is proximate an inner wall of the organ. Moreover, the method includes radiating electromagnetic energy that is sufficiently strong to cause tissue ablation.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 12A & 12B are side elevation views, in cross section, of an ablation assembly, in accordance with one embodiment of the present invention.

FIGS. 13A & 13B are side elevation views, in cross section, of an ablation assembly, in accordance with one embodiment of the present invention.

FIGS. 14A & 14B are side elevation views, in cross section, of an ablation assembly, in accordance with one embodiment of the present invention.

FIG. 22 is a side elevation view, in cross section, of a needle antenna, in accordance with one embodiment of the present invention.

FIG. 23 is a side elevation view, in cross section, of a needle antenna, in accordance with one embodiment of the present invention.

FIG. 24 is a side elevation view, in cross section, of a needle antenna, in accordance with one embodiment of the present invention.

FIGS. 25A & 25B are side elevation views of a needle antenna having acute and obtuse angular positions, respectively, in accordance with one embodiment of the present invention.

FIG. 27A is a perspective view of a needle antenna, in accordance with one embodiment of the present invention.

FIG. 27B is a side elevation view of the needle antenna of FIG. 27A, in accordance with one embodiment of the present invention.

FIG. 27C is a side elevation view of the needle antenna of FIG. 27A after penetrating an organ wall (in cross section), in accordance with one embodiment of the present invention.

DETAILED DESCRIPTION OF PREFERRED EMBODIMENTS

The present invention will now be described in detail with reference to a few preferred embodiments thereof and as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps have not been described in detail in order not to unnecessarily obscure the present invention.

The present invention provides an ablation assembly that is capable of ablating tissues inside the cavity of an organ (or duct). More specifically, the present invention provides an ablation assembly that is capable of producing lesions along an interior wall of an organ. The ablation assembly generally includes an ablative energy source and an ablative energy delivery device coupled to the ablative energy source. The ablative energy delivery device is configured for delivering ablative energy sufficiently strong to cause tissue ablation. The ablative energy delivery device generally includes an angular component that is used to position the device inside the organ after the device has been inserted through the wall of the organ. In one embodiment, a probe (or introducer), which has a penetration end adapted to penetrate through a wall of an organ, is used to help insert (or introduce) the device through the wall of the organ. In another embodiment, the device itself is arranged to include a penetration end that is adapted to penetrate through a wall of an organ.

In accordance with one embodiment of the present invention, the ablation assembly includes a probe and an ablation tool. The ablation tool, which includes an antenna and a transmission line coupled to the antenna, is adapted to be carried by the probe for insertion within a cavity inside the organ. The transmission line is arranged for delivering electromagnetic energy to the antenna. The probe is adapted to be inserted into a body cavity and to penetrate an organ within the body cavity. Furthermore, the ablation assembly is arranged so that when the antenna is deployed into the organ cavity, the antenna lies at an angle relative to the longitudinal axis of the probe. In some embodiments, upon deployment, the antenna is configured to assume a predetermined position that substantially matches the shape and/or angular position of the wall to be ablated.

Figure 1:
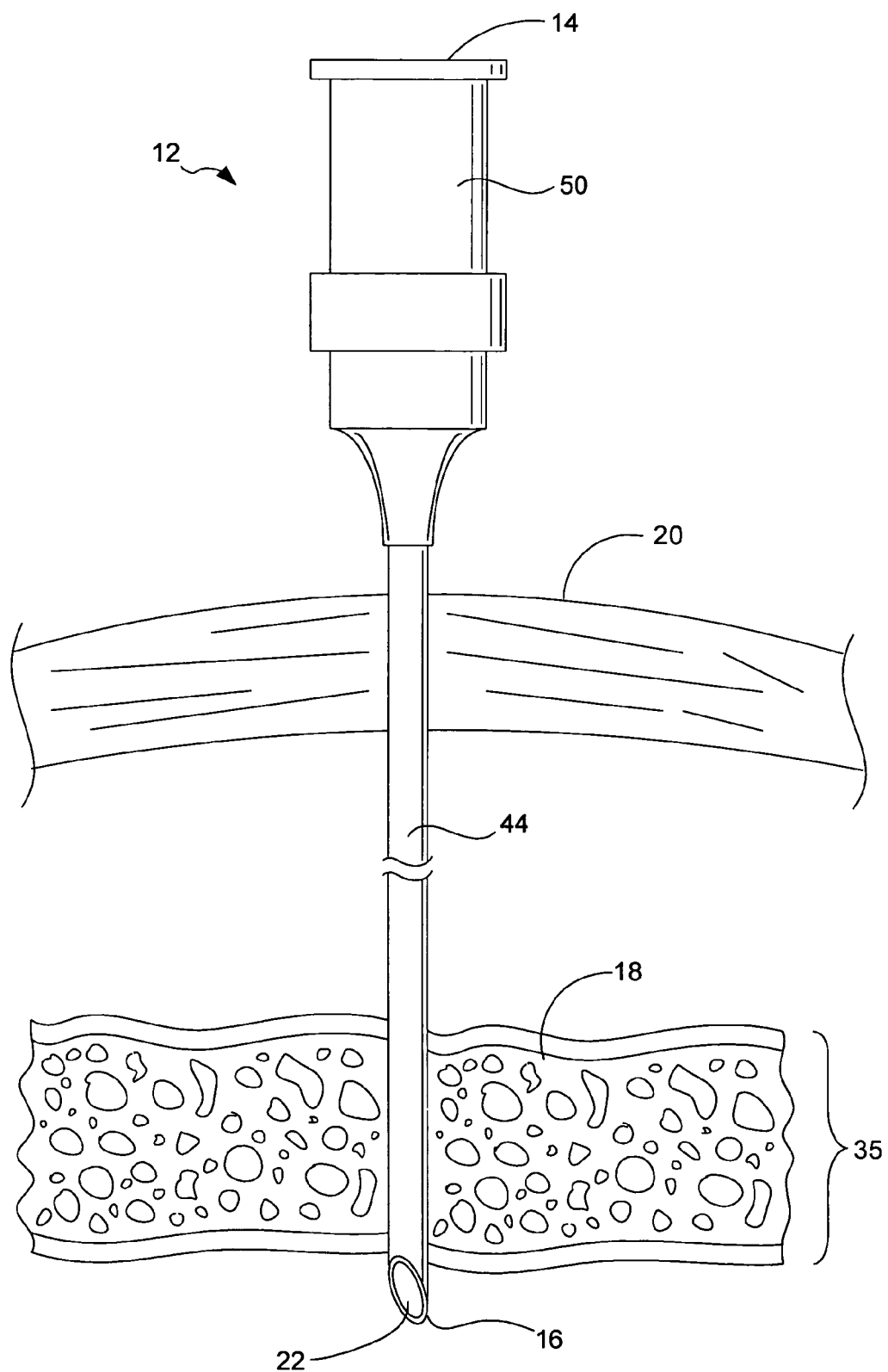
FIG. 1 is a side elevation view, in cross section, of a probe penetrating a body cavity and an organ, in accordance with one embodiment of the present invention.

Referring initially to FIGS. 1-3, an ablation assembly in accordance with one embodiment of the invention will be described. In this embodiment, the ablation assembly, generally designated 10 (illustrated in FIG. 3), includes a relatively thin, elongated probe 12 (illustrated in FIG. 1), which works in combination with an ablation tool 24 (illustrated in FIG. 2). The probe 12 has a proximal access end 14 and an opposite distal penetration end 16 adapted to penetrate an organ 18 within a body cavity 20. The probe 12 also has a longitudinally extending lumen 22 that is sized suitably for receiving the ablation tool 24 therethrough. The ablation tool 24 includes a transmission line 28 that carries an antenna device 30 at its distal end. The antenna device 30 is designed to generate an electromagnetic field sufficiently strong to cause tissue ablation. A proximal end 42 of the transmission line 28 is coupled to an energy source (not shown).

Figure 3B:
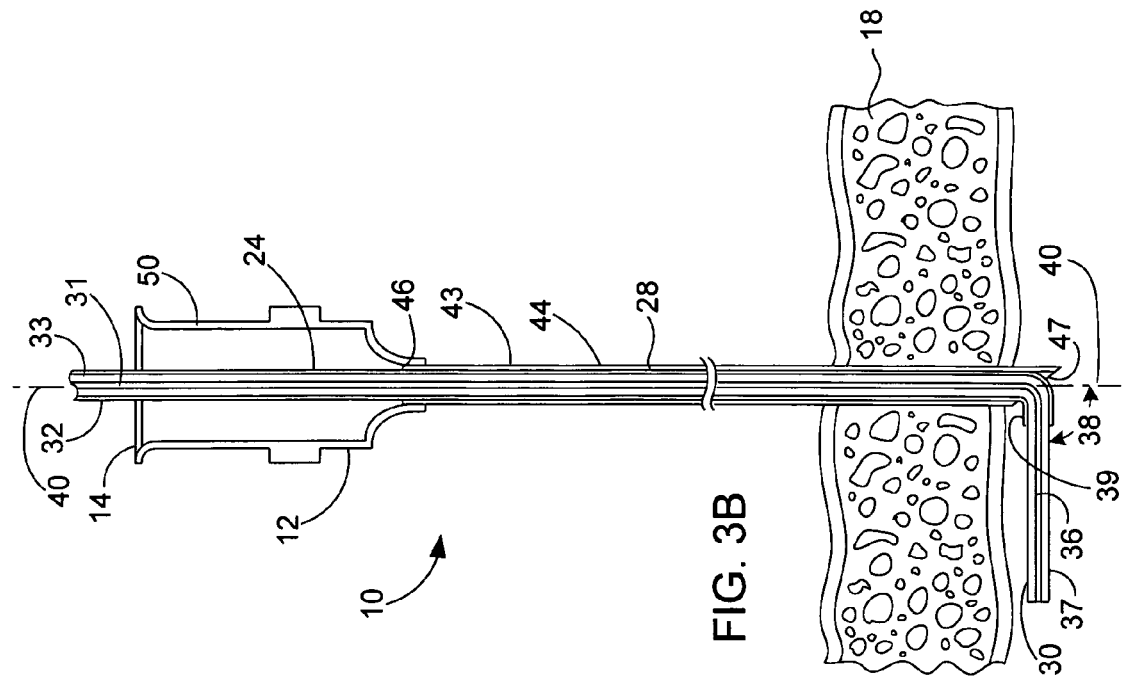
FIGS. 3A & 3B is a sequence of side elevation views, in cross section, of the ablation tool of FIG. 2 being inserted and advanced through the probe of FIG. 1, in accordance with one embodiment of the present invention.

The antenna device 30 and the transmission line 28 are sized such that they are slidable through the lumen 22 while the elongated probe 12 is positioned in a wall 35 of the organ 18. As such, the ablation tool 24 may be advanced within the probe 12 until the antenna device 30 is moved into a cavity within the organ 18 at a position beyond the penetration end 16 of the probe 12. As shown in FIG. 3B, the ablation tool 24 is configured so that when it is extended beyond the penetration end 16 of the probe 12, the antenna 30 lies at an angle 38 relative to the longitudinal axis 40 of the probe 12 (the axis taken from the proximal end 14 of the probe). In many embodiments, the angle 38 is arranged such that when the antenna device 30 is deployed into the organ cavity, the antenna device 30 assumes a predetermined angular position that matches the shape and/or angular position of the wall to be ablated. By way of example, an angular position that places the antenna device substantially parallel to the cavity wall may be used.

Accordingly, an ablation assembly is provided which utilizes a thin, elongated probe as a deployment mechanism to position an antenna device within the organ targeted for ablation. Once the probe is positioned in a wall of the organ, the antenna device and the transmission line are inserted through the passage of the probe as a unit until the antenna device is positioned inside the cavity of the organ. Subsequently, an electromagnetic field is emitted from the antenna device that is sufficiently strong to cause tissue ablation. This arrangement is especially beneficial when the areas targeted for ablation have obstructions along the outer wall of the organ. For example, the ablation assembly may be used to bypass and navigate around layers of fat or veins that surround the epicardial surface (e.g., outer wall) of the heart.

Additionally, the angular component of the ablation assembly allows precise positioning and placement of the antenna device at specific locations within the cavity of a bodily organ. As a result, the ablative energy can be accurately transmitted towards the tissue targeted for ablation.

Figure 3A:
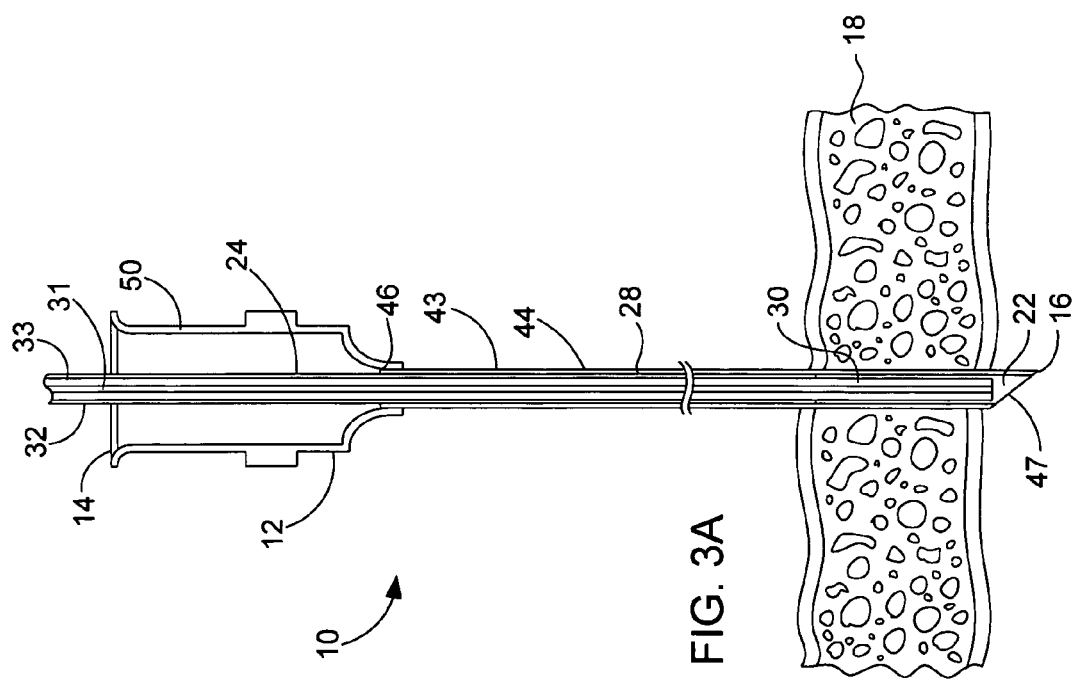

Referring to FIGS. 3A & 3B, the elongated probe 12 includes a rigid needle 43 having an elongated needle shaft 44 adapted to pierce through the organ 18 at its distal penetration end 16. By way of example, the distal penetration end 16 may take the form of a conventional beveled tipped needle or a beveled point chamfered needle both of which form a sharp cutting edge. The lumen 22 extends longitudinally through the needle shaft 44, and includes a proximal access opening 46 and an opposite distal penetration opening 47 at the distal penetration end 16 thereof. As shown, a handle 50 is disposed at the proximal end of the needle shaft 44 to help facilitate the insertion and extraction of the antenna device 30 into and out of the proximal access opening 46 of the lumen 22.

In general, the needle shaft 44 is a thin walled rigid tube having an outer diameter of about less than about 3 mm and an inner diameter of about less than 1.5 mm. In addition, a wall thickness in the range of between about 0.003 inches to about 0.007 inches, and a lumen diameter (inner diameter) in the range of about 0.040 inch to about 0.060 inch may be used. In the embodiment shown, the wall thickness is about 0.005 inches and the lumen diameter is about 0.050 inches. This relatively small diameter size is particularly suitable for use in highly vascularized organs, such as the heart, so as to minimize the puncture diameter and, thus, potential bleeding. It will be appreciated, of course, that the present invention may be utilized to ablate the tissues of other organs, and more particularly, the interior walls of other organs as well. Furthermore, the needle shaft may be formed from any suitable material that is rigid and bio-compatible. By way of example, stainless steel may be used. Additionally, it should be noted that the sizes are not a limitation, and that the sizes may vary according to specific needs of each device.

In most embodiments, the probe is first positioned through the skin or a body cavity, and then into the targeted organ or tissues. Depending upon the depth of penetration, the wall of the penetrated organ surrounding the needle shaft may be employed to vertically and laterally position (and support) the probe during tissue ablation. Referring to FIGS. 3A and 3B, once the probe 12 is properly positioned and retained at the targeted penetration site, and more particularly once the distal penetration end 16 of the needle shaft 44 is placed at the proper selected depth (such as that shown in FIGS. 3A & 3B), the antenna device 30 may be advanced into the organ cavity.

In some embodiments, the probe 12 and the ablation tool 24 are formed as an integral unit, wherein the antenna device 30 is moved into position by advancing the ablation tool 24 through the probe from a first predetermined position to a second predetermined position. For example, a handle, which is mechanically coupled to the ablation tool 24, may be used to control the sliding movement of the antenna tool 24 through the probe 12. As such, the first predetermined position is configured to place the antenna device 30 in an un-advanced position (as shown in FIG. 3A) and the second predetermined position is configured to place the antenna device 30 in a deployed position (as shown in FIG. 3B). In other embodiments, the probe 12 and the ablation tool 24 are separate elements and therefore the ablation tool 24 is inserted into the probe 12 after the probe 12 has been positioned in the targeted area of the organ 18. After ablation tool 24 has been inserted into the probe 12, the antenna device 30 can be advanced from the un-advanced position (as shown in FIG. 3A) to the deployed position (as shown in FIG. 3B).

During deployment, the ablation tool 24 is moved through the handle 50 and through the lumen 22. As best viewed in FIGS. 3A & 3B the antenna device 30 and the associated transmission line 28 are advanced longitudinally through the lumen 22 of the needle shaft 44 to the distal penetration end 16 thereof. Upon subsequent advancement, the antenna device 30 may be manipulated to extend through the penetration opening 47 of the insert passage 22 and into the cavity of the organ 18. Such advancement allows the antenna device 30 to assume a predetermined position having an angle 38 relative to the longitudinal axis 40 of the probe 12. As shown, the predetermined position is in a direction towards the inner wall of the organ 18, and substantially parallel to the tissue targeted for ablation thereof. In one embodiment, the antenna device is arranged to move into the angled position during advancement of the antenna tool through the probe. In another embodiment, the antenna device is arranged to move into the angled position after advancement of the antenna tool through the probe. Deployment techniques will be discussed in greater detail below.

Figure 4A:
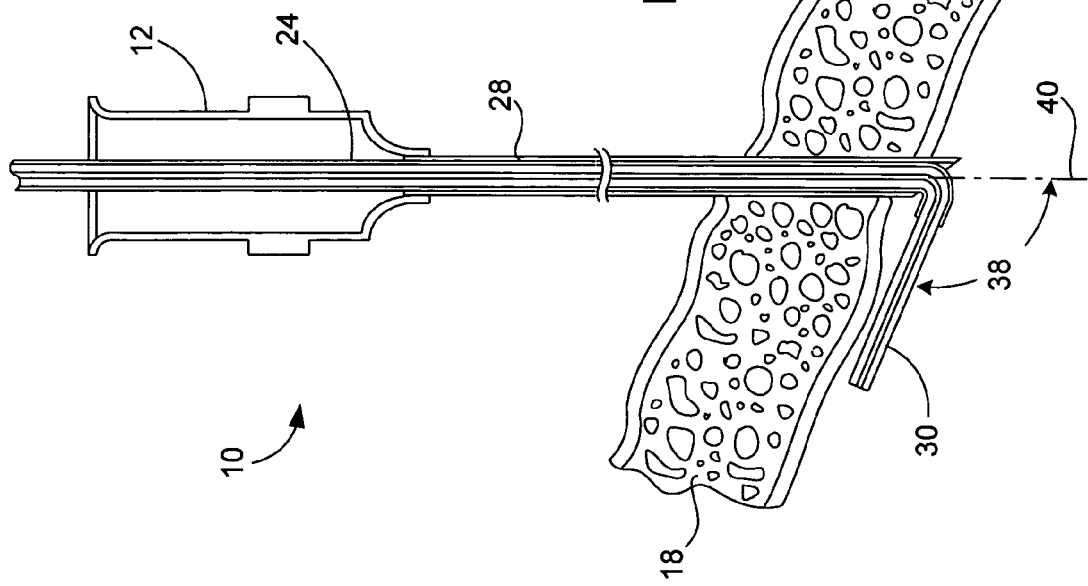
FIGS. 4A & 4B are side elevation views, in cross section, of the ablation assembly of FIGS. 3A & 3B having acute and obtuse angular positions, respectively, in accordance with one embodiment of the present invention.
Figure 4B:
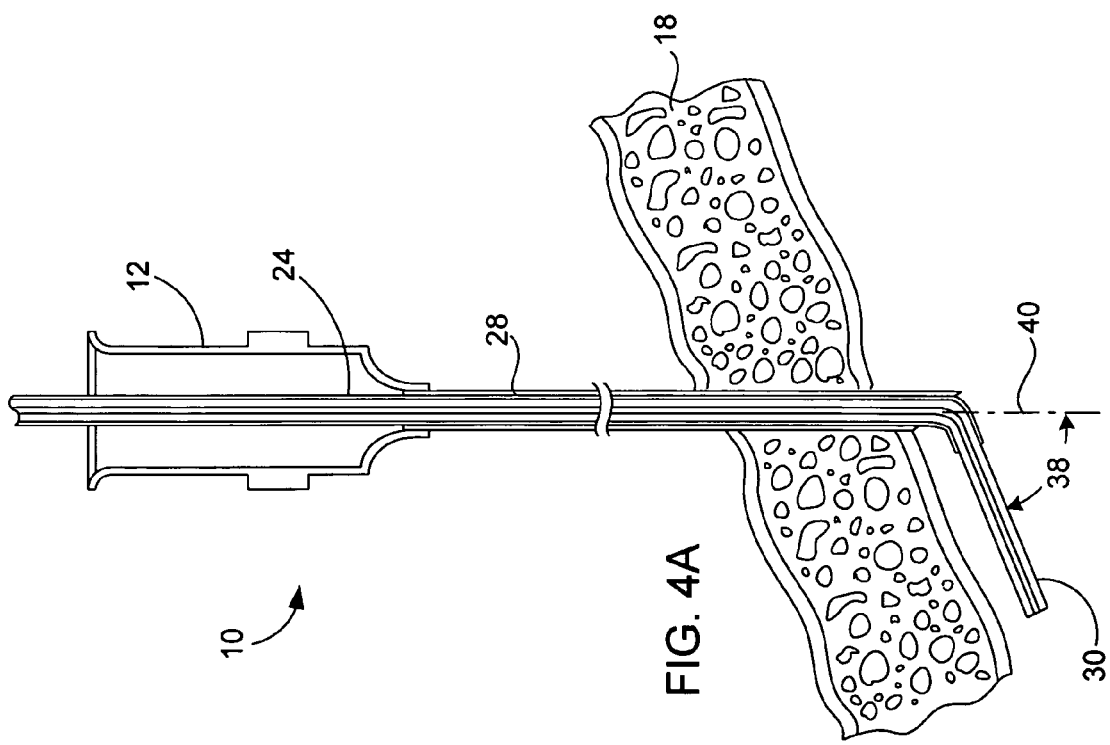

As shown in FIGS. 3A & 3B, the probe 12 is perpendicularly penetrating the organ 18, and the antenna device 30 is positioned about 90 degrees from the longitudinal axis 40 of the probe 12. It is contemplated, however, that this position is not always possible because some organs are particularly difficult to access, and therefore the probe 12 may be inserted into the wall of the organ 18 at different angles. Accordingly, the present invention may be configured to provide a range of angled positions to match the shape and/or angular position of the wall to be ablated. By way of example, an antenna device position having an angle in the range of between about 45 degrees to about 135 degrees may be used. To illustrate this, FIG. 4A shows the antenna device 30 in an acute angular position having an angle 38 of about 60 degrees relative to the longitudinal axis 40, and FIG. 4B shows the antenna device 30 in an obtuse angular position having an angle 38 of about 120 degrees relative to the longitudinal axis 40. These angular positions are important parameters for ensuring that the antenna device is properly positioned in a direction towards the tissue targeted for ablation. Furthermore, although only three angles have been shown, it should be noted that this is not a limitation and that other angles may be used.

Several embodiments associated with angled positioning and deployment of the antenna device will now be described in detail. It should be appreciated, however, that the present invention may be embodied in many other specific forms without departing from the spirit or scope of the invention, and may be practiced without some or all of these specific details.

In one embodiment, the ablation assembly may include a biasing member that is specifically formed and shaped for urging the antenna device to a predetermined bent position. That is, the biasing member has a predetermined shape that corresponds to the angled position of the antenna device. As soon as the antenna device is advanced into the organ cavity the biasing member moves to assume its predetermined shape and thus the antenna device moves to the predetermined bent position. The biasing member generally consists of one or more pre-shaped elastic or spring like strips or rods that extend through the ablation arrangement in the area of the antenna device. The strips or rods may be arranged to have a circular, rectangular, or other cross section shape. By way of example, stainless steels, plastics and shape memory metals may be used.

In one implementation of this embodiment, the spring like material is a shape memory metal such as NiTi (Nitinol). Nitinol is a super elastic material that typically exhibits superb flexibility and unusually precise directional preference when bending. Accordingly, when the antenna device is positioned within the cavity of an organ, the nitinol strip enables the antenna device to conform to the inner wall of the organ. Similarly, when the antenna device is withdrawn from the organ, the Nitinol strip facilitates straightening to allow removal through the probe.

In another embodiment, the assembly may include a steering system for bending the antenna device to a predetermined bent position. The steering system generally includes one or more wires that extend through the ablation arrangement. The wires are used to pull the antenna device from an unbent position to a bent position causing controlled, predetermined bending at the antenna device. The pull wires are generally fastened to anchors, which are disposed (attached to) at the proximal end of the antenna device. In this type of arrangement, a steering element, located on the handle 50, may be used to pull on the wires to facilitate the bending. However, the actual position of the handle may vary according to the specific needs of each ablation assembly. Steering systems are well known in the art and for the sake of brevity will not be discussed in greater detail.

Figure 5:
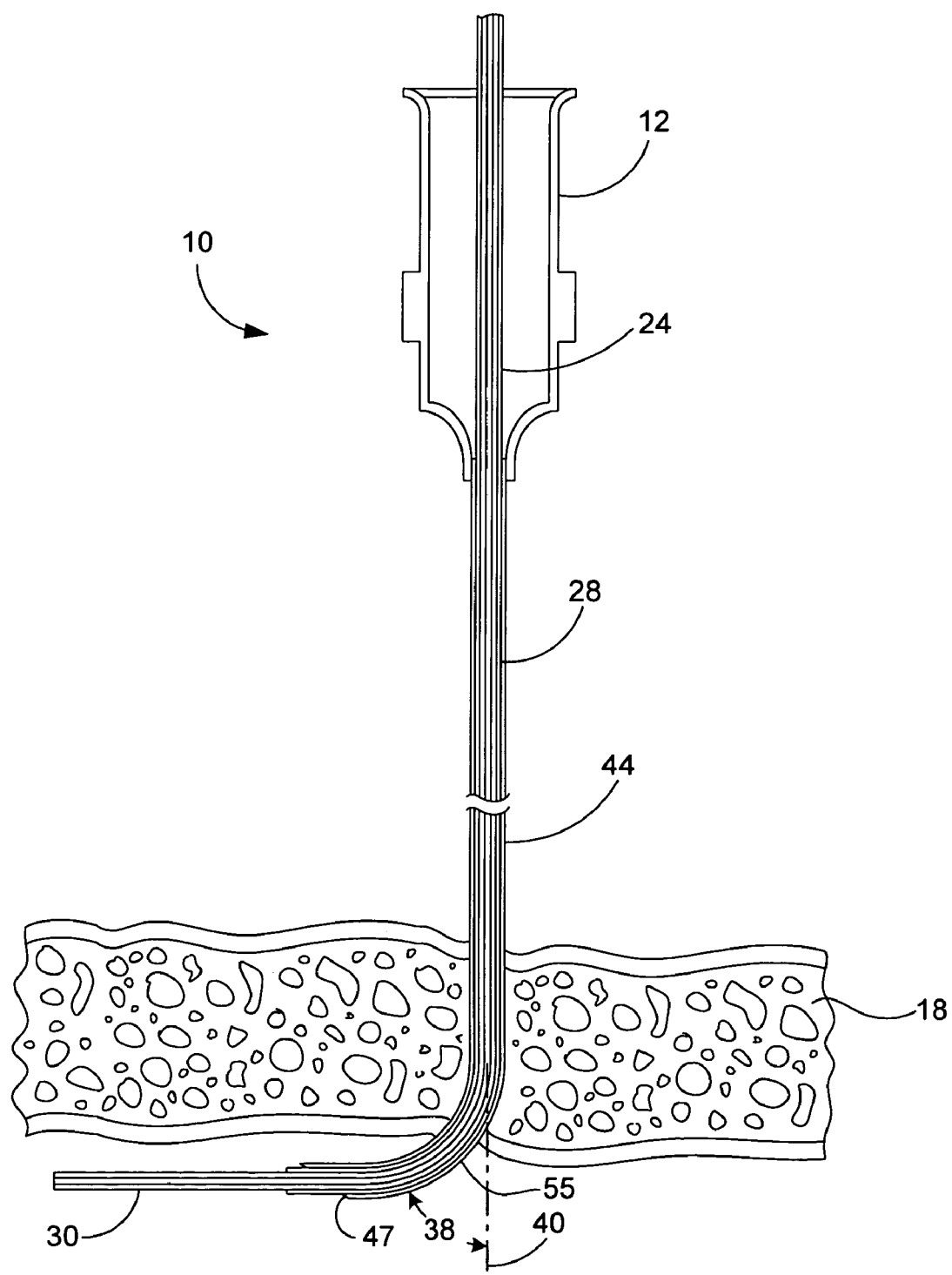
FIG. 5 is a side elevation view, in cross section, of an alternative embodiment of the probe having a curved needle shaft, in accordance with one embodiment of the present invention.

In another embodiment, the needle shaft of the probe can be pre-bent or curved to direct the antenna device to its advanced position. Referring to FIG. 5, the needle shaft 44 of the probe 12 includes a curved section 55 which redirects the position of the antenna device 30 in a manner skewed from the axis 40 of the proximal end 14 of the probe 12. As the distal end of the antenna device 30 contacts the curved wall 55 of the insert passage, the antenna device 30 is urged toward the distal penetration opening 47 and into the cavity of organ 18 at an angle 38 relative to axis 40. Although the probe is shown as having a substantially right angle, it should be noted that the angle of the curved portion may vary according to the specific needs of each ablation assembly. For example, the angle 38 may also be configured to be acute or obtuse (such as in FIGS. 4A & 4B) relative to the longitudinal axis 40.

Referring back to FIGS. 2 & 3, the ablation tool 24 is illustrated having an elongated flexible transmission line 28 and an antenna device 30 coupled to the distal end of the transmission line 28. The transmission line 28 is adapted for insertion into the probe 12 and is arranged for actuating and/or powering the antenna device 30. In microwave devices, a coaxial transmission line is typically used, and therefore, the transmission line 28 includes an inner conductor 31, an outer conductor 32, and a dielectric material 33 disposed between the inner and outer conductors 31, 32. Furthermore, at the proximal end of the transmission line 28 is an electrical connector 42 adapted to electrically couple the transmission line 28, and therefore the antenna device 30, to the energy source (not shown). The transmission line 28 may also include a flexible outer tubing (not shown) to add rigidity and to provide protection to the outer conductor 32. By way of example, the flexible outer tubing may be made of any suitable material such as medical grade polyolefins, fluoropolymers, or polyvinylidene fluoride.

Figure 2A:
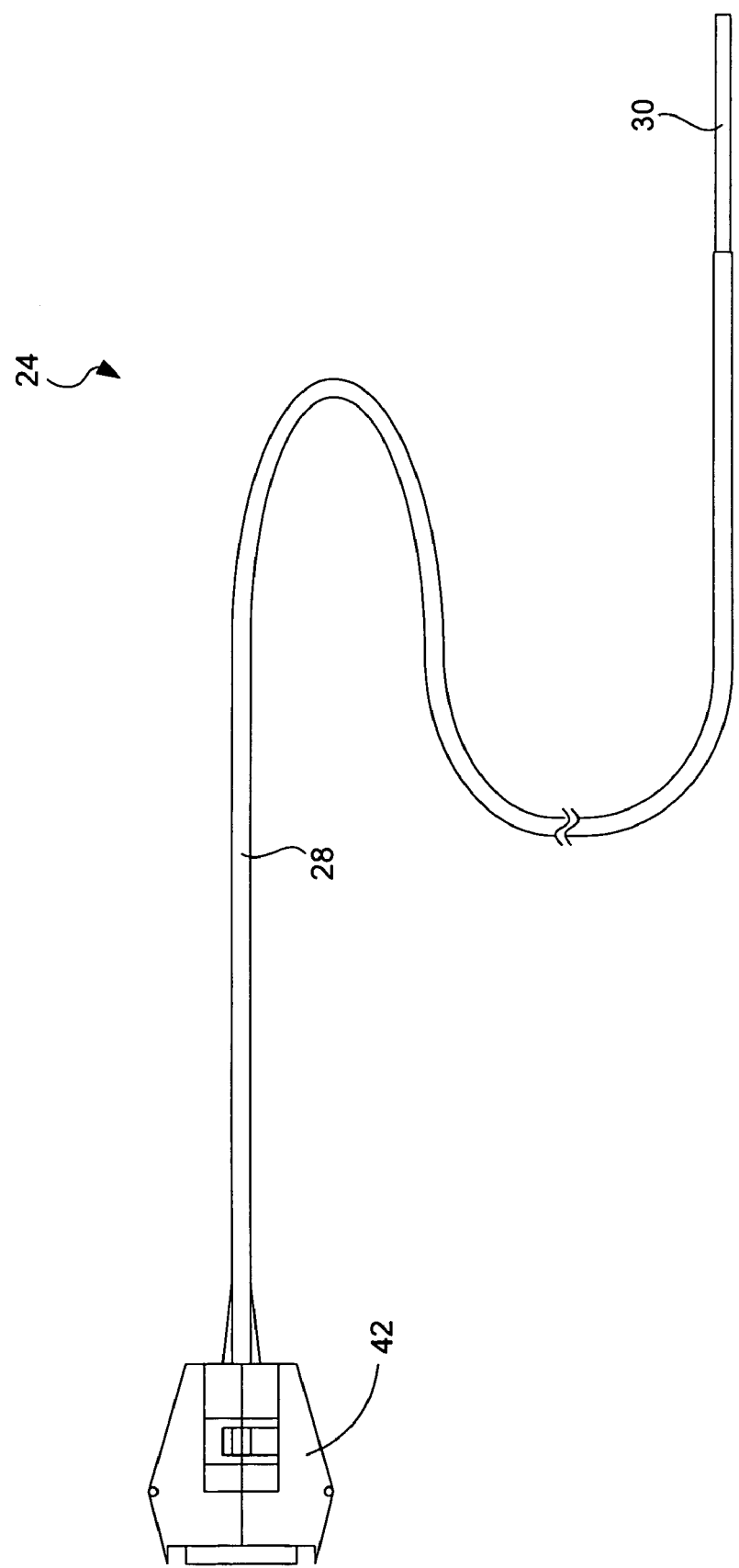
FIG. 2A is a top plan view of an ablation tool including an antenna device and a transmission line, in accordance with one embodiment of the present invention.
Figure 2B:
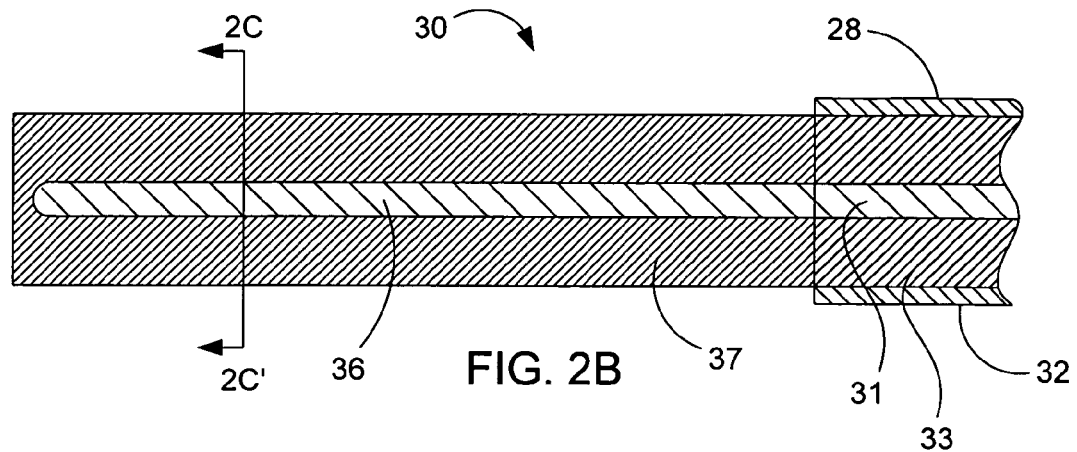
FIG. 2B is a side elevation view, in cross section, of the antenna device of FIG. 2A, in accordance with one embodiment of the present invention.
Figure 2C:
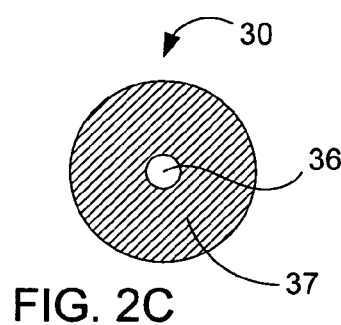
FIG. 2C is a front elevation view of the antenna device taken substantially along the plane of the line 2-2' in FIG. 2B, in accordance with one embodiment of the present invention.
Figure 2D:
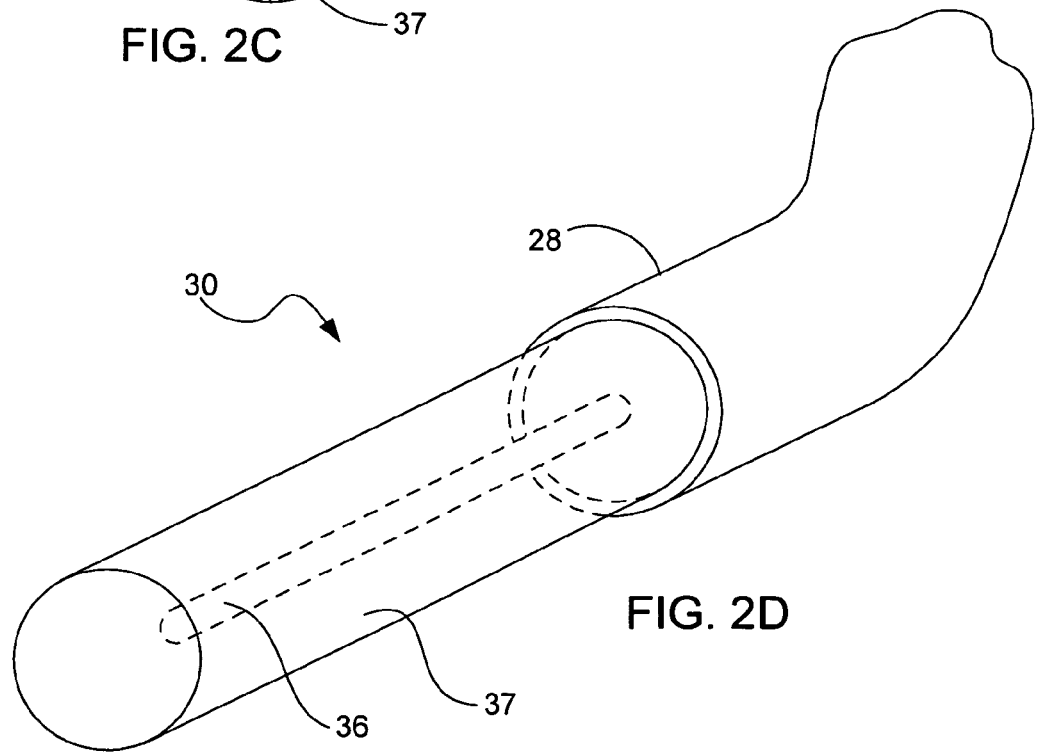
FIG. 2D is a perspective view of the antenna device of FIG. 2A, in accordance with one embodiment of the present invention.

As shown in FIGS. 2B-D, the antenna device 30, which is also adapted for insertion into the probe 12, generally includes an antenna wire 36 having a proximal end that is coupled directly or indirectly to the inner conductor 31 of the transmission line 28. A direct connection between the antenna wire 36 and the inner conductor 31 may be made in any suitable manner such as soldering, brazing, ultrasonic or laser welding or adhesive bonding. As will be described in more detail below, in some implementations, it may be desirable to indirectly couple the antenna to the inner conductor through a passive component in order to provide better impedance matching between the antenna device and the transmission line.

In another embodiment, the antenna device 30 can be integrally formed from the transmission line 28 itself. This is typically more difficult from a manufacturing standpoint but has the advantage of forming a more rugged connection between the antenna device and the transmission line. This design is generally formed by removing the outer conductor 32 along a portion of the coaxial transmission line 28. This exposed portion of the dielectric material medium 33 and the inner conductor 31 embedded therein define the antenna device 30 which enables the electromagnetic field to be radiated substantially radially perpendicular to the inner conductor 31. In this type of antenna arrangement, the electrical impedance between the antenna device 30 and the transmission line 28 are substantially the same. As a result, the reflected power caused by the low impedance mismatch is also substantially small which optimizes the energy coupling between the antenna and the targeted tissues.

The antenna wire 36 is formed from a conductive material. By way of example, spring steel, beryllium copper, or silver plated copper may be used. Further, the diameter of the antenna wire 36 may vary to some extent based on the particular application of the ablation assembly and the type of material chosen. By way of example, in coronary applications using a monopole type antenna, wire diameters between about 0.005 inches to about 0.020 inches work well. In the illustrated embodiment, the diameter of the antenna is about 0.013 inches.

In an alternate embodiment, the antenna wire 36 can be formed from a shape memory metal such as NiTi (Nitinol). As mentioned, Nitinol is a super elastic material that typically exhibits superb flexibility and unusually precise directional preference when bending. Accordingly, when the antenna device 30 is positioned within the cavity of an organ, the antenna wire 36 enables the antenna device 30 to conform to the inner wall of the organ. Similarly, when the antenna device 30 is withdrawn from the organ, the antenna wire 36 facilitates straightening to allow removal through the probe 12. It should be noted, however, that the electrical conductivity of the Nitinol is not very good, and as a result, Nitinol can heat significantly when power (e.g., microwave) is applied. In one implementation, therefore, a layer of good conducting material is disposed over the Nitinol. For example, silver plating or deposition may be used. The thickness of the good conducting material can vary between about 0.00008 to about 0.001 inches, depending on the conductivity of the selected material.

The length of the ablative energy generated by the ablation instrument will be roughly consistent with the length of the antenna device 30. As a consequence, ablation devices having specified ablation characteristics can be fabricated by building ablation devices with different length antennas. By way of example, in coronary applications, an antenna length between about 20 mm and about 50 mm and more particularly about 30 mm may be used. In some applications, the probe may be used to introduce a measuring tool that is arranged to measure the ablative lesion distance needed for a particular procedure. According to the measurements, the length of the antenna device can be selected. For instance, in some coronary applications, the tool may be used to measure the distance between the mitral valve and the pulmonary veins.

As shown, the antenna wire 36 is a monopole formed by a longitudinal wire that extends distally from the inner conductor 31. However, it should be appreciated that a wide variety of other antenna geometries may be used as well. By way of example, non-uniform cross-section monopole, helical coils, flat printed circuit antennas and the like also work well. Additionally, it should be understood that longitudinally extending antennas are not a requirement and that other shapes and configurations may be used. For example, the antenna may be configured to conform to the shape of the tissue to be ablated or to a shape of a predetermined ablative pattern for creating shaped lesions.

Furthermore, the antenna wire 36 is generally encapsulated by an antenna enclosure 37. The antenna enclosure 37 is typically used to obtain a smooth radiation pattern along the antenna device 30, and to remove the high electromagnetic field concentration present when an exposed part of the antenna wire is in direct contact with the tissue to be ablated. A high field concentration can create a high surface temperature on the tissue to ablate which is not desirable, especially for cardiac applications. The antenna enclosure 37 may be made of any suitable dielectric material with low water absorption and low dielectric loss tangent such as Teflon or polyethylene. As will be described in greater detail below, in some implementations, it may be desirable to adjust the thickness of the antenna enclosure 37 in order to provide better impedance matching between the antenna device 30 and the tissue targeted for ablation. Although exposing the antenna wire is not typically done because of the high field concentration, it should be noted that the dielectric material forming the antenna enclosure 37 can be removed to form an exposed metallic antenna.

As shown in FIG. 3B, the outer conductor 32 is arranged to have a distal portion 39 that is exposed, beyond the penetration end 16 of the probe 12, when the antenna device 30 is in its advanced position. While not wishing to be bound by theory it is generally believed that the radiated field tends to be more confined along the antenna device 30 when the distal end of the outer conductor 32 is extended in the organ cavity and exposed to the surrounding medium. By way of example, an exposed outer conductor having a length of about 1 mm to about 2 mm works well. Although the outer conductor is shown and described as being exposed it should be understood that this is not a limitation and that the ablation arrangement can be made with or without an exposed outer conductor.

Figure 6A:
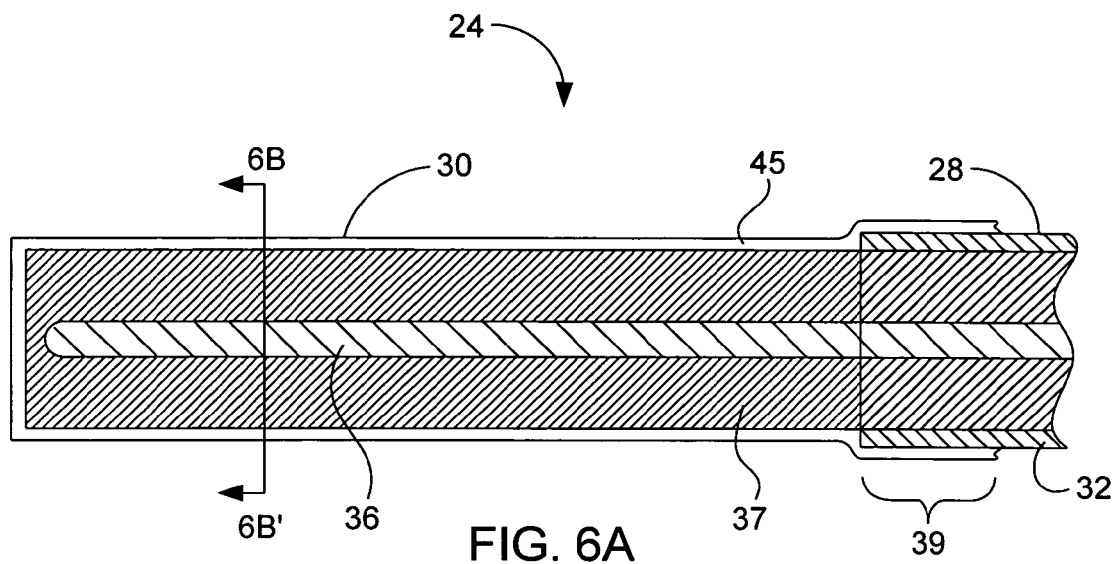
FIG. 6A is a side elevation view, in cross section, of another embodiment of the antenna device.
Figure 6B:
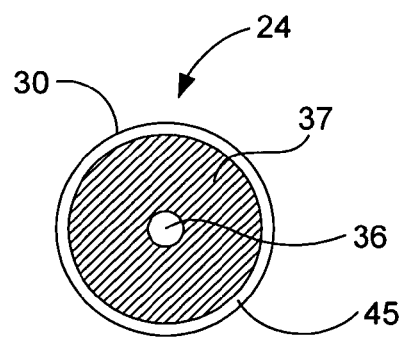
FIG. 6B is a front elevation view of the antenna device taken substantially along the plane of the line 6-6' in FIG. 6A, in accordance with one embodiment of the present invention.

In one embodiment, the antenna device and the outer conductor are covered by a layer of dielectric. This layer of dielectric helps to remove the high concentration of electromagnetic field generated by the uncovered distal portion of the outer conductor. This configuration is better suited for cardiac applications because the high field concentration can potentially generate coagulum or carbonization that can trigger an embolic event. As shown in FIGS. 6A & 6B, the ablation tool 24 includes a protective sheath 45 that surrounds the outer periphery of the antenna device 30 and a portion of the outer conductor 32 of the transmission line 28. More specifically, the protective sheath 45 is arranged to cover at least a portion of the exposed distal portion 39 of the outer conductor 32 and the antenna enclosure 37. As shown, the protective sheath may also cover the distal end of the antenna enclosure 37. By way of example, the protective sheath may be formed from any suitable dielectric material such as Teflon (PTFE), FEP, Silicon and the like.

In accordance with one embodiment of the present invention, the ablation arrangement is arranged to transmit electromagnetic energy in the microwave frequency range. When using microwave energy for tissue ablation, the optimal frequencies are generally in the neighborhood of the optimal frequency for heating water. By way of example, frequencies in the range of approximately 800 MHz to 6 GHz work well. Currently, the frequencies that are approved by the U.S. FCC (Federal Communication Commission) for experimental clinical work are 915 MHz and 2.45 GHz. Therefore, a power supply having the capacity to generate microwave energy at frequencies in the neighborhood of 2.45 GHz may be chosen. The power supply generally includes a microwave generator, which may take any conventional form. At the time of this writing, solid state microwave generators in the 1-3 GHz range are expensive. Therefore, a conventional magnetron of the type commonly used in microwave ovens is utilized as the generator. It should be appreciated, however, that any other suitable microwave power source could be substituted in its place, and that the explained concepts may be applied at other frequencies like about 434 MHz, 915 MHz or 5.8 GHz (ISM band).

A frequent concern in the management of microwave energy is impedance matching of the antenna and the various transmission line components with that of the power source. An impedance mismatch will cause the reflection of some portion of the incident power back to the generator resulting in a reduction of the overall efficiency. It is desirable to match the impedance of the transmission line 28 and the antenna device 30 with the impedance of the generator, which is typically fifty ohms.

The transmission line 28 is therefore provided by a conventional fifty ohm coaxial design suitable for the transmission of microwave energy at frequencies in the range of about 400 to about 6000 megahertz. As shown in FIG. 2B, the coaxial transmission line 28 includes an inner conductor 31 and a concentric outer conductor 32 separated by a dielectric material medium 33. The inner conductor 31 is formed from a solid metallic material core having good electrical conductivity. The dielectric medium 33 is formed from a semi-rigid dielectric material having a low loss tangent. The outer conductor 32 is formed from a braided sleeve of metallic wires that provide shielding and good flexibility thereof.

To achieve the above-indicated properties from a relatively small diameter ablation arrangement while still maintaining the impedance match, the size of the inner conductor 31 and the outer conductor 32, as well as the size, shape and material of the dielectric material medium must be carefully selected. Each of these variables, together with other factors related to the antenna device, may be used to adjust the impedance and energy transmission characteristics of the antenna device. Such preferable dielectric materials include air expended TEFLON™, while the inner and outer conductors are composed of silver or copper. The impedance of the transmission line may be determined by the equation:

$$Z_0 = \frac{60 \cdot \ln\left(\frac{b}{a}\right)}{\sqrt{\varepsilon_r}}$$

where "b" is the diameter of the dielectric material medium, "a" is the diameter of the inner conductor and $\in_r$ is the dielectric constant of the dielectric material medium 33. It will be understood that a characteristic impedance other than fifty ohms can also be used to design the microwave ablation system. Also, in order to obtain good mechanical characteristics of the coaxial cable assembly, it is important to consider the hardness or malleability of the selected material.

As it was explained earlier, it is also important to match the impedance of the antenna with the impedance of the transmission line. As is well known to those skilled in the art, if the impedance is not matched to the transmission line, the microwave power is reflected back to the generator and the overall radiation efficiency tends to be well below the optimal performance. Several embodiments associated with tuning (e.g., improving or increasing the radiation efficiency) the antenna device will now be described in detail.

In one embodiment, an impedance matching device is provided to facilitate impedance matching between the antenna device and the transmission line. The impedance matching device is generally disposed proximate the junction between the antenna and the transmission line. For the most part, the impedance matching device is configured to place the antenna structure in resonance to minimize the reflected power, and thus increase the radiation efficiency of the antenna structure. In one implementation, the impedance matching device is determined by using a Smith Abacus Model. The impedance matching device may be determined by measuring the impedance of the antenna with a network analyzer, analyzing the measured value with a Smith Abacus Chart, and selecting the appropriate matching device. By way of example, the impedance matching device may be any combination of serial or parallel capacitor, resistor, inductor, stub tuner or stub transmission line. An example of the Smith Abacus Model is described in Reference: David K. Cheng, "Field and Wave Electromagnetics," second edition, Addison-Wesley Publishing, 1989, which is incorporated herein by reference.

Figure 7:
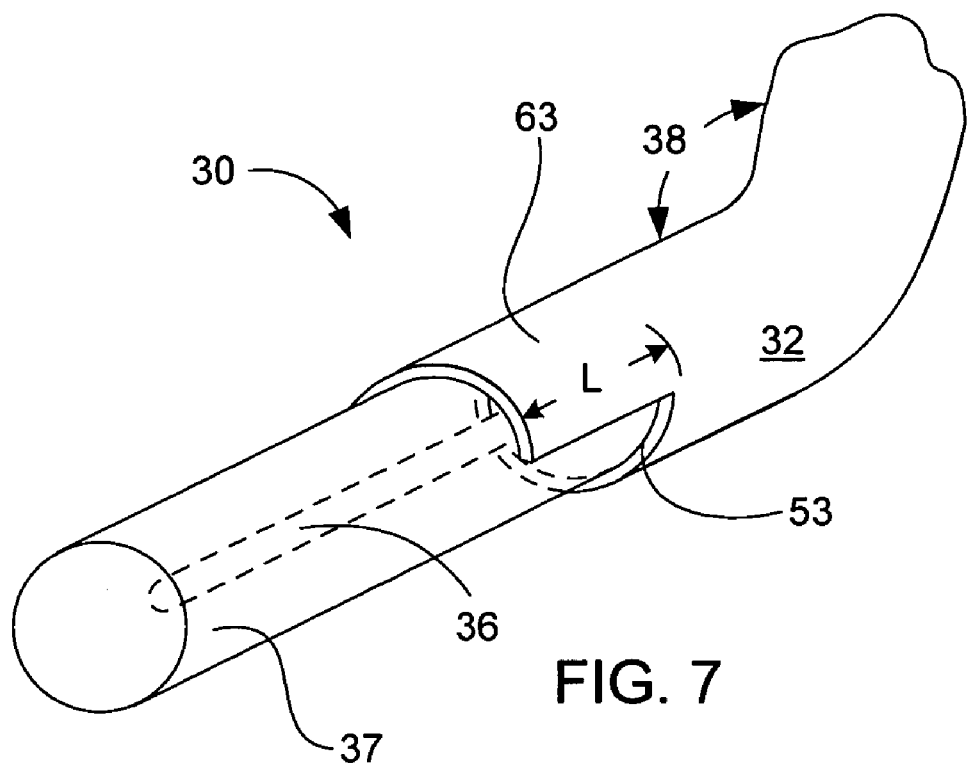
FIG. 7 is a perspective view of another embodiment of the antenna device.

In another embodiment, as shown in FIG. 7, the antenna device 30 includes a tuning stub 63 for improving the radiation efficiency of the antenna device 30. The tuning stub 63 is a circumferentially segmented section that extends distally from the distal end 53 of the outer conductor 32. In some embodiments, the tuning stub 63 is integrally formed from the outer conductor 32 and in other embodiments, the tuning stub 63 is coupled to the outer conductor 32. As shown, the tuning stub 63 is generally positioned on one side of the antenna device 30, and more particularly to the side which is closest to the tissue targeted for ablation (e.g., angular component side). The tuning stub 63 is also arranged to partially cover or surround the antenna enclosure 37. By way of example, the tuning stub 63 may cover between about 25% to about 50% of the perimeter of the antenna enclosure 37. Furthermore, the length L of the tuning stub 63 may be adjusted to further improve the radiation efficiency of the antenna device 30. For example, by increasing the length L, less power is reflected at the entrance of the antenna device 30 and the radiation efficiency of the system is increased. The radiation efficiency of the antenna device 30 is maximized when the resonance frequency is the same as the electromagnetic signal produced by the generator (2.45 GHz for example).

Figure 8:
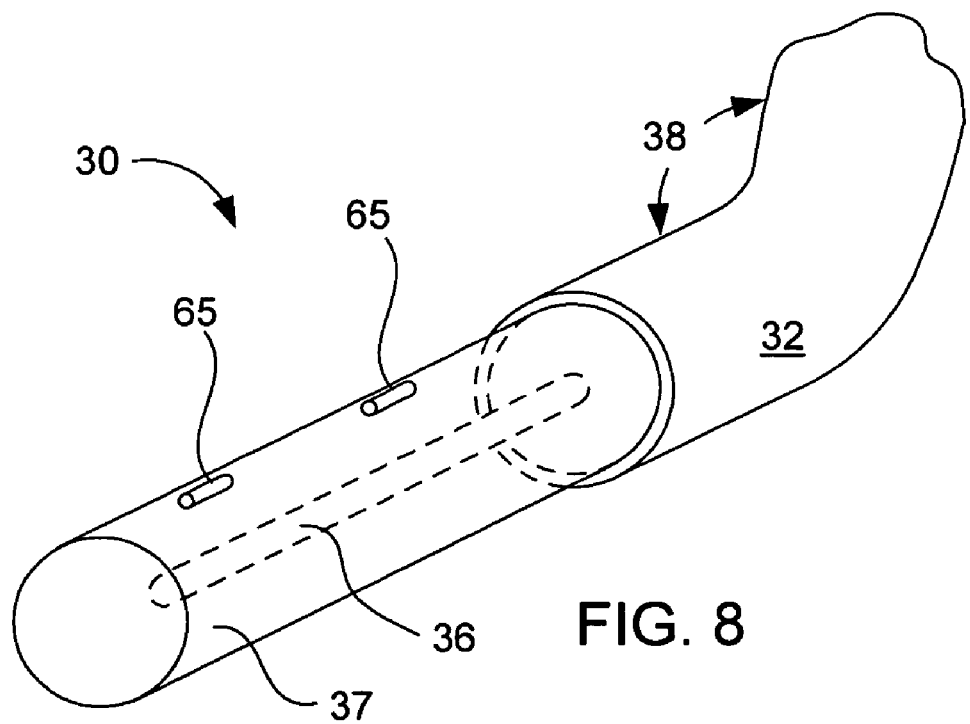
FIG. 8 is a perspective view of another embodiment of the antenna device.

In another embodiment, as shown in FIG. 8, the antenna device 30 includes a pair of director rods 65 for improving the radiation efficiency of the antenna device 30. As shown, the director rods 65 are generally positioned on one side of the antenna device 30, and more particularly to the side which is closest to the tissue targeted for ablation (e.g., angular component side). The director rods 65 are disposed on the periphery of the antenna enclosure 37 and may be positioned anywhere along the length of the antenna device 30. By way of example, one of the director rods 65 may be positioned proximate the distal end of the antenna device 30, while the other director rod 65 may be positioned proximate the proximal end of the antenna device 30. The position of the director rods may be adjusted to further improve the radiation efficiency of the antenna device 30. The director rods are generally formed from a suitable metallic material such as silver, and may also be formed from any material, which is silver-plated, for example, silver plated stainless steel or silver plated copper. Furthermore, the size (length and width) of the director rods 65 may be adjusted to further improve the radiation efficiency of the antenna device 30. It should be appreciated that a pair of rods is not a limitation and that a single rod or more than a pair rods may be used.

One particular advantage of using microwave energy is that the antenna device does not have to be in contact with targeted tissue in order to ablate the tissue. This concept is especially valid for cardiac ablation. For example, when a microwave antenna is located in the atrium, the radiated electromagnetic field does not see an impedance change between the blood and the myocardium (since the complex permittivity of these two media are similar). As a result, almost no reflection occurs at the blood-myocardium interface and a significant part of the energy will penetrate in the tissue to produce the ablation. In addition, the circulating blood between the antenna device and the tissue to be ablated helps to cool down the tissue surface. As such, the technique is potentially safer since it is less prone to create coagulation and/or carbonization. By way of example, a non-contact distance of about 1 to about 2 mm may be used. Furthermore, although not having contact provides certain advantages it should be noted that this is not a limitation and that the antenna device, and more particularly the antenna enclosure, may be positioned in direct contact with the tissue to ablate.

Furthermore, as is well known to those skilled in the art, it is more difficult to ablate tissues when the antenna device is surrounded by air. That is, there is a strong difference in the physical properties (the complex permittivity) between tissue and air. Therefore, in one embodiment, when the antenna device is not directly touching the tissue to be ablated, the surrounding cavity is filled with a liquid before ablating the tissue. As a result of filling the cavity with liquid, a better ablation may be achieved that is potentially safer since it is less prone to create coagulation and/or carbonization. By way of example, liquids such as isotonic saline solution or distilled water may be used.

Figure 9A:
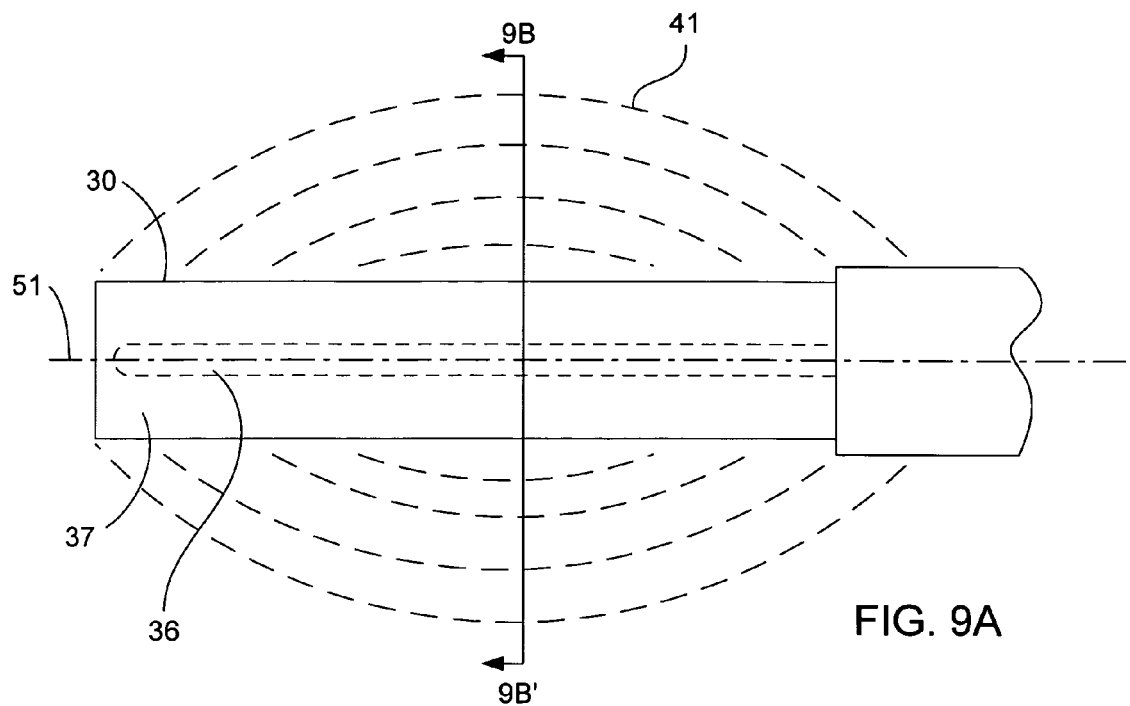
FIG. 9A is a side cross sectional view of the antenna device of FIG. 2 while it is generating a concentrated electromagnetic field, in accordance with one embodiment of the present invention.
Figure 9B:
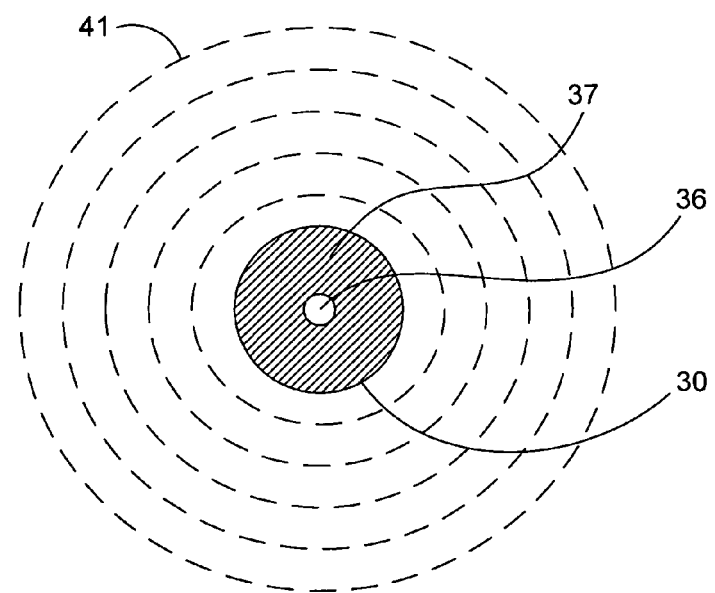
FIG. 9B is a front cross sectional view of the antenna device of FIG. 2 while it is generating a concentrated electromagnetic field, in accordance with one embodiment of the present invention.

In some embodiments, as shown in FIGS. 9A & 9B, the antenna device 30 is adapted to deliver electromagnetic energy (e.g., microwave) in directions extending substantially radially perpendicularly from the longitudinal axis 51 of the antenna wire 36 and through the antenna enclosure 37. That is, the antenna device 30 generally produces a radial isotropic radiation pattern 41 wherein the generated energy is homogeneously distributed around its volume. By way of example, the radiation pattern 41 generated by the antenna device 30 generally has an ellipsoidal shape along the length of the antenna device 30 (as shown in FIG. 9A), and a circular shape around its width (as shown in FIG. 9B).

It should be appreciated, however, that other ablative patterns may be needed to produce a particular lesion (e.g., deeper, shallower, symmetric, asymmetric, shaped, etc.).

Accordingly, the antenna device may be arranged to provide other ablative patterns. For example, the antenna device may be arranged to form a cylindrical ablative pattern that is evenly distributed along the length of the antenna, an ablative pattern that is directed to one side of the antenna device, an ablative pattern that supplies greater or lesser energy at the distal end of the antenna device and/or the like. Several embodiments associated with adjusting the ablative pattern of the antenna device will now be described in detail.

In one embodiment, the thickness of the antenna enclosure is varied along the longitudinal length of the antenna device in order to adjust the radiation pattern of the electromagnetic field to produce a better temperature profile during ablation. That is, the antenna enclosure thickness can be used to improve field characteristics (e.g., shape) of the electromagnetic field. As a general rule, a thicker enclosure tends to cause a decrease in radiation efficiency, and conversely, a thinner enclosure tends to cause an increase in radiation efficiency. Thus, by varying the thickness along the length of the antenna, the amount of energy being delivered to the tissue can be altered. As such, the thickness can be varied to compensate for differences found in the tissue being ablated. In some cases, the antenna device can be configured to deliver a greater amount of energy to a specific area and in other cases the antenna device can be configured to deliver energy more uniformly along the length of the antenna. For instance, if the delivered energy at the proximal end of the antenna is greater than the energy at the distal end, then the thickness of the dielectric material can be increased at the proximal end to reduce the radiation efficiency and therefore create a more uniform radiation pattern along the antenna. Consequently, a more uniform heating distribution can be produced in the tissue to ablate.

Figure 10:
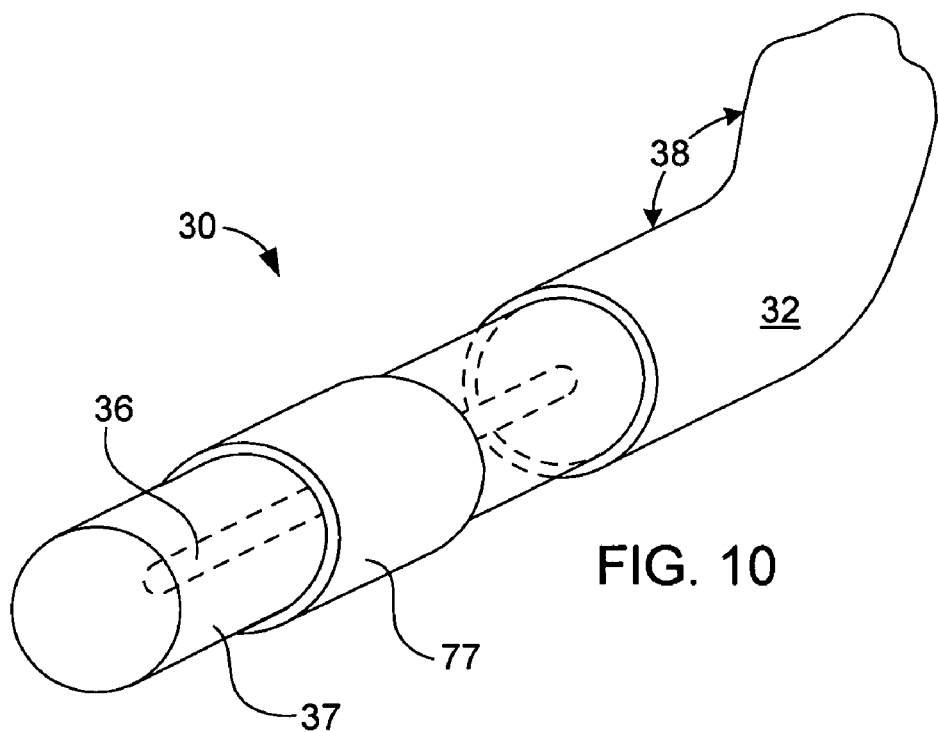
FIG. 10 is a perspective view of another embodiment of the antenna device.

In an alternate implementation of this embodiment, as shown in FIG. 10, the antenna device 30 includes a tuning sleeve 77 for altering the radiation pattern of the antenna device 30. The tuning sleeve 77 is formed from a suitable dielectric material and is arranged to increase the thickness of the antenna enclosure 37. By way of example, the tuning sleeve may be formed from the same material used to form the antenna enclosure. In some embodiments, the tuning sleeve 77 is integrally formed from the antenna enclosure 37 and in other embodiments, the tuning sleeve 77 is coupled to the antenna enclosure 37. Furthermore, the tuning sleeve 77 is disposed around the periphery of the antenna enclosure 37 and may be positioned anywhere along the length of the antenna device 30. By way of example, the tuning sleeve may be positioned at the proximal end or distal end of the antenna device, as well as anywhere in between the proximal and distal ends of the antenna device. As should be appreciated, the position and length of the tuning sleeve 77 may also be adjusted to alter the radiation pattern of the antenna device. Although the tuning sleeve is shown as surrounding the antenna enclosure, it should be noted that it may also be circumferentially segmented. In addition, it should also be understood that a single sleeve is not a limitation and that a plurality of sleeves may be used.

In some embodiments, the tip of the antenna wire can be exposed to further alter the field characteristics. An exposed tip generally produces "tip firing", which can be used to produce more energy at the distal end of the antenna. In other embodiments, the stub tuner may be used to alter the radiation pattern of the antenna device. In other embodiments, the director rods may be used to alter the radiation pattern of the antenna device.

Figure 11:
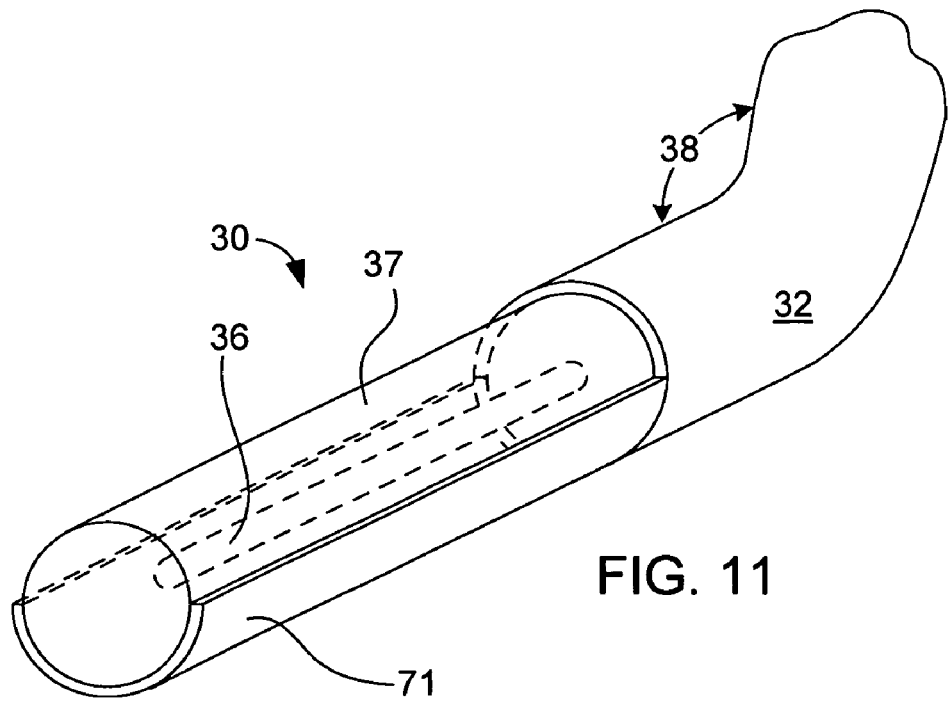
FIG. 11 is a perspective view of another embodiment of the antenna device.

In another embodiment, as shown in FIG. 11, the antenna device 30 includes a reflector 71, which is arranged to direct a majority of an electromagnetic field to one side of the antenna wire 36 and thus to one side of the antenna device 30. In this embodiment, the reflector 71 is positioned laterally to a first side of the antenna wire 36 and is configured to redirect a portion of the electromagnetic field that is transmitted towards the reflector 71 to a second side of the antenna wire 36 opposite the reflector 71. Correspondingly, a resultant electromagnetic field including a portion of the generated and a portion of the redirected electromagnetic field is directed in a desired direction away from the second side of the antenna wire 36. The desired direction is preferably in a direction towards the tissue to be ablated and thus the reflector is disposed on the side of the antenna device opposite the direction set for ablation. Furthermore, the reflector is disposed substantially parallel to the antenna to provide better control of the electromagnetic field during ablation.

The reflector is generally coupled to the outer conductor of the transmission line. Connecting the reflector to the outer conductor serves to better define the electromagnetic field generated during use. That is, the radiated field is better confined along the antenna, to one side, when the reflector is electrically connected to the outer conductor of the transmission line. The connection between the reflector and the outer conductor may be made in any suitable manner such as soldering, brazing, ultrasonic welding or adhesive bonding. In other embodiments, the reflector can be formed from the outer conductor of the transmission line itself. This is typically more difficult from a manufacturing standpoint but has the advantage of forming a more rugged connection between the reflector and the outer conductor. In other embodiments, metallization techniques are used to apply a reflective surface onto the antenna enclosure.

As can be appreciated, by those familiar with the art, by forming a concentrated and directional electromagnetic field, deeper penetration of biological tissues may be obtained during ablation and the biological tissue targeted for ablation may be ablated without heating as much of the surrounding tissues and/or blood. Further, since the radiated power is not lost in the blood, less power is generally required from the power source, and less power is generally lost in the transmission line. Additionally, this arrangement may be used to form linear lesions that are more precise.

Furthermore, the reflector 71 is typically composed of a conductive, metallic mesh or foil. One particularly suitable material is silver plated copper. Another suitable arrangement may be a stainless steel mesh or foil that has a layer of silver formed on its inner peripheral surface. However, it should be understood that these materials are not a limitation. Furthermore, the actual thickness of the reflector may vary according to the specific material chosen.

The reflector 71 is configured to have an arcuate or meniscus shape (e.g., crescent), with an arc angle that opens towards the antenna wire 36. Flaring the reflector 71 towards the antenna wire 36 serves to better define the electromagnetic field generated during use. The arc angle is typically configured between about 90° to about 180°. By way of example, an arc angle of about 120° works well. Additionally, it has been found that if the arc angle 90 is greater than 180° the radiation efficiency of the antenna arrangement decreases significantly.

Turning now to FIGS. 12A & 12B, an alternative embodiment to the present invention is illustrated wherein a metallic needle shaft 44 is used as an electrical continuation of the outer conductor 32. In this embodiment, the outer conductor 32 includes a contact member 60 that is disposed at the distal end of the outer conductor 32. The contact member 60 is arranged to electrically couple the outer conductor 32 to the needle shaft 44 when the ablation tool is moved through the probe 12, and more particularly when the ablation tool reaches its deployed position (as shown in FIG. 12B). Furthermore, the distal portions of the transmission line 28 are appropriately sized such that only the dielectric material medium 33 and the inner conductor 31 are slidably received in the lumen 22 of the metallic needle shaft 44. That is, a distal portion of the outer conductor 32 has been removed so that the outer conductor 32 is not carried by the lumen 22 of the needle shaft 44. As such, the contact member 60 is adapted to contact the distal end 46 of the needle shaft 44. By providing an electrical connection, the metallic needle shaft 44 can act as an extension of the outer conductor 32 of the transmission line 28.

For ease of discussion, portions of the ablation tool 24 that are disposed proximally from the contact member 60 are designated with an A, and portions of the ablation tool 24 that are disposed distally from the contact member 60 are designated with a B. Accordingly, the assembly comprising the inner conductor 31B, the dielectric material 33B and the metallic needle shaft 44 creates a distal coaxial cable 28B. That is, the needle shaft 44 conductively functions as a shield for the transmission line 28 from the access opening 46 to the distal penetration opening 47 of the probe 12. As best viewed in FIG. 12B, this shielding effect commences when the outer conductor 32 of the transmission line 28 and the needle shaft 44 of the probe 12 are in conductive communication with one another. The outer conductor 32 must therefore be in conductive communication with the metallic needle shaft 44 at least when the antenna device 30 is radiating electromagnetic energy.

As shown in FIG. 12B, the contact member 60 is adapted to electrically contact the proximal part 46 of the needle shaft 44 when the antenna device 30 is fully extended through the needle shaft 44 and into the targeted organ 18. Thus, the contact member 60 not only operates as an electrical connector between the outer conductor 32 and the needle shaft 44 but also as a stop device that limits the amount of penetration into the organ. In most configurations, the size of the contact member 60 is merely larger than that of the access opening.

As it was explained earlier, it is also important to match the impedance of the antenna with the impedance of the transmission line. As is well known to those skilled in the art, if the impedance is not matched to the transmission line, the microwave power is reflected back to the generator and the overall radiation efficiency tends to be well below the optimal performance. Accordingly, the dimensions of the distal coaxial cable elements are generally selected to match the impedance of the proximal transmission line. As should be appreciated, the cross sectional dimensions of 28B, 31B and 33B may be different from 28A, 31A and 33A.

With regards to the length of the antenna device 30, in the configuration of FIGS. 12A&B, the length is generally defined from the center of the distal penetration opening 47 to the distal end of the antenna wire 36. Several important factors that will influence the antenna length include the desired length of the ablation, the antenna configuration, the frequency of the electromagnetic wave and the impedance match of the antenna within the tissue or the organ cavity. The matching of the antenna is performed by adjusting its length so that the radiation efficiency is adequate when the antenna is used in the tissue or in the organ cavity. As an example, the radiation efficiency is generally adequate when the return loss of the antenna is in the range of −10 dB to −13 dB at 2.45 GHz. Instruments having specified ablation characteristics can be designed by varying the antenna length. For example, in microwave coronary applications for treating atrial fibrillation, the antenna device may have an antenna wire diameter of about 0.013 inch, a dielectric material medium diameter of about 0.050 inch and a length in the range of approximately 20 mm to 30 mm.

The distal coaxial cable can also be used as a serial stub tuner to match the impedance of the antenna device 30 and the transmission line 28. This arrangement is advantageous since, while maintaining the electrical continuation and the impedance match between the generator and the antenna, the diameters of the inner conductor 31 and the dielectric material medium 33 can be maximized relative the insert passage 22. The larger diameters, consequently, facilitate axial penetration into the organ due to the increased lateral and axial rigidity without compromising the impedance matching of about fifty (50) ohms.

Turning now to FIGS. 13A & 13B, an alternative embodiment to the present invention is illustrated wherein the ablation assembly 10 includes a clamping portion 79 for positioning the antenna device 30 proximate the wall 82 of the organ 18. The clamping portion 79 and the antenna device 30 are arranged to facilitate linear positioning of the antenna device 30. The clamping portion 79 generally includes a clamping finger 81 and a bar slide 84 that is slidably coupled to the needle shaft 44 and is configured to move relative to the probe 12. In general, the bar slide 84 is configured to slide within at least one guide track 86 that is structurally attached to the needle shaft 44. The clamping portion 79 is also arranged to be substantially aligned (in the same plane) with the antenna device 30 when the antenna device 30 is in its angular position.

Accordingly, when the antenna device 30 is properly positioned, the clamping portion 79 is moved in a direction towards the organ 18 to pinch the organ wall between the antenna 30 and the clamping finger 81. That is, the clamping finger 81 is moved to a position that contacts the outer wall 88 of the organ 18, wherein after contact and upon further finger movement the antenna device 30 is forced to move in a direction towards the probe 12. As a result, the antenna device 30 and clamping finger 81 exert opposite forces on opposite sides of the organ wall. By way of example, the finger and the antenna device can be used to sandwich the myocardium of the heart wherein the finger is applying a force to the epicardial surface and the antenna device is applying an opposing force to the endocardium. This particular approach tends to create a more uniform ablating surface, which as result, produces a better linear lesion.

The clamping finger is generally configured to be parallel to the angular position of the deployed antenna device. By way of example, if the antenna device is configured to have an angle of about 60 degrees relative to the axis of the probe, then the finger may be configured to have an angle of about 60 degrees relative to the axis of the probe. In this manner, the antenna device and clamping finger can pinch the organ wall evenly. Alternatively, the clamping finger can be shaped to conform to the shape of the outer wall. Further still, the clamping finger generally has a length that is substantially equivalent to the length of the antenna device. However, it should be noted that the length may vary according to the specific design of each ablation assembly. Additionally, the slide bar may be connected to a handle for physically actuating the linear movement, a knob or jack for mechanically actuating the linear movement, or an air supply for powering the linear movement. A locking mechanism may also be used to lock the engagement between the clamp finger and the antenna device so that the antenna device does not move from the target area during ablation.

Moreover, a seal may be used between the clamp finger and the outer wall of the organ to seal the puncture site. Additionally, a suction device may be disposed on the clamping finger to anchor and temporarily position the clamping finger to the outer organ wall. Alternatively, a balloon that is attached to the probe may be used to pinch the organ wall between the inflated balloon and the angularly positioned antenna device.

Turning now to FIGS. 14A & 14B, an alternative embodiment to the present invention is illustrated wherein the ablation assembly 10 includes a ground plane 89 for coupling electromagnetic energy 90 through the organ wall 35. The ground plane 89 generally provides a metallic surface that attracts the electric field generated by the antenna device 30 and therefore a more intense electromagnetic field 90 is produced between the antenna device 30 and the ground plane 89. Accordingly, the electromagnetic field 90 emitted by the antenna device 30 is more constrained in the tissue 35 between the antenna device 30 and the ground plane 89, which as a result helps to create the ablation.

As will be appreciated by those familiar with the art, inserting the tissue to ablate between the ground plane 89 and the antenna 30 has several potential advantages over conventional antenna structures. For example, by forming a concentrated electromagnetic field, deeper penetration of biological tissues may be obtained during ablation and the biological tissue targeted for ablation may be ablated without heating as much of the surrounding tissues and/or blood. Further, since the radiated power is not lost in the blood, less power is generally required from the power source, and less power is generally lost in the transmission line, which tend to decrease its temperature. Additionally, this arrangement may be used to form lesions that are more precise.

In this embodiment, the ground plane 89 is electrically coupled to the outer conductor 32 of the transmission line 28. The ground plane 89 is generally disposed on the needle shaft 44 of the probe 12 at a predetermined distance Q away from the deployed antenna device 30 (as shown in FIG. 14B). The predetermined distance Q is arranged to place the ground plane 89 in close proximity to the antenna device 30, and outside the outer wall of the organ 18 when the needle shaft 44 is position inside the organ wall 35. By way of example, in coronary applications, a distance between about 1 mm and about 15 mm may be used.

Moreover, the ground plane 89 is generally configured to be parallel to the angular position of the antenna device 30. By way of example, if the antenna device 30 is configured to have an angle of about 60 degrees relative to the axis of the probe, then the ground plane may be configured to have an angle of about 60 degrees relative to the axis of the transmission line. In this manner, the antenna and the ground plane can couple energy more evenly. Alternatively, the ground plane can be shaped to conform to the shape of the outer wall. Further still, the ground plane generally has a length that is substantially equivalent to the length of the antenna device 30. By way of example, a ground plane length between about 20 mm and about 50 mm works well. It should be noted, however, that the length may vary according to the specific needs of each ablation assembly. The ground plane is also arranged to be substantially aligned (in the same plane) with the angular component of the antenna device 30.

The ground plane 89 may be formed from a wire, strip or rod, and may be arranged to have a circular, rectangular, or other cross section shape. Furthermore, the ground plane 89 is formed from a suitable conductive material such as stainless steel or silver. The dimensions of the ground plane 89 may vary to some extent based on the particular application of the ablation assembly and the type of material chosen. Additionally, the ground plane may be printed on or enclosed inside of a flexible dielectric substrate (such as Teflon or polymide). Furthermore, the connection between the ground plane 89 and the outer conductor 32 may be made in any suitable manner such as soldering, brazing, ultrasonic welding or adhesive bonding.

The ground plane 89 can be configured in a variety of ways. In some embodiments, the ground plane may be rigidly or structurally coupled to the needle shaft of the probe. In other embodiments, the ground plane may be pivoted or slidably coupled to the needle shaft of the probe. For example, the clamping finger, as described above in FIG. 13, can be arranged to be a ground plane for the antenna. In other embodiments, the ground plane may be flexible in order to follow the natural curvature of the organ. In other embodiments, the ground plane may be biased to contact the tissue. Further still, in some embodiments, the ground plane may be configured to act as a stop device that limits the amount of probe penetration into the organ.

In an alternate embodiment, the ground plane may be properly positioned across from the antenna device with a ground plane positioner. The ground plane positioner generally includes tubular member having passage therein. In this embodiment, the ground plane is advanced longitudinally through the passage of the tubular member to the distal opening of the passage. Upon subsequent advancement, the ground plane may be manipulated to extend through distal opening of the passage and to the outer wall of the organ. Such advancement preferably allows the ground plane to assume a predetermined position that is substantially aligned with the deployed antenna device such that the organ wall is disposed between the ground plane and the antenna device. In one embodiment, the assembly may include a biasing member that is specifically formed and shaped for urging the ground plane to a predetermined bent position. In another embodiment, the assembly may include a steering system for bending the ground plane to a predetermined bent position. In another embodiment, the needle shaft of the tubular member can be prebent or curved to direct the ground plane to its advanced position.

Figure 15:
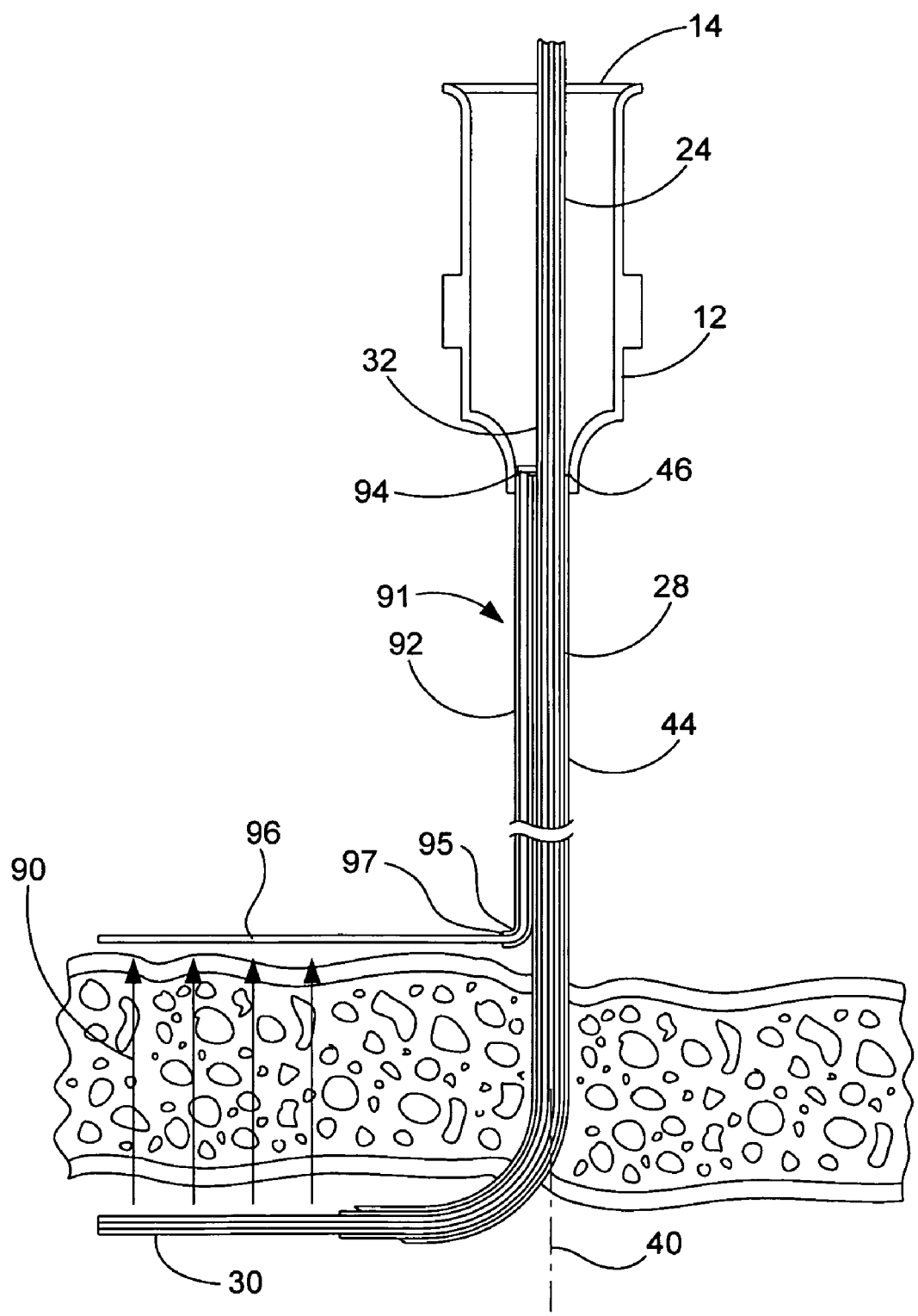
FIG. 15 is a side elevation view, in cross section, of another embodiment of the ablation assembly, in accordance with one embodiment of the present invention.

Referring to FIG. 15, the ablation assembly 10 includes a positioner 91 having a tubular member 92 and a passage 94 therein. As mentioned above, the ground plane 96 is electrically coupled to the outer conductor 32 of the transmission line 28. In this particular embodiment, the tubular member includes a curved section 95 which redirects the position of the ground plane 96 in a manner skewed from the axis 40 of the proximal end 14 of the probe 12. As the distal end of the ground plane 96 contacts the curved wall 95 of the passage 94, the ground plane 96 is urged out of the distal opening 97 and to an outer wall position that is substantially aligned with the angled antenna device 30. Additionally, the ground plane 96 may be fixed to the transmission line 28 such that when the antenna device 30 is deployed so is the ground plane 96.

Figure 16:
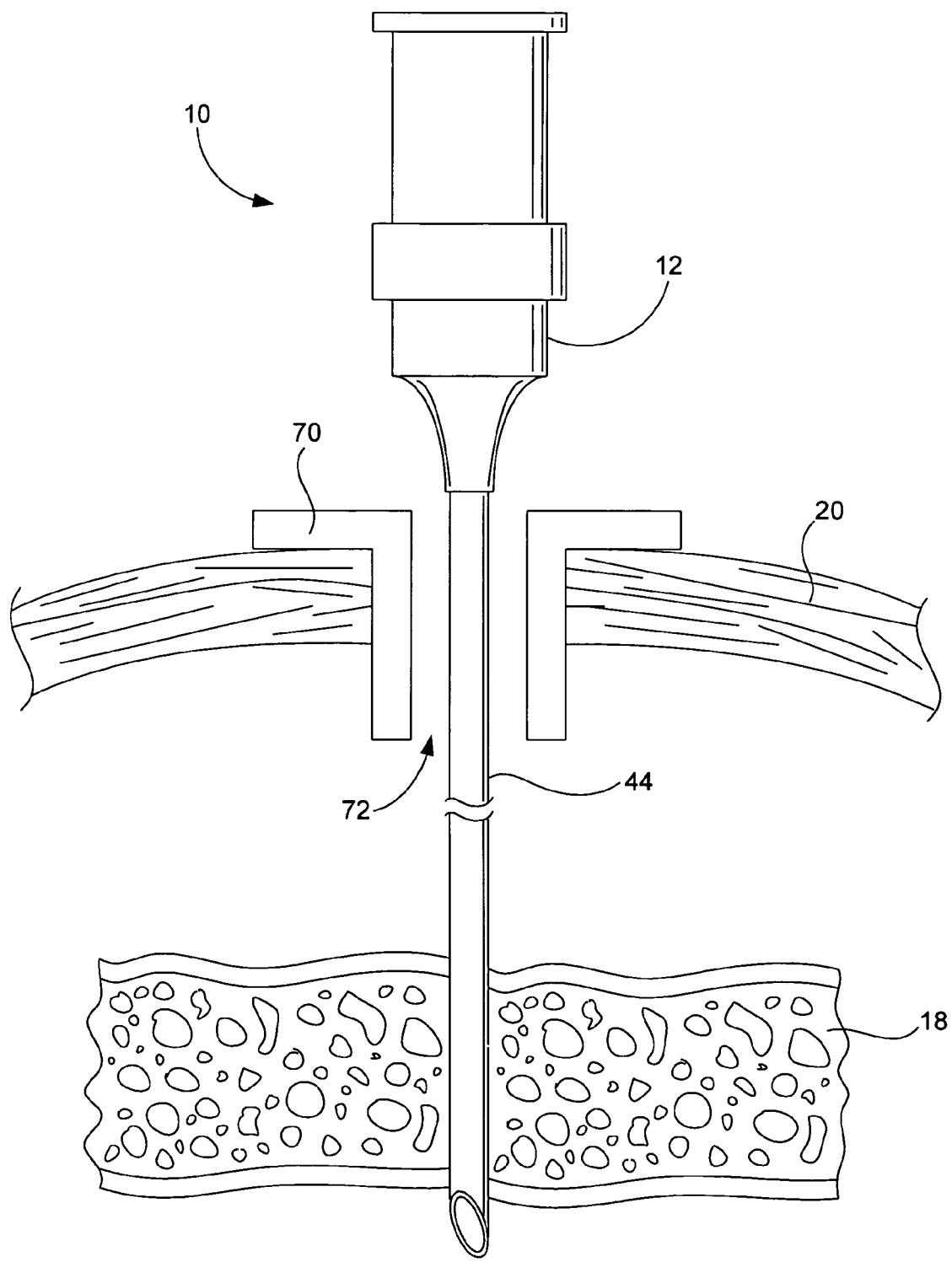
FIG. 16 is a side elevation view, in cross section, of a probe inserted through an access device positioned in the body cavity and penetrating a body an organ, in accordance with one embodiment of the present invention.

Turning now to FIG. 16, an alternative embodiment to the present invention is illustrated wherein the ablation assembly 10 is inserted through an access device 70, which is positioned in the body cavity 20. The access device 70 is generally disposed inside a small incision that is made in the body cavity 20. The access device includes a passage 72 that is appropriately sized for receiving the ablation assembly 10 such that the needle shaft 44 of probe 12 can be introduced into the body cavity 20. As can be appreciated, the passage 72 allows access to the targeted organ 18. Access devices are well known to those skilled in the art and therefore they will not be described in detail herein.

Figure 17:
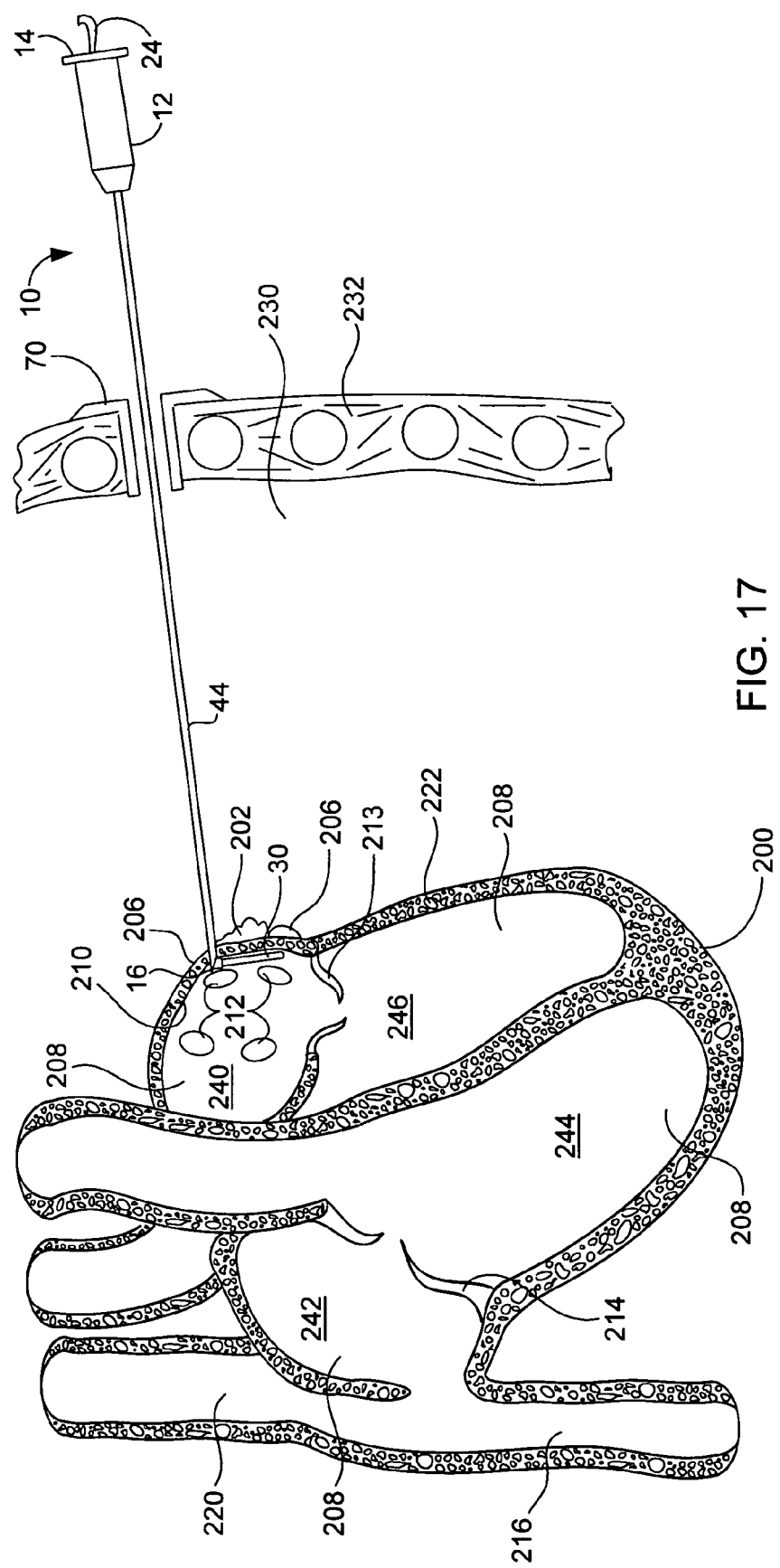
FIG. 17 is a side elevation view showing a cardiac procedure using the ablation assembly of FIGS. 1-3, in accordance with one embodiment of the present invention.
Figure 18:
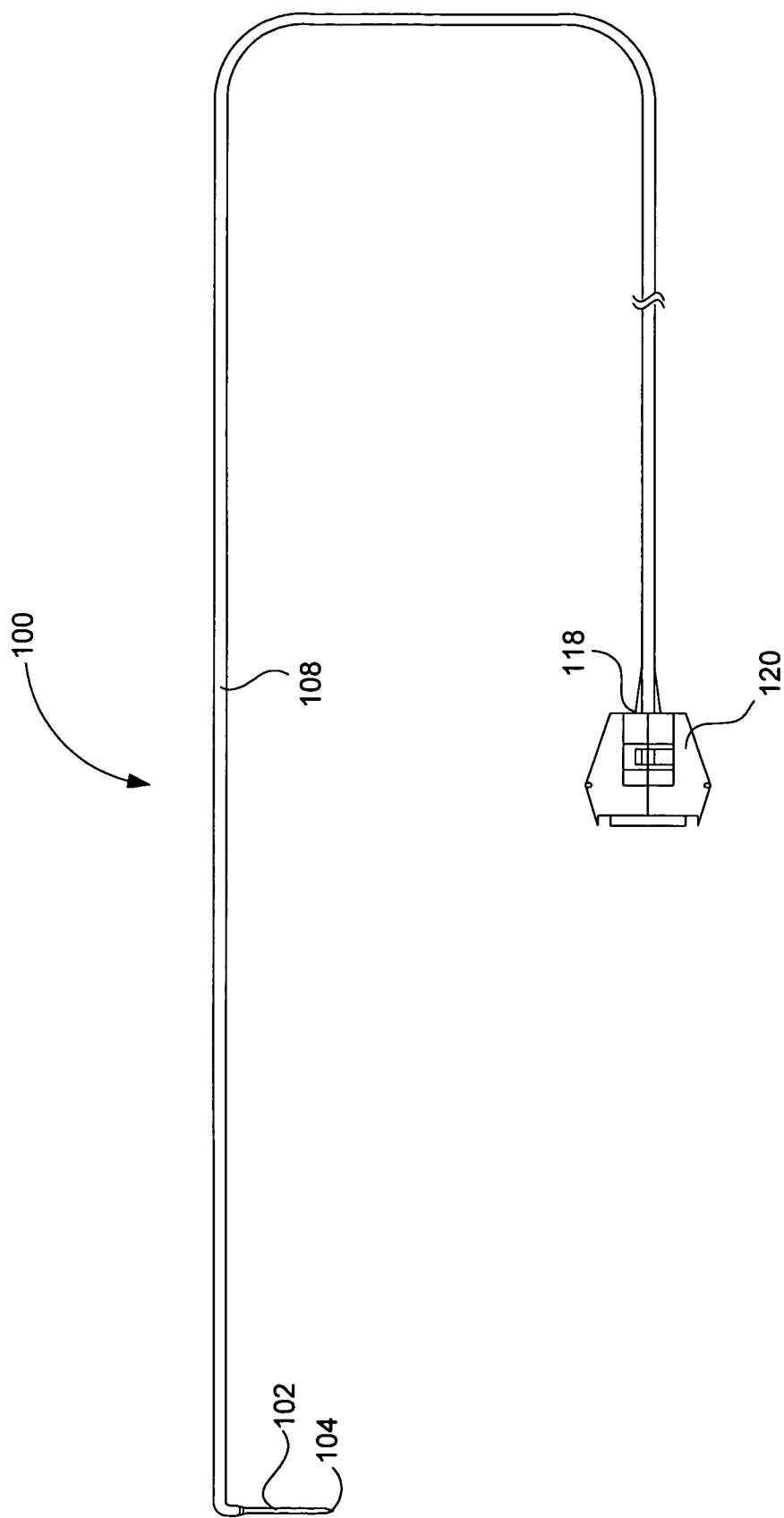
FIG. 18 is a top plan view of an ablation assembly having a needle antenna, in accordance with one embodiment of the present invention.

Referring now to FIG. 17, the described ablation assembly 10 is used for ablating cardiac tissues, in accordance with one embodiment of the present invention. The ablation assembly 10 is especially beneficial in navigating around certain regions of the heart 200. For example, the ablation assembly 10 may be used to bypass the layers of fat 202 or veins 204 that surround the epicardial surface 206 (e.g., outer wall) of the heart 200. By way of example, the vein 204 may be the coronary sinus, which is located just superior to the junction between the left atrium 240 and the left ventricle 246. As mentioned, fat 202 is a good microwave absorber and a very poor thermal conductor. Furthermore, veins 204 readily transfer heat through blood flow. As a result, fat 202 and veins 204 are very difficult to ablate through from the epicardial surface (not enough thermal energy to ablate). Accordingly, by positioning the antenna device 30 inside a cavity 208 of the heart 200 (e.g., through the layer of fat), the ablative energy can be supplied to the endocardium 210 rather than the obstructed epicardial surface 206 thereby effectively ablating the targeted tissue. By way of example, the cavity 208 may be the left atrium 240, the right atrium 242, the left ventricle 246 or the right ventricle 244.

The ablation assembly 10 may be used to treat a variety of heart conditions. In one embodiment, the ablation assembly is used to treat atrial fibrillation and in another embodiment the ablation assembly is used to treat atrial flutter. Several implementations associated with ablating cardiac tissues using the ablation assembly 10 will now be described.

In one implementation, the ablation assembly 10 is used to create lesions between any of the pulmonary veins 212 of the heart 200 in order to treat atrial fibrillation. In another implementation, the ablation assembly 10 is used to create lesions from one of the pulmonary veins 212 to the mitral valve 213 of the heart 200 in order to avoid macro-reentry circuit around the pulmonary veins in a lesion pattern used to treat atrial fibrillation. In another implementation, the ablation assembly 10 is used to create lesions from one of the pulmonary veins 212 to the left atrial appendage of the heart 200 also to avoid macro-reentry circuit around the pulmonary veins in a lesion pattern used to treat atrial fibrillation.

In one implementation, the ablation assembly 10 is used to create lesions between the inferior caval vein 216 to the tricuspid valve 214 of the heart 200, in order to treat typical or atypical atrial flutter. In another implementation, the ablation assembly 10 is used to create lesions along the cristae terminalis in the right atrium 242 of the heart 200 in order to treat typical or atypical atrial flutter. In another implementation, the ablation assembly 10 is used to create lesions from the cristae terminalis to the fossae ovalis in the right atrium 242 of the heart 200 in order to treat typical or atypical atrial flutter. In yet another implementation, the ablation assembly 10 is used to create lesions on the lateral wall of the right atrium 242 from the superior 220 to the inferior vena cava 216 in order to treat atypical atrial flutter and/or atrial fibrillation.

Although a wide variety of cardiac procedures have been described, it should be understood that these particular procedures are not a limitation and that the present invention may be applied in other areas of the heart as well.

A method for using the described microwave ablation assembly in treating the heart will now be described with reference to FIG. 17. Although only a heart is shown and described, it should be understood that other organs, as well as organ ducts, may be treated with ablation assembly. The method includes providing an ablation assembly such as any one of the ablation assemblies described herein. More particularly, the method includes providing a surgical device 10 having a probe 12 and an elongated microwave ablation arrangement 24. The probe 12 includes a passage extending therethrough from a proximal end 14 to an opposite distal end 16 thereof. The distal end 16 is adapted to penetrate through a muscular wall 222 (e.g., myocardium) of the heart 200. Furthermore, the elongated microwave ablation arrangement 24 includes a distal antenna 30 coupled to a transmission line, which in turn is coupled to a microwave energy source at a proximal end thereof. In accordance with the present invention, the method includes introducing the surgical device 10 into a body cavity 230. This may be by penetration of the body 232 or through an access device 70. Several surgical approaches are possible. For example, the surgical device may be introduced through an open chest, a posterior thoracotomy, a lateral thoracotomy (as shown in FIG. 10), or a sternotomy. The surgical procedure can also use an endoscope in order to visualize the ablation device during the placement. These procedures are generally well known to those skilled in the art and for the sake of brevity will not discussed in detail.

The method further includes penetrating the muscular wall 222 of the heart 200 with the distal end 16 of the elongated probe 12 and introducing the elongated probe 12 through the muscular wall 222 of the heart 200 and into an interior chamber 208 thereof. By way of example, the surgical tool 10 can be introduced into the left atrium 240, the right atrium 242, the right ventricle 244 or the left ventricle 246. Furthermore, before penetration a purse string suture may be placed in the heart wall proximate the area targeted for penetration so as to provide tension during penetration. Purse string sutures are well known in the art and for the sake of brevity will not be discussed in more detail.

The method also includes introducing the elongated microwave ablation device 24 into the passage of the elongated probe 12 and advancing the antenna 30 past the distal end 16 of the probe 12 such that the antenna 30 is disposed inside the interior chamber 208 of the heart 200. Upon advancement, the antenna 30 preferably assumes a predetermined position that substantially matches the shape and/or angular position of the wall to be ablated. By way of example, the position may place the antenna substantially parallel to the interior surface 210 (e.g. endocardium) of the penetrated muscular wall 222 and proximate the targeted tissue. Angled advancement may be accomplished in a variety of ways, for example, with a biasing member, a steering wire or a curved probe. Furthermore, the method includes generating a microwave field at the antenna that is sufficiently strong to cause tissue ablation within the generated microwave field.

In accordance with another aspect of the present invention, the ablation assembly includes a needle and a transmission line having a longitudinal axis. The needle is adapted to be inserted into a body cavity and to penetrate an organ (or duct) within the body cavity. The needle is also configured for insertion into a cavity within the organ and includes an antenna for transmitting electromagnetic energy. The transmission line is coupled to the antenna and configured for delivering electromagnetic energy to the antenna.

Furthermore, the ablation assembly is arranged so that when the needle is finally inserted into the organ cavity, the antenna lies at an angle relative to the longitudinal axis of the transmission line. In most cases, the needle or the transmission line is pre-shaped or bent at a predetermined position that is arranged to substantially match the shape and/or angular position of the wall to be ablated. In other cases, a biasing member or steering system, in a manner similar to biasing member and steering system described above, may be used to provide angled positioning.

Turning now to FIGS. 18-21, an ablation assembly, generally designated 100, is provided including a relatively thin needle 102 configured for emitting electromagnetic energy and having a penetration end 104 adapted to penetrate an organ 106. The needle 102 is axially rigid to allow for tissue penetration and may be longitudinally flexible to avoid damaging the organ 106 during positioning. The ablation assembly 100 further includes a transmission line 108 having a longitudinal axis 110 and a distal end 112 that is coupled to the proximal end 114 of the needle 102 for generating an electromagnetic field sufficiently strong to cause tissue ablation. At the proximal end 118 of the transmission line 110 is an electrical connector 120 adapted to electrically couple the antenna to an electromagnetic energy source (not shown). As shown, the needle 102 is bent at an angle 116 relative to the longitudinal axis 110 of the transmission line 108. In most embodiments, the bend is arranged to easily position the antenna parallel to the tissue to ablate by taking into consideration the angle of approach (the angle used to insert the needle through the organ).

Accordingly, the ablation assembly 100 utilizes the needle 102 to provide ablative energy within a cavity of the organ 106. That is, the distal penetration end 104 is used to pierce through an outer wall 122 of the organ 106 to position the needle 102 proximate and substantially parallel to an inner wall 124 of the organ 106. Once the needle 102 is positioned, ablative energy that is sufficiently strong to cause tissue ablation is emitted from the needle 102 to ablate a portion of the inner wall 124. This arrangement is especially beneficial when the areas targeted for ablation have obstructions along the outer wall of the organ. For example, the needle may be used to bypass and navigate around layers of fat or veins that surround the epicardial surface (e.g., outer wall) of the heart. Furthermore, the angled position of the needle assures that the ablative energy will be accurately transmitted in the targeted ablation region.

Figure 21:
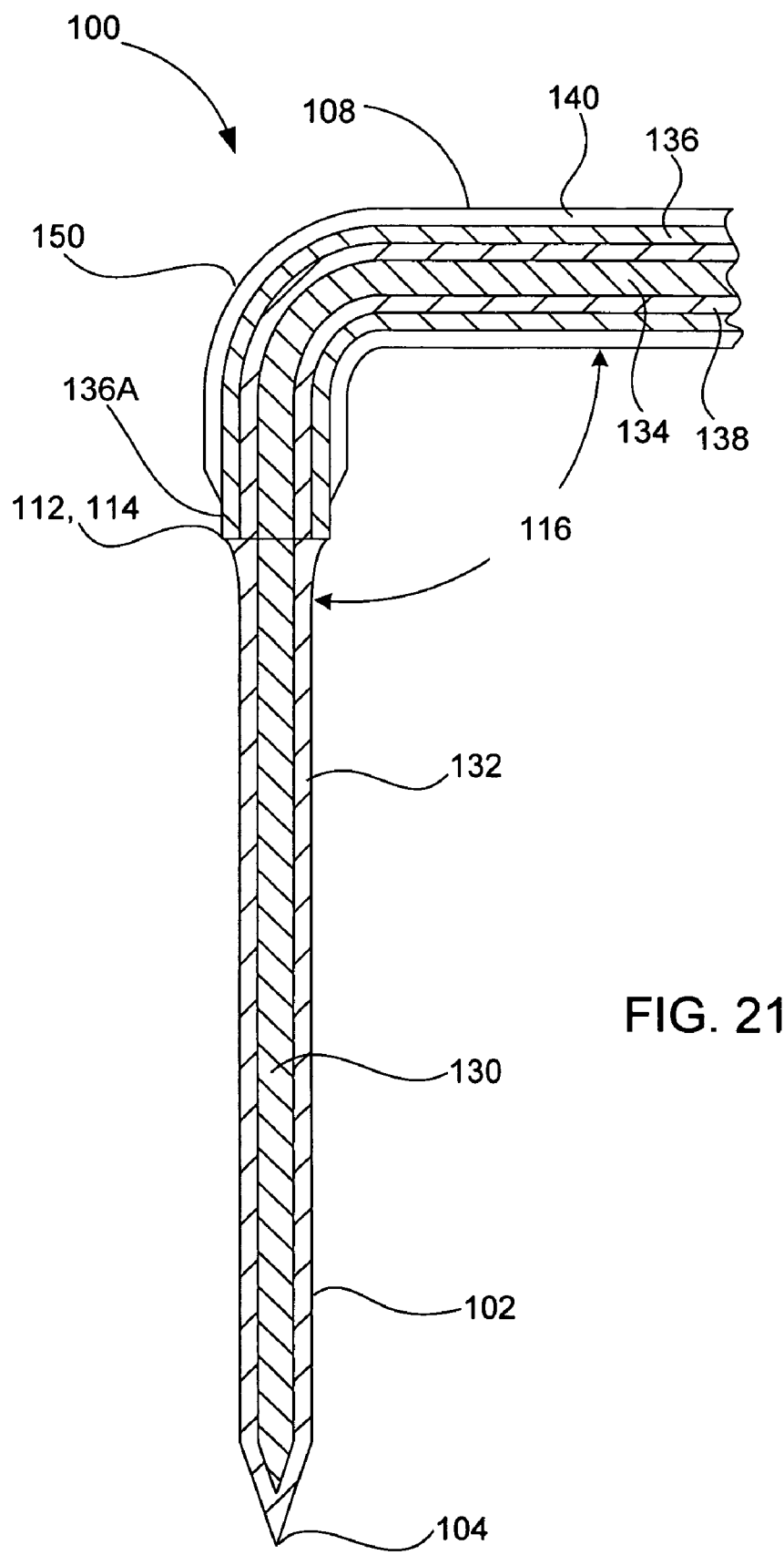
FIG. 21 is a side elevation view, in cross section, of a needle antenna, in accordance with one embodiment of the present invention.

Referring to FIG. 21, the needle 102 includes an elongated antenna 130 and an antenna enclosure 132 that are adapted to pierce through organ 106 at a distal penetration end 104. By way of example, the distal penetration end 104 is in the form of a conventional beveled tipped needle or a beveled point chamfered needle which forms sharp cutting edge. As shown, the antenna 130 is encapsulated by the antenna enclosure 132, which is generally better suited to remove the high electromagnetic field concentration that is normally obtained when the metallic part of the antenna is in direct contact with the tissue. A high field concentration can create a high surface temperature on the tissue to ablate which is not desirable, especially for cardiac applications. The antenna enclosure 132 may be made of any suitable dielectric material (e.g., low loss tangent) with low water absorption such as medical grade epoxy, polyethylene or Teflon type products (e.g., bio compatible). As was described in great detail above, it may be desirable to adjust the thickness of the antenna enclosure in order to provide better impedance matching between the antenna and the tissue targeted for ablation. It is contemplated, however, that needle antenna enclosures having a thickness between about 0.002 inches and about 0.015 inches, and more particularly about 0.005 inches work well.

It should also be noted that the antenna enclosure may not be required for all ablation assemblies. By way of example, FIGS. 22 & 24 show the ablation assembly 100 with an exposed antenna 130 having no antenna enclosure. However, it should be noted that in most situations the antenna enclosure is configured to insulate the antenna to avoid the charring and tissue destruction effects that are commonly experienced when the ablative elements, and more particularly, the metallic parts of the antenna, are directly in contact with the body's tissue or fluid.

The antenna 130 is formed from a conductive material. By way of example, spring steel, beryllium copper, or silver plated copper work well. Further, the diameter of the antenna 130 may vary to some extent based on the particular application of the ablation assembly and the type of material chosen. By way of example, in systems using a monopole type antenna, wire diameters between about 0.005 inch to about 0.020 inches work well. In the illustrated embodiment, the diameter of the antenna is about 0.013 inches.

As mentioned, the field generated by the antenna will be roughly consistent with the length of the antenna. That is, the length of the electromagnetic field is generally constrained to the longitudinal length of the antenna. Therefore, the length of the field may be adjusted by adjusting the length of the antenna. Accordingly, ablation arrangements having specified ablation characteristics can be fabricated by building ablation arrangements with different length antennas. By way of example, antennas having a length between about 20 mm and about 50 mm, and more particularly about 30 mm work well. Furthermore, the antenna shown is a simple longitudinally extending exposed wire that extends distally from the inner conductor. However it should be appreciated that a wide variety of other antenna geometries may be used as well. By way of example, helical coils, flat printed circuit antennas and other antenna geometries will also work well. Additionally, it should be understood that longitudinally extending antennas are not a requirement and that other shapes and configurations may be used. For example, the antenna may be configured to conform to the shape of the tissue to be ablated or to a shape of a predetermined ablative pattern for creating shaped lesions.

Referring back to FIG. 21, the transmission line 108 generally includes an inner conductor 134 and an outer conductor 136 separated by a dielectric material medium 138. An insulating sheath 140 is typically disposed around the outer conductor 136. Furthermore, the outer conductor 136 is generally arranged to have a portion 136A that extends from the distal end of the insulating sheath 140 so that it can be exposed. As mentioned, when the outer conductor 136 is exposed, the generated electromagnetic field is more constrained to the antenna and therefore the radiation efficiency tends to be greater. By way of example, an exposed outer conductor having a length of about 1 mm to about 2 mm works well. Although the outer conductor is shown and described as being exposed it should be understood that this is not a limitation and that the ablation arrangement can be made with or without an exposed outer conductor.

Furthermore, the transmission line 108 is provided by a conventional fifty (50) ohm coaxial design suitable for the transmission of microwave energy at frequencies in the range of about 400 to about 6000 megahertz. In the preferred embodiment, the inner conductor 134 is provided by a solid metallic material core surrounded by a flexible semi-rigid dielectric material medium 138. The outer conductor 136 includes a braided sleeve of metallic wires surrounding the inner conductor 134 to provide shielding and good flexibility thereof. Furthermore, the insulating sheath is generally flexible and may be made of any suitable material such as medical grade polyolefins, fluoropolymers, or polyvinylidene fluoride. By way of example, PEBAX resins from Autochem of Germany have been used with success.

In most embodiments, the proximal end 114 of the antenna 130 is coupled directly or indirectly to the distal end 112 of the inner conductor 134 of the transmission line 108. A direct connection between the antenna 130 and the inner conductor 134 may be made in any suitable manner such as soldering, brazing, ultrasonic welding or adhesive bonding. As was described in great detail above, it may be desirable to indirectly couple the antenna to the inner conductor through a passive component in order to provide better impedance matching between the antenna device and the transmission line. In other embodiments, the antenna 130 can be integrally formed from the transmission line 108 itself. This is typically more difficult from a manufacturing standpoint but has the advantage of forming a more rugged connection between the antenna and the transmission line.

The ablation assembly 100 is preferably thin having a diameter in the range of between about 1.5 mm to about 3 mm, and more preferably about 2 mm. This relatively small diameter size is particularly suitable for use in most bodily organs, such as the heart, so as to minimize the puncture diameter and, thus, potential bleeding. It will be appreciated, however, that the present invention may be used to ablate other organs or tissue as well. Additionally, the ablation assembly must be sufficiently flexible to accommodate normal operational use, yet be sufficiently rigid to prevent buckling of the line during penetrative manipulation of the needle into the targeted organ.

In one embodiment, the ablation assembly 100 includes a bend 150 that places the needle 102 at an angle relative to the longitudinal axis 108 of the transmission line 110. As shown in FIG. 21, the bend 150 is placed along a distal portion of the transmission line. Alternatively, the bend 150 may be placed along a proximal portion of the needle as shown in FIG. 23. In either case, the bend 150 is arranged such that when the needle 102 is introduced into the organ cavity, the needle is disposed at a predetermined position that is arranged to substantially match the shape and/or angular position of the wall to be ablated. That is, the needle is bent in a direction towards the tissue targeted for ablation. By way of example, the needle may be configured to be bent in a direction that places the needle substantially parallel and proximate the tissue to be ablated. Furthermore, bend 150 is arranged to be sufficiently rigid to prevent buckling of the line during penetrative manipulation of the needle into the targeted organ.

Figure 19:
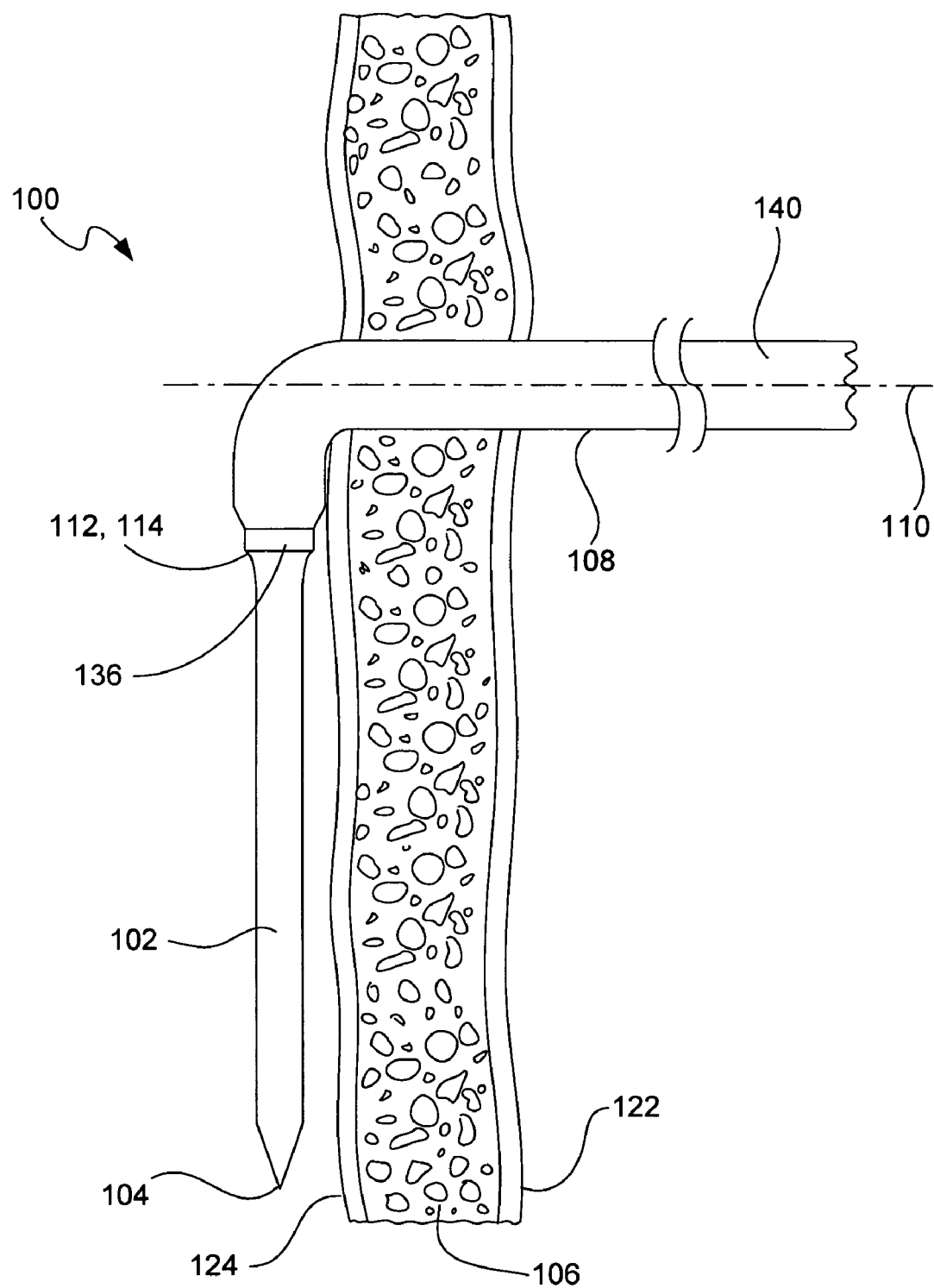
FIG. 19 is a side elevation view of the needle ablation assembly of FIG. 18 after penetrating an organ wall (in cross section), in accordance with one embodiment of the present invention.
Figure 20:
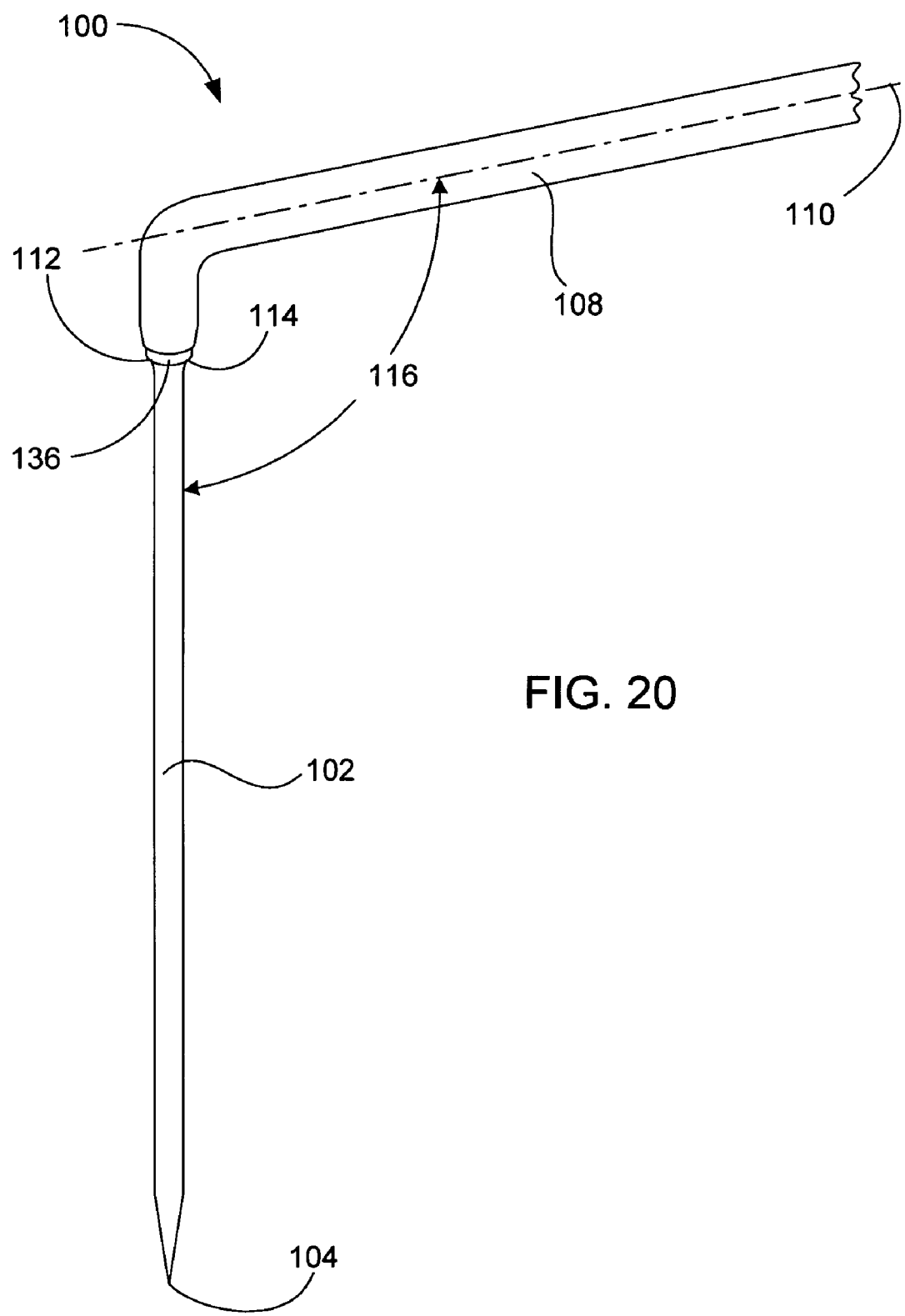
FIG. 20 is a perspective view of the needle ablation assembly of FIG. 18, in accordance with one embodiment of the present invention.

In FIG. 19, the ablation assembly 100 is shown perpendicularly penetrating the organ wall 106. It is contemplated, however, that this position is not always possible because some organs are particularly difficult to access, and therefore the needle may be inserted into the wall of the organ at different angles. Accordingly, the present invention may be configured to provide a range of angled bends. By way of example, an antenna position having an angle in the range of between about 45 degrees to about 135 degrees with respect to the longitudinal axis of the transmission line works well. However, it should be noted that this is not a limitation and that other angles, as well as other bend configurations, may be used. By way of example, the ablation assembly can be configured to have multiple bends, curvilinear bends, rectilinear bends, three dimensional bends or have a shape that conforms to the shape of the tissue to be ablated or the ablating line desired.

For ease of discussion, FIGS. 25A & 25B show a variety of ablation assembly configurations. FIG. 25A shows the needle 102 in an acute angular position relative to longitudinal axis 110. FIG. 25B shows the needle 102 in an obtuse angular position relative to longitudinal axis 110. Again, these angular positions are important parameters for ensuring that the antenna device is properly positioned in a direction towards the tissue targeted for ablation.

Figure 26:
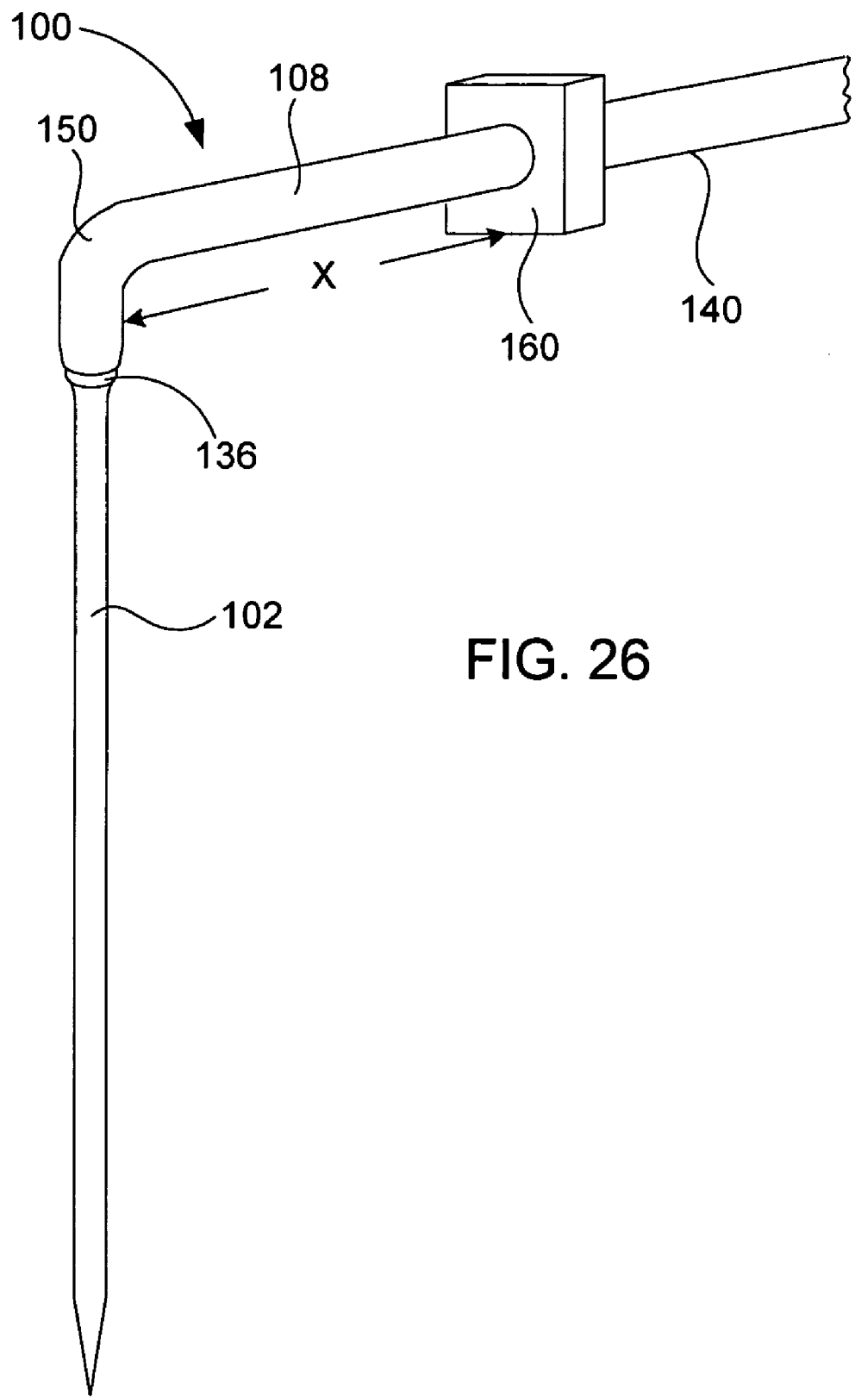
FIG. 26 is a perspective view of a needle antenna having a gripping block, in accordance with one embodiment of the present invention.

Turning now to FIG. 26, an alternative embodiment to the present invention is illustrated wherein the ablation assembly 100 includes a handle 160 that provides gripping surfaces for manipulating the needle 102 through the organ wall. The handle 160 is configured for receiving surgical tools such as forceps (not shown). In this manner, the needle 102 may be positioned in the organ by holding the handle 160 with forceps and maneuvering the forceps such that the needle 102 penetrates through the organ wall. Subsequently, the forceps may be used to position the needle 102 proximate the tissue targeted for ablation. The handle 160 is disposed on the transmission line 108 at a predetermined distance X away from the bent portion 150 of the assembly 100. The predetermined distance X is arranged to place the handle 160 in close proximity to the needle 102, and outside the outer wall of the organ when the needle 102 is positioned inside the organ. By way of example, in coronary applications, a distance between about 1 cm and about 3 cm works well. Furthermore, a handle formed from a polymer having a width between about 5 mm and about 10 mm, a length between about 2 mm and about 5 mm, and a height between about 5 mm and about 10 mm works well. Although the handle is shown as being rectangular it should be noted that this is not a limitation and that the handle can be arranged with a plurality of different shapes.

In one implementation, the handle is arranged to provide additional support (rigidity and strength) at the junction between the antenna and the inner conductor of the transmission line. In another implementation, the handle is arranged to enclose an impedance matching device located between the antenna and the inner conductor. Furthermore, in a manner analogous to the clamping portion (FIG. 13) described above, the handle can be arranged to be slidably coupled to the transmission line such that the handle can be used to clamp the wall of the organ between the bent needle and the handle. Additionally, a seal may be used between the handle and the outer wall of the organ to seal the puncture site. In another implementation, the handle may include a balloon for biasing contact between the handle and the bent antenna.

Turning now to FIGS. 27A-27C, an alternative embodiment to the present invention is illustrated wherein the ablation assembly 100 includes a ground plane strip 170 for coupling electromagnetic energy through the organ wall 106. The ground plane 170 generally provides a metallic surface that attracts the electric field generated by the antenna 130 and therefore a more intense electromagnetic field 180 is produced between the antenna 130 and the ground plane 170. As a result, a more efficient, controlled and concentrated electric field can be used to ablate the targeted tissue. Additionally, less power may be required from the power source because of the more efficient use of the energy.

In this embodiment, the ground plane 170 is electrically coupled to the outer conductor 136 of the transmission line 108. The ground plane 170 is generally disposed on the transmission line 108 at a predetermined distance Y away from the antenna 130 of the needle 102. The predetermined distance Y is arranged to place the ground plane in close proximity to the needle 102, and outside the outer wall of the organ 106 when the needle 102 is positioned inside the organ 106. By way of example, in coronary applications, a distance between about 1 mm and about 15 mm works well.

Additionally, the ground plane 170 must be sufficiently flexible to accommodate needle maneuvering, normal operational use and storage thereof, yet be sufficiently rigid to prevent buckling or bends in the ground plane when the needle is positioned inside the organ cavity. The ground plane 170 may be formed from a metallic foil. By way of example, silver, stainless steal or gold work well. The ground plane 170 can also be formed from a flexible dielectric substrate with one or two metallic surface(s). By way of example, Kapton™ or Teflon™ substrates work well. Further, the thickness of the ground plane 170 may vary to some extent based on the particular application of the ablation assembly and the type of material chosen. By way of example, a strip thickness between about 0.005 inch to about 0.040 inch works well. In the illustrated embodiment, the thickness of the ground plane strip is about 0.010 inch. Furthermore, the connection between the ground plane 170 and the outer conductor 136 may be made in any suitable manner such as soldering, brazing, ultrasonic welding or adhesive bonding.

Although the ground plane is shown and described as a strip it should be noted that this is not a limitation and that the ground plane may vary in form according to the specific needs of each assembly. By way of example, a metallic wire formed from silver having a diameter between about 1 mm and about 2 mm works well. Additionally, a plate formed from silver having a thickness between about 0.005 inch and about 0.040 inch and a width between about 2 mm and about 5 mm works well.

Moreover, the ground plane is generally configured to be parallel to the angular position of the needle 102. By way of example, if the needle is configured to have an angle of about 60 degrees relative to the axis of the transmission line, then the ground plane may be configured to have an angle of about 60 degrees relative to the axis of the transmission line. In this manner, the antenna and the ground plane can couple energy more evenly. Alternatively, the ground plane can be shaped to conform to the shape of the outer wall. Further still, the ground plane generally has a length that is substantially equivalent to the length of the antenna 130. By way of example, a ground plane length between about 20 mm and about 50 mm works well. It should be noted, however, that the length may vary according to the specific needs of each ablation assembly. The ground plane is also arranged to be substantially aligned (in the same plane) with the bent portion of the needle 102.

Alternatively, in one implementation, the ground plane is arranged to be part of the handle. In another implementation, the electrode is movably coupled to transmission line. For example, the ground plane may be pivotly or slidably coupled to the transmission line. In another implementation, the ground plane is biased to contact the tissue.

A method for using the described needle ablation assembly in treating an organ will now be described. The method includes providing a surgical device 100 having a needle 102 coupled to a transmission line 108. The transmission line 108 is arranged to have a portion with a longitudinal axis 110 and a proximal end 120 coupled to an electromagnetic energy source. By way of example, a microwave energy source that generates energy in the microwave frequency range works well. Furthermore, the needle 102 includes a distal end 104 that is adapted to penetrate through a wall of an organ 106 and an antenna 130 for generating a microwave field. By way of example, the organ may be a human heart and the wall may be the myocardium of the heart. The antenna 130 is also arranged to be in an angular position relative to the longitudinal axis 110 of the transmission line 108. By way of example, the needle or the transmission line may be pre-shaped or bent at a predetermined angular position.

In accordance with the present invention, the method includes introducing the surgical device 100 into a body cavity. This may be by penetration of the body or through an access device inserted in the body. By way of example, in most coronary applications, the introducing may be provided through the thorax region of the body or through an opened chest. The method further includes penetrating a wall of the organ 106 with the distal end 104 of the needle 102 and introducing the needle 102 through the wall of the organ 106 and into an interior chamber thereof. By way of example, the surgical tool 100 can be introduced into the left atrium, the right atrium, the right ventricle, or the left ventricle of the heart. Furthermore, before penetration a purse string suture may be placed in the heart wall proximate the area targeted for penetration so as to provide tension during penetration. Purse string sutures are well known in the art and for the sake of brevity will not be discussed in more detail.

The method also includes positioning the needle 102 inside the interior chamber of the organ 106 such that the antenna 130 substantially matches the shape and/or angular position of the wall to be ablated. By way of example, the position may place the antenna substantially parallel to the interior surface of the penetrated wall and proximate the targeted tissue. Furthermore, the method includes generating a microwave field at the antenna that is sufficiently strong to cause tissue ablation within the generated microwave field.

Although only a few embodiments of the present invention have been described in detail, it should be understood that the present invention may be embodied in many other specific forms without departing from the spirit or scope of the invention. Particularly, the invention has been described in terms of a microwave ablation assembly for cardiac applications. However, it should be appreciated that the present invention could be used for a wide variety of alternative applications as well. By way of example, the present invention may be used in most procedures relating to the ablation of internal biological tissues, and more particularly, to the ablation of organs with cavities such as the heart, the stomach, the intestines and the like. Further, although the described assembly works extremely well for microwave applications, it may be used to transmit electromagnetic energy at other frequencies as well, for example, radio frequencies. Additionally, it is contemplated that the present invention may be practiced with other suitable ablative energy sources. By way of example, the present invention may be practiced with electrical current, ultrasound, electrical pulses, cryothermy, lasers, and the like. In such configurations, the ablation element may be one or several metallic electrodes, a laser transducer, a cryogenic transducer, or an ultrasound transducer, while the transmission element may be a metallic wire, a fiber optic or a tube carrying cooling fluid.

Furthermore, while the invention has been described in terms of several preferred embodiments, there are alterations, permutations, and equivalents, which full within the scope of this invention. By way of example, the ablation assembly may also include a series of mapping electrodes to detect electrophysiological signals from the cardiac tissue. Such electrodes can be used to map the relevant region of the heart prior to or after an ablation procedure. The electrodes may also be used to monitor the patient's condition and/or the nature of the ablation process. The electrodes may be disposed along the antenna device in the antenna region, along the transmission line, or along the clamping finger. The electrode bands may optionally be divided into a plurality of electrically isolated electrode segments. The information obtained from the electrodes is transmitted via electrode wires to external electronics such as an EP signal monitoring device. Filtering of the signal may be provided as necessary. In alternative embodiments, some of the external electronics could be incorporated into the power supply and/or the power supply could use information obtained from the electrodes in its control scheme.

In addition, the ablation assembly may also include a series of thermometry elements for measuring the temperature of the tissue. The thermometry elements may take the form of thermocouple wires, fiber optic sensor cables or any other suitable thermometry devices. The thermometry elements may be disposed along the antenna device, along the transmission line, or along the clamping finger.

Moreover, although the ground plane has been shown and described as being directly connected to the outer conductor of the transmission line, it may be indirectly grounded through an external conductor. This type of arrangement also creates a more intense electromagnetic field, but not to the same degree as the directly connected ground plane.

Further, it is also contemplated that the ablation assembly may be widely modified without departing from the scope of this invention. By way of example, balloons may be positioned at the inner or outer penetration of the organ to seal the puncture site. Additionally, the ablation assembly may include a chemical delivery system for injecting chemical agents into the penetrated tissue. Further still, purse string sutures may be used to help seal the puncture site of the organ. It should also be noted that there are many ways of implementing the methods and apparatuses of the present invention. It is therefore intended that the following appended claims be interpreted as including all such alterations, permutations, and equivalents as fall within the true spirit and scope of the present invention.

What is claimed:

1. A system for ablating an interior tissue region of an organ or duct within a body of a patient comprising:
    an ablation tool including an elongated antenna device electrically coupled to a coaxial transmission line that is electrically coupled to a source of microwave energy for delivering sufficient microwave energy to the antenna device to effect ablation of a tissue region within the interior of the organ or duct, the coaxial transmission line including an inner conductor, an outer conductor and a dielectric medium disposed between the inner and outer conductors, the antenna device including an antenna that is coupled to a distal end of the inner conductor of the coaxial transmission line and an enclosure that encapsulates the antenna with a dielectric material; and
    an introducer that is not connected to the source of microwave energy, said introducer having a proximal end, a sharpened distal end for penetrating through a wall of the organ or duct, and a lumen which is sized and dimensioned for slidable movement of the antenna device therein, the antenna device being configured to be deployed into the interior of the organ or duct through the sharpened distal end of the introducer with a deployed shape that is straight and at a skewed angular orientation relative to a longitudinal axis of the introducer, over an entire exposed length of the antenna device that extends distally from the introducer, to orient the antenna device in a direction towards and substantially parallel to an interior portion of the penetrated wall for producing a linear lesion at the tissue region of the penetrated wall which is targeted for ablation.

2. A system for ablating an interior tissue region of an organ or duct within a body of a patient comprising:
    an ablation tool including an elongated antenna device electrically coupled to a coaxial transmission line that is electrically coupled to a source of microwave energy, the coaxial transmission line delivering microwave energy to the antenna device so as to effect ablation of a tissue region within the interior of the organ or duct, the coaxial transmission line including an inner conductor, an outer conductor and a dielectric medium disposed between the inner and outer conductors, the antenna device including an antenna that is coupled to a distal end of the inner conductor of the coaxial transmission line and an enclosure that encapsulates the antenna with a dielectric material; and
    an introducer configured to carry at least a portion of the ablation tool, the introducer having a proximal end, a sharpened distal end for penetrating through a wall of the organ or duct, and at least one lumen which is sized and dimensioned for slidable receipt of at least the antenna device of the ablation tool therethrough, the antenna device being configured to be deployed into the interior of the organ or duct through the sharpened distal end of the introducer, wherein upon deployment the antenna device assumes a predetermined position in a straight direction, over an entire exposed length of the antenna device that extends distally from the introducer, towards the tissue region targeted for ablation and substantially parallel to the tissue region targeted for ablation, wherein said ablation tool comprises a steering mechanism associated with the proximal end of the tool which, upon manipulation, is configured to cause at least a portion of the antenna device to assume an angular orientation relative to a longitudinal axis of the tool.

3. The system of claim 2 wherein said angular orientation is between about 0 and 90 degrees relative to the longitudinal axis of the tool.

4. The system of claim 2 wherein said angular orientation is between about 45 and 135 degrees relative to the longitudinal axis of the tool.

5. The system of claim 2 wherein the antenna further comprises a microwave antenna which is electrically coupled to the transmission line.

6. A microwave ablation device for ablating an interior portion of a wall of a beating heart, the microwave ablation device comprising:
    a probe configured to penetrate the wall of the beating heart, the probe having a proximal end portion and a distal end portion having a sharpened distal end and wherein said probe is not configured to deliver ablation energy; and
    a microwave energy delivery antenna portion slidably disposed within the distal end portion of the probe, said sharpened distal end of said probe being configured to penetrate the wall of the beating heart to facilitate deployment from the distal end within an interior cavity of the beating heart of the microwave energy portion, with a deployed shape that is straight and at a skewed angular orientation relative to a longitudinal axis of the probe, over an entire exposed length of the antenna portion that extends distally from the probe, and configured to substantially match the shape of the interior portion of the wall for linearly ablating the interior portion of the wall of the beating heart proximate the deployed microwave energy delivery portion.

7. The device of claim 6 wherein said energy delivery portion comprises a microwave antenna which is located within said distal end portion of the shaft.

8. The device of claim 6 wherein said distal end portion of the device is preshaped to extend at an angle relative to a longitudinal axis of the shaft.

9. The device of claim 8 wherein said distal end portion extends at an angle of between about 0 and 90 degrees relative to the longitudinal axis of the shaft.

10. The device of claim 8 wherein said distal end portion extends at an angle of between about 45 and 135 degrees relative to the longitudinal axis of the shaft.

11. The device of claim 6 wherein said distal end portion comprises a dielectric material which substantially surrounds the distal end portion.

12. An ablation device for ablating heart tissue, the device comprising:
    an elongated shaft that is not connected to a source of ablation energy, said elongated shaft having a proximal end portion and a sharpened distal end; and
    a pre-shaped elongated energy delivery antenna portion slidably disposed within the elongated shaft proximate to the distal end, said energy delivery portion including a shape memory material that facilitates bending following deployment of the energy delivery portion from the distal end and that facilitates straightening in response to retraction of the energy delivery portion relative to the distal end of the elongated shaft, the deployed shape of the elongated energy portion being straight and at a skewed angular orientation relative to a longitudinal axis of the probe, over an entire exposed length of the antenna portion that extends distally from the elongated shaft, and having a contour of an inner wall of a heart to substantially conform the elongated energy delivery portion to the inner wall of the heart with the distal end of the elongated shaft penetrating through the inner wall of the heart.

13. The device of claim 12 wherein said elongated energy delivery portion is pre-shaped to extend substantially straight from the distal end at a skewed angle relative to a longitudinal axis of the shaft.

14. The device of claim 13 wherein said energy delivery portion extends at an angle greater than 0 and less than 90 degrees relative to the longitudinal axis of the shaft.

15. The device of claim 13 wherein said energy delivery portion extends at an angle of between about 45 and 135 degrees relative to the longitudinal axis of the shaft.

16. The device of claim 12 wherein the energy delivery portion is configured to substantially conform to a tissue region of the inner wall surrounding a pulmonary vein.

17. The device of claim 12 wherein the energy delivery portion is configured to substantially conform to at least a portion of a lateral inner wall of the right atrium.

18. An ablation assembly, comprising:
    a probe having a sharpened distal end configured for percutaneously penetrating through a wall of an organ for introducing a longitudinal energy delivery member into a cavity within the organ, the longitudinal energy delivery antenna member being deployable from the distal end of the probe within the cavity of the organ, and being configured to assume a deployed shape that is straight and at a skewed angular orientation relative to a longitudinal axis of the probe, over an entire exposed length of the antenna member that extends distally from the distal end of the probe, to conform to an inner wall of the organ for producing a substantially linear lesion on the inner wall of the organ in response to ablative energy delivered to the longitudinal energy delivery member, and wherein the probe is not configured to deliver ablative energy.

19. The ablation assembly as recited in claim 18 in which the longitudinal energy delivery member is deployable from the distal end at an angular position relative to an elongated axis of the probe near the distal end thereof that places the longitudinal energy delivery member substantially parallel to the inner wall of the organ with each longitudinal portion of the longitudinal energy delivery member equidistant from the inner wall of the organ.

20. The ablation device as recited in claim 12 wherein the energy delivery portion is configured to produce an electromagnetic field that is concentrated on a side of the energy delivery portion oriented proximate to the inner wall of the heart in order to produce a linear lesion at the inner wall of the heart.

21. The ablation device of claim 12, further comprising an antenna enclosure encapsulating at least a portion of said antenna portion.

22. The ablation device of claim 21, wherein said antenna enclosure comprises a dielectric material.

23. An ablation system for ablating an interior tissue region of an organ or duct within a body of a patient, said system comprising:
    a probe configured to penetrate a wall of the organ or duct, but not to deliver ablation energy, the probe having a proximal end portion and a distal end portion having a sharpened distal end; and
    an ablation tool configured to be slidably passed within said probe, said ablation tool comprising an ablation antenna element at a distal end thereof and an ablation energy supply line connected proximally to said ablation antenna element, said ablation antenna element having a first, straight configuration assumed when being passed through said probe, and a second, bent configuration assumed when said ablation antenna element extends distally from said distal end of said probe, wherein said ablation antenna element is bent with respect to a longitudinal axis of said probe and extends straight away from a bend where said ablation antenna element is bent, over an entire length of the antenna element that extends distally from a distal end of the probe.

24. The ablation system of claim 23, wherein said ablation element comprises a microwave antenna.

25. The ablation system of claim 23, wherein said probe and said ablation tool are independent components and wherein said ablation tool can be completely removed from within said probe.

26. The ablation system of claim 23, wherein said ablation tool and probe are integrally provided within said system.

27. The ablation system of claim 26, further comprising a handle proximally connected to said probe, and wherein longitudinal sliding of said ablation tool within said probe is facilitated via said handle.

28. The ablation system of claim 23, further comprising a biasing member configured to bias said ablation element from said substantially straight configuration to said bent configuration.

* * * * *